(12) United States Patent
Johnson et al.

(10) Patent No.: US 7,915,410 B2
(45) Date of Patent: Mar. 29, 2011

(54) ACYCLIC $I_{Kur}$ INHIBITORS

(75) Inventors: James A. Johnson, Pennington, NJ (US); Yoon Jeon, Belle Mead, NJ (US); John Lloyd, Yardley, PA (US); Heather Finlay, Skillman, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 805 days.

(21) Appl. No.: 11/518,483

(22) Filed: Sep. 8, 2006

(65) Prior Publication Data

US 2007/0082909 A1  Apr. 12, 2007

Related U.S. Application Data

(60) Provisional application No. 60/715,679, filed on Sep. 9, 2005.

(51) Int. Cl.
*C07D 237/34* (2006.01)
*A61K 31/502* (2006.01)

(52) U.S. Cl. .................... 544/237; 514/248

(58) Field of Classification Search .............. 544/237; 514/248
See application file for complete search history.

(56) References Cited

U.S. PATENT DOCUMENTS

| | | | |
|---|---|---|---|
| 4,147,698 A | 4/1979 | Wade et al. | |
| 4,751,302 A | 6/1988 | Ibuki et al. | |
| 5,081,131 A | 1/1992 | Tomcufcik et al. | |
| 5,100,895 A | 3/1992 | Hansen et al. | |
| 5,654,307 A | 8/1997 | Bridges et al. | |
| 5,981,533 A | 11/1999 | Traxler et al. | |
| 6,084,095 A | 7/2000 | Bridges et al. | |
| 6,258,812 B1 | 7/2001 | Bold et al. | |
| 6,265,410 B1 | 7/2001 | Bridges et al. | |
| 6,303,637 B1 | 10/2001 | Bao et al. | |
| 6,455,534 B2 | 9/2002 | Bridges et al. | |
| 6,514,974 B2 | 2/2003 | Bold et al. | |
| 6,521,620 B1 | 2/2003 | Bridges et al. | |
| 6,632,836 B1 | 10/2003 | Baker et al. | |
| 6,710,047 B2 | 3/2004 | Bold et al. | |
| 6,713,484 B2 | 3/2004 | Bridges et al. | |
| 2004/0266779 A1 | 12/2004 | Anderson | |
| 2005/0054662 A1 | 3/2005 | Hennequin et al. | |

FOREIGN PATENT DOCUMENTS

| | | |
|---|---|---|
| DE | 11 74 783 | 7/1964 |
| FR | 2 220 265 | 10/1974 |
| FR | 2 276 044 | 1/1976 |
| GB | 2 295 387 | 5/1996 |
| JP | 60 061569 | 4/1985 |
| WO | WO 96/19474 | 6/1996 |
| WO | WO 98/35958 | 8/1998 |
| WO | WO 00/25770 | 5/2000 |
| WO | WO 00/25786 | 5/2000 |
| WO | WO 01/32632 * | 5/2001 |
| WO | WO 01/55143 | 8/2001 |
| WO | WO 2004/002485 | 1/2004 |
| WO | WO 2004/028542 | 4/2004 |
| WO | WO 2004/032935 | 4/2004 |
| WO | WO 2004/033042 | 4/2004 |
| WO | WO 2005/030726 | 4/2005 |
| WO | WO 2005/030727 | 4/2005 |
| WO | WO 2005/030729 | 4/2005 |
| WO | WO 2005/034837 | 4/2005 |
| WO | WO 2005/087227 | 9/2005 |

OTHER PUBLICATIONS

Kubinyi (3D QSAR in Drug Design: Ligand-Protein Interactions and Molecular Similarity, vol. 2-3, Springer, 1998, 800 pages). Provided TOC and pp. 243-244.*
Martin et al. (European Journal of Pharmacology (1995), 276(1/2), 9-19).*
May, H. et al., Arzneim. Forsch., vol. 30, No. 9, 1980, pp. 1486-1493.

* cited by examiner

*Primary Examiner* — Robert Havlin
(74) *Attorney, Agent, or Firm* — Mary K. VanAtten; Terrence J. Bogie

(57) ABSTRACT

A compound of formula I

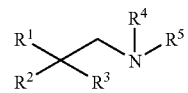

wherein $R^1$, $R^2$, $R^3$, $R^4$ and $R^5$ are described herein.

2 Claims, No Drawings

ACYCLIC $I_{Kur}$ INHIBITORS

RELATED APPLICATION

This application claims the benefit of U.S. Provisional Application No. 60/715,679, filed on Sep. 9, 2005, incorporated herein by reference in its entirety.

FIELD OF THE INVENTION

The present invention provides for acyclic compounds useful as inhibitors of potassium channel function (especially inhibitors of the $K_v1$ subfamily of voltage gated $K^+$ channels, more especially inhibitors of $K_v1.5$ (which have been linked to the ultra-rapidly activating delayed rectifier $K^+$ current $I_{Kur}$), and/or $K_v1.3$ channels, and/or $K_v1.1$ channels) and to pharmaceutical compositions containing such compounds. The present invention further provides for methods of using such compounds in the treatment and prevention of arrhythmia, $I_{Kur}$-associated disorders, and other disorders mediated by ion channel function.

BACKGROUND OF THE INVENTION

The ultra-rapidly activating delayed rectifier $K^+$ current ($I_{Kur}$) is believed to represent the native counterpart to a cloned potassium channel designated $K_v1.5$ and, while present in human atrium, it appears to be absent in human ventricle. Furthermore, because of its rapidity of activation and limited slow inactivation, $I_{Kur}$ is believed to contribute significantly to repolarization in human atrium. Consequently, a specific blocker of $I_{Kur}$, that is a compound which blocks $K_v1.5$, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III antiarrhythmic agents. (Antiarrhythmic agents of Class III are drugs that cause a selective prolongation of the duration of the action potential without significant cardiac depression.)

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Although the underlying pathogenesis of each of these conditions may vary, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, lymphocytes recognize the foreign tissue antigens and begin to produce immune mediators which lead to graft rejection or graft-vs-host rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion in which both the normal and autoimmune responses are shut off. Indeed, patients treated with such nonspecific immunosuppressive agents are as likely to succumb to infection as they are to their autoimmune disease.

Cyclosporin A, which was approved by the US FDA in 1983 is currently the leading drug used to prevent rejection of transplanted organs. In 1993, FK-506 (Prograf) was approved by the US FDA for the prevention of rejection in liver transplantation. Cyclosporin A and FK-506 act by inhibiting the body's immune system from mobilizing its vast arsenal of natural protecting agents to reject the transplant's foreign protein. In 1994, Cyclosporin A was approved by the US FDA for the treatment of severe psoriasis and has been approved by European regulatory agencies for the treatment of atopic dermatitis. Though these agents are effective in fighting transplant rejection, Cyclosporin A and FK-506 are known to cause several undesirable side effects including nephrotoxicity, neurotoxicity, and gastrointestinal discomfort. Therefore, a selective immunosuppressant without these side effects still remains to be developed. Potassium channel inhibitors as described here promise to be the solution to this problem, since inhibitors of $K_v1.3$, for example, are immunosuppressive. See, Wulff et al., "Potassium channels as therapeutic targets for autoimmune disorders," Curr Opin Drug Discov Devel. 2003 September; 6(5):640-7; Shah et al., "Immunosuppressive effects of a $K_v1.3$ inhibitor," Cell Immunol. 2003 February; 221(2):100-6; Hanson et al., "UK-78,282, a novel piperidine compound that potently blocks the $K_v1.3$ voltage-gated potassium channel and inhibits human T cell activation," Br J Pharmacol. 1999 April; 126(8):1707-16.

Inhibitors of $K_v1.5$ and other $K_v1.x$ channels stimulate gastrointestinal motility. Thus, the compounds of the invention are believed to be useful in treating motility disorders such as reflux esophagitis. See, Frey et al., "Blocking of cloned and native delayed rectifier K channels from visceral smooth muscles by phencyclidine," Neurogastroenterol Motil. 2000 December; 12(6):509-16; Hatton et al., "Functional and molecular expression of a voltage-dependent K(+) channel ($K_v1.1$) in interstitial cells of Cajal," J Physiol. 2001 Jun. 1; 533(Pt 2):315-27; Vianna-Jorge et al., "Shaker-type $K_v1$ channel blockers increase the peristaltic activity of guinea-pig ileum by stimulating acetylcholine and tachykinins release by the enteric nervous system," Br J Pharmacol. 2003 January; 138(1):57-62; Koh et al., "Contribution of delayed rectifier potassium currents to the electrical activity of murine colonic smooth muscle," J. Physiol. 1999 Mar. 1; 515 (Pt 2):475-87.

Inhibitors of $K_v1.5$ relax pulmonary artery smooth muscle. Thus, the compounds of the invention are believed to be useful in treating hypertension and otherwise improving vascular health. See, Davies et al., "$K_v$ channel subunit expression in rat pulmonary arteries," Lung. 2001; 179(3):147-61. Epub 2002 Feb. 4; Pozeg et al., "In vivo gene transfer of the O2-sensitive potassium channel $K_v1.5$ reduces pulmonary hypertension and restores hypoxic pulmonary vasoconstriction in chronically hypoxic rats," Circulation. 2003 Apr. 22; 107(15):2037-44. Epub 2003 Apr. 14.

Inhibitors of $K_v1.3$ increase insulin sensitivity. Hence, the compounds of the invention are believed to be useful in treating diabetes. See, Xu et al., "The voltage-gated potassium channel $K_v1.3$ regulates peripheral insulin sensitivity," Proc. Natl. Acad. Sci. U.S.A. 2004 Mar. 2; 101(9):3112-7. Epub 2004 Feb. 23 (epublished 2004 Feb. 23); MacDonald et al., "Members of the $K_v1$ and $K_v2$ voltage-dependent K(+) channel families regulate insulin secretion," Mol. Endocrinol. 2001 August; 15(8):1423-35; MacDonald et al., "Voltage-dependent K(+) channels in pancreatic beta cells: role, regulation and potential as therapeutic targets," Diabetologia. 2003 August; 46(8):1046-62. Epub 2003 Jun. 27.

Stimulation of $K_v1.1$ is believed to reduce seizure activity by hyperpolarizing neurons. Thus, the compounds of the invention are believed to be useful in treating seizures, including seizures associated with epilepsy and other neurological diseases. See, Rho et al., "Developmental seizure susceptibility of kv1.1 potassium channel knockout mice," Dev Neurosci. 1999 November; 21(3-5):320-7; Coleman et al., "Subunit composition of $K_v1$ channels in human CNS," J Neurochem. 1999 August; 73(2):849-58; Lopantsev et al., "Hyperexcitability of CA3 pyramidal cells in mice lacking the potassium channel subunit $K_v1.1$," Epilepsia. 2003 December; 44(12):1506-12; Wickenden, "Potassium channels as anti-epileptic drug targets," Neuropharmacology. 2002 December; 43(7): 1055-60.

Inhibition of $K_v1.x$ channels improves cognition in animal models. Thus, the compounds of the invention are believed to be useful in improving cognition and/or treating cognitive disorders. See, Cochran et al., "Regionally selective alterations in local cerebral glucose utilization evoked by charybdotoxin, a blocker of central voltage-activated K+-channels," Eur J. Neurosci. 2001 November; 14(9):1455-63; Kourrich et al., "Kaliotoxin, a $K_v1.1$ and $K_v1.3$ channel blocker, improves associative learning in rats," Behav Brain Res. 2001 Apr. 8; 120(1):35-46.

SUMMARY OF THE INVENTION

In accordance with the present invention, acyclic compounds and related compounds are provided that have the general structure of formula I:

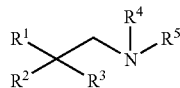

wherein $R^1$, $R^2$, $R^3$, $R^4$ and $R^5$ are defined below.

By use of a respective effective amount of at least one compound described herein, provided are methods of treating (including ameliorating) or preventing arrhythmias, atrial fibrillation, atrial flutter, supraventricular arrhythmias, gastrointestinal disorders (such as reflux esauphagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

DEFINITIONS

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be either fused, bridged and/or joined through one or more spiro unions. The term "substituted cycloalkyl" refers to a cycloalkyl group substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

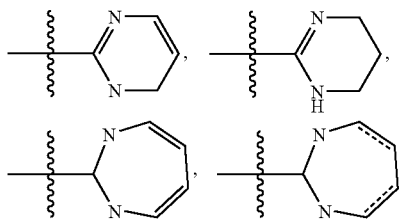

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

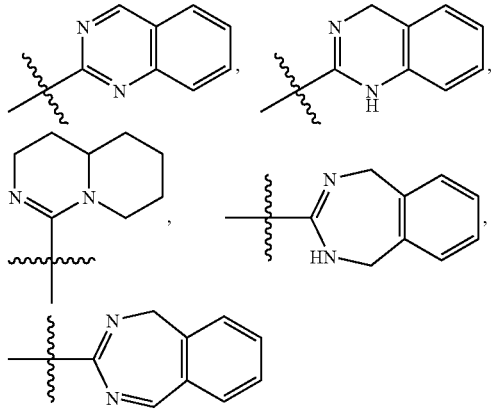

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

The term "alkanoyl" refers to alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

The compounds of formula I form salts or solvates which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

It will be understood that any given exemplary embodiment can be combined with one or more additional exemplary embodiments.

In accordance with the present invention, compounds of formula I are provided

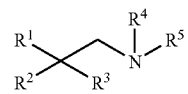

I or stereoisomers or pharmaceutically acceptable salts or prodrugs thereof, wherein:

$R^1$ is an aryl or heterocyclic ring, which may be optionally substituted with one or more $R^{10}$'s;

$R^2$ and $R^3$ are independently:

(a) halo, (b) $(C_1-C_6)$-alkoxy optionally substituted with one or more $R^{11}$'s, (c) $(C_1-C_4)$-perfluoroalkyl, (d) $(C_1-C_6)$-alkyl-$S(O)_n$—, (e) aryl-$(CH_2)_r$—$S(O)_n$—, (f) cyano, (g) —$CO_2H$, (h) —$CO(C_1-C_6)$-alkyl, (i) —$CO_2(C_1-C_6)$-alkyl, (j) —$CONR^8R^9$, (k) —$O(CO)NR^8R^9$, (l) —$NR^8(CO)NR^8R^9$, (m) —$NR^8R^9$, (n) hydrogen, (o) $C_1-C_{10}$-alkyl optionally substituted with one or more $R^{11}$'s, (p) $(C_2-C_{10})$-alkenyl optionally substituted with one or more $R^{11}$'s,
(q) $(C_2-C_{10})$-alkynyl optionally substituted with one or more $R^{11}$'s,
(r) aryl optionally substituted with one or more $R^{11}$'s,
(s) heterocyclyl optionally substituted with one or more $R^{11}$'s, or
(t) $-NR^8(CO)OR^{21}$,
provided that both $R^2$ and $R^3$ are not simultaneously hydrogen;
$R^4$ is:
(a) hydrogen,
(b) $C_1-C_{10}$-alkyl,
(c) $-CO(C_1-C_6)$-alkyl,
(d) $-CO$aryl,
(e) $-CO$heterocyclyl,
(f) $-CO_2(C_1-C_6)$-alkyl,
(g) $-CO_2$aryl,
(h) $-CO_2$heterocyclyl,
(i) $-CONR^8R^9$,
(j) $-S(O)_n$-alkyl,
(k) $-S(O)_n$-aryl,
(l) $-S(O)_n$-heterocyclyl, or
(m) $-S(O)_n-NR^8R^9$;
$R^5$ is

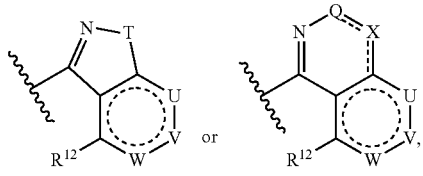

wherein the dashed line(s) represent an optional double bond;
T is O, S, C=O, N, $NR^{19}$ or $C(R^{20})_p$;
Q, X, U, V and W are independently O, S, C=O, N, $NR^{19}$ or $C(R^{20})_p$, provided that Q is not $C(R^{20})_p$ when X is N or $NR^{19}$;
$R^8$ and $R^9$ are independently:
(a) hydrogen,
(b) $-[(C=O)O_r]_s$aryl, wherein the aryl may be optionally substituted with one or more $R^{14}$'s,
(c) $-[(C=O)O_r]_s(C_2-C_8)$-alkenyl, wherein the alkenyl may be optionally substituted with one or more $R^{14}$'s,
(d) $-[(C=O)O_r]_s(C_1-C_8)$alkyl, wherein the alkyl may be optionally substituted with one or more $R^{14}$'s,
(e) $-S(O)_p(C_1-C_8)$alkyl, wherein the alkyl may be optionally substituted with one or more $R^{14}$'s,
(f) $-S(O)_pNR^{16}R^{17}$,
(g) $-C(=NR^{18})(NR^{16}R^{17})$, or
(h) heterocyclyl optionally substituted with one or more $R^{14}$'s,
or $R^8$ and $R^9$ are taken together with the nitrogen to which both are attached to form a 3- to 8-membered ring, which may optionally contain 1-4 heteroatoms selected from N, O, and S and be optionally substituted with one or more $R^{14}$'s;
$R^{10}$ is:
(a) halo,
(b) $-OH$,
(c) $-O[(C=O)O_r]_s(C_1-C_6)$-alkyl,
(d) $-O[(C=O)O_r]_s(C_2-C_6)$-alkenyl,
(e) $-O[(C=O)O_r]_s$aryl,
(f) $-O[(C=O)O_r]_s$heteroaryl,
(g) $(C_1-C_6)$-alkyl-$S(O)_n$—,
(h) aryl-$(C_1-C_6)$alkyloxy-,
(i) cyano,
(j) nitro,
(k) $-NR^8R^9$,
(l) $-O(CO)NR^8R^9$,
(m) $-CHO$,
(n) $-COOH$,
(o) $-CO(C_1-C_6)$-alkyl,
(p) $-CO_2(C_1-C_6)$-alkyl,
(q) $-CONR^8R^9$,
(r) aryl, which may optionally be substituted with one or more substituents selected from the group consisting of:
1) halo,
2) $-OH$,
3) $(C_1-C_6)$-alkyl,
4) $(C_1-C_4)$-perfluoroalkyl,
5) $(C_2-C_6)$-alkenyl,
6) $(C_2-C_6)$-alkynyl,
7) $(C_1-C_6)$-alkyloxy,
8) $(C_1-C_6)$-alkyl-$S(O)_n$—,
9) cyano,
10) $-COOH$,
11) $-CO(C_1-C_6)$-alkyl,
12) $-CO_2(C_1-C_6)$-alkyl,
13) $-CONR^8R^9$,
14) $-NR^8R^9$,
15) $-O(C=O)-(C_1-C_6)$-alkyl, and
16) $-O(C=O)NR^8R^9$,
(s) heteroaryl optionally substituted with one or more substituents selected from the group consisting of:
1) halo,
2) $-OH$,
3) $(C_1-C_6)$-alkyl,
4) $(C_1-C_4)$-perfluoroalkyl,
5) $(C_2-C_6)$-alkenyl,
6) $(C_2-C_6)$-alkynyl,
7) $(C_1-C_6)$-alkyloxy,
8) $(C_1-C_6)$-alkyl-$S(O)_n$—,
9) cyano,
10) $-COOH$,
11) $-CO(C_1-C_6)$-alkyl,
12) $-CO_2(C_1-C_6)$-alkyl,
13) $-CONR^8R^9$,
14) $-NR^8R^9$,
15) $-O(C=O)-(C_1-C_6)$-alkyl, and
16) $-O(C=O)NR^8R^9$,
(t) heterocyclo other than heteroaryl which is optionally substituted with one or more substituents selected from the group consisting of:
1) halo,
2) $-OH$,
3) $(C_1-C_6)$-alkyl,
4) $(C_1-C_4)$-perfluoroalkyl,
5) $(C_2-C_6)$-alkenyl,
6) $(C_2-C_6)$-alkynyl,
7) $(C_1-C_6)$-alkyloxy,
8) $(C_1-C_6)$-alkyl-$S(O)_n$—,
9) cyano,
10) $-COOH$,
11) $-CO(C_1-C_6)$-alkyl,
12) $-CO_2(C_1-C_6)$-alkyl,
13) $-CONR^8R^9$,
14) $-NR^8R^9$,
15) $-O(C=O)-(C_1-C_6)$-alkyl, and
16) $-O(C=O)NR^8R^9$, (u) benzyl-S(O)$_n$—,
(v) (C$_2$-C$_{10}$)-alkenyl, which may optionally be substituted with one or more substituents selected from the group consisting of:
1) halo,
2) —OH,
3) (C$_1$-C$_6$)-alkyloxy,
4) (C$_1$-C$_6$)-alkyl-S(O)$_n$—,
5) cyano,
6) —COOH,
7) —CO(C$_1$-C$_6$)-alkyl,
8) —CO$_2$(C$_1$-C$_6$)-alkyl,
9) —CONR$^8$R$^9$,
10) —NR$^8$R$^9$,
11) —O(C=O)—(C$_1$-C$_6$)-alkyl, and
12) —O(C=O)NR$^8$R$^9$,
(w) (C$_2$-C$_{10}$)-alkynyl wherein alkynyl is optionally substituted with one or more substituents selected from the group consisting of:
1) halo,
2) —OH,
3) (C$_1$-C$_6$)-alkyloxy,
4) (C$_1$-C$_6$)-alkyl-S(O)$_n$—,
5) cyano,
6) —COOH,
7) —CO(C$_1$-C$_6$)-alkyl,
8) —CO$_2$(C$_1$-C$_6$)-alkyl,
9) —CONR$^8$R$^9$,
10) —NR$^8$R$^9$,
11) —O(C=O)—(C$_1$-C$_6$)-alkyl, and
12) —O(C=O)NR$^8$R$^9$,
(x) —(C$_1$-C$_{10}$)-alkyl, which may optionally be substituted with one or more substituents selected from the group consisting of:
1) halo,
2) —OH,
3) (C$_1$-C$_6$)-alkyloxy,
4) (C$_1$-C$_6$)-alkyl-S(O)$_n$—,
5) benzyl-S(O)$_n$—,
6) cyano,
7) —COOH,
8) —CO(C$_1$-C$_6$)-alkyl,
9) —CO$_2$(C$_1$-C$_6$)-alkyl,
10) —CONR$^8$R$^9$,
11) —NR$^8$R$^9$,
12) —(C=O)—(C$_1$-C$_6$)-alkyl, and
13) —(C=O)NR$^8$R$^9$;
R$^{11}$ is:
(a) halo,
(b) —OH,
(c) —O[(C=O)O$_r$]$_s$(C$_1$-C$_6$)-alkyl,
(d) —O[(C=O)O$_r$]$_s$(C$_2$-C$_6$)-alkenyl,
(e) —O[(C=O)O$_r$]$_s$aryl,
(f) —O[(C=O)O$_r$]$_s$heteroaryl,
(g) (C$_1$-C$_6$)-alkyl-S(O)$_n$—,
(h) aryl-(C$_1$-C$_6$)alkyloxy-,
(i) cyano,
(j) —NR$^8$R$^9$,
(k) —O(CO)NR$^8$R$^9$,
(l) —COOH,
(m) —CO(C$_1$-C$_6$)-alkyl,
(n) —CO$_2$(C$_1$-C$_6$)-alkyl,
(o) —CONR$^8$R$^9$,
(p) aryl, which may optionally be substituted with one or more substituents selected from the group consisting of:
1) halo,
2) —OH,
3) (C$_1$-C$_6$)-alkyl,
4) aryl-(C$_1$-C$_6$)alkyloxy-,
5) (C$_1$-C$_4$)-perfluoroalkyl,
6) (C$_2$-C$_6$)-alkenyl,
7) (C$_2$-C$_6$)-alkynyl,
8) (C$_1$-C$_6$)-alkyloxy,
9) (C$_1$-C$_6$)-alkyl-S(O)$_n$—,
10) cyano,
11) —COOH,
12) —CO(C$_1$-C$_6$)-alkyl,
13) —CO$_2$(C$_1$-C$_6$)-alkyl,
14) —CONR$^8$R$^9$,
15) —NR$^8$R$^9$,
16) —O(C=O)—(C$_1$-C$_6$)-alkyl, and
17) —O(C=O)NR$^8$R$^9$,
(q) heteroaryl optionally substituted with one or more substituents selected from the group consisting of:
1) halo,
2) —OH,
3) (C$_1$-C$_6$)-alkyl,
4) aryl-(C$_1$-C$_6$)alkyloxy-,
5) (C$_1$-C$_4$)-perfluoroalkyl,
6) (C$_2$-C$_6$)-alkenyl,
7) (C$_2$-C$_6$)-alkynyl,
8) (C$_1$-C$_6$)-alkyloxy,
9) (C$_1$-C$_6$)-alkyl-S(O)$_n$—,
10) cyano,
11) —COOH,
12) —CO(C$_1$-C$_6$)-alkyl,
13) —CO$_2$(C$_1$-C$_6$)-alkyl,
14) —CONR$^8$R$^9$,
15) —NR$^8$R$^9$,
16) —O(C=O)—(C$_1$-C$_6$)-alkyl, and
17) —O(C=O)NR$^8$R$^9$,
(r) heterocyclo other than heteroaryl which is optionally substituted with one or more substituents selected from the group consisting of:
1) halo,
2) —OH,
3) (C$_1$-C$_6$)-alkyl,
4) aryl-(C$_1$-C$_6$)alkyloxy-,
5) (C$_1$-C$_4$)-perfluoroalkyl,
6) (C$_2$-C$_6$)-alkenyl,
7) (C$_2$-C$_6$)-alkynyl,
8) (C$_1$-C$_6$)-alkyloxy,
9) (C$_1$-C$_6$)-alkyl-S(O)$_n$—,
10) cyano,
11) —COOH,
12) —CO(C$_1$-C$_6$)-alkyl,
13) —CO$_2$(C$_1$-C$_6$)-alkyl,
14) —CONR$^8$R$^9$,
15) —NR$^8$R$^9$,
16) —O(C=O)—(C$_1$-C$_6$)-alkyl, and
17) —O(C=O)NR$^8$R$^9$,
(s) —(C$_2$-C$_{10}$)-alkenyl, which may optionally be substituted with one or more substituents selected from the group consisting of:
1) halo,
2) —OH,
3) (C$_1$-C$_6$)-alkyloxy
4) (C$_1$-C$_6$)-alkyl-S(O)$_n$—,
5) phenyl-(C$_1$-C$_6$)-alkyloxy-,
6) cyano,
7) —CHO,
8) —COOH,
9) —CO(C$_1$-C$_6$)-alkyl,
10) —CO$_2$(C$_1$-C$_6$)-alkyl, 11) —CONR$^8$R$^9$,
12) —NR$^8$R$^9$,
13) aryl,
14) heteroaryl as defined above,
15) heterocyclo other than heteroaryl as defined above,
16) —O(C=O)—(C$_1$-C$_6$)-alkyl, and
17) —O(C=O)NR$^8$R$^9$, (t) (C$_2$-C$_{10}$)-alkynyl wherein alkynyl is optionally substituted with one or more substituents selected from the group consisting of:
1) halo,
2) —OH,
3) (C$_1$-C$_6$)-alkyloxy,
4) (C$_1$-C$_6$)-alkyl-S(O)$_n$—,
5) phenyl-(C$_1$-C$_6$)-alkyloxy-,
6) cyano,
7) vinyl,
8) —CHO,
9) —COOH,
10) —CO(C$_1$-C$_6$)-alkyl,
11) —CO$_2$(C$_1$-C$_6$)-alkyl,
12) —CONR$^8$R$^9$,
13) —NR$^8$R$^9$,
14) aryl, wherein aryl is defined as above,
15) heteroaryl as defined above,
16) heterocyclyl other than heteroaryl as defined above,
17) —O(C=O)—(C$_1$-C$_6$)-alkyl, and
18) —O(C=O)NR$^8$R$^9$, (u) —(C$_1$-C$_{10}$)-alkyl, which may optionally be substituted with one or more substituents selected from the group consisting of:
1) halo,
2) —OH,
3) (C$_1$-C$_6$)-alkyloxy,
4) (C$_1$-C$_6$)-alkyl-S(O)$_n$—,
5) benzyl-S(O)$_n$—,
6) cyano,
7) —COOH,
8) —CO(C$_1$-C$_6$)-alkyl,
9) —CO$_2$(C$_1$-C$_6$)-alkyl,
10) —CONR$^8$R$^9$,
11) —NR$^8$R$^9$,
12) —O(C=O)—(C$_1$-C$_6$)-alkyl, and
13) —O(C=O)NR$^8$R$^9$, (v) —O(CH$_2$)$_m$-heteroaryl as defined above;
R$^{12}$ is:
(a) halo,
(b) —OH,
(c) —O[(C=O)O$_r$]$_s$(C$_1$-C$_6$)-alkyl,
(d) —O[(C=O)O$_r$]$_s$(C$_2$-C$_6$)-alkenyl,
(e) —O[(C=O)O$_r$]$_s$aryl,
(f) —O[(C=O)O$_r$]$_s$heteroaryl,
(g) (C$_1$-C$_6$)-alkyl-S(O)$_n$—,
(h) aryl-(C$_1$-C$_6$)alkyloxy-,
(i) cyano,
(j) nitro,
(k) —NR$^8$R$^9$,
(l) —O(CO)NR$^8$R$^9$,
(m) —HO,
(n) —COOH,
(o) —O(C$_1$-C$_6$)-alkyl,
(p) —CO$_2$(C$_1$-C$_6$)-alkyl,
(q) —CONR$^8$R$^9$,
(r) aryl, which may optionally be substituted with one or more substituents selected from the group consisting of:
1) halo,
2) —OH,
3) (C$_1$-C$_6$)-alkyl,
4) (C$_1$-C$_4$)-perfluoroalkyl,
5) (C$_2$-C$_6$)-alkenyl,
6) (C$_2$-C$_6$)-alkynyl,
7) (C$_1$-C$_6$)-alkyloxy,
8) (C$_1$-C$_6$)-alkyl-S(O)$_n$—,
9) cyano,
10) —COOH,
11) —CO(C$_1$-C$_6$)-alkyl,
12) —CO$_2$(C$_1$-C$_6$)-alkyl,
13) —CONR$^8$R$^9$,
14) —NR$^8$R$^9$,
15) —O(C=O)—(C$_1$-C$_6$)-alkyl, and
16) —O(C=O)NR$^8$R$^9$, (s) heteroaryl optionally substituted with one or more substituents selected from the group consisting of:
1) halo,
2) —OH,
3) (C$_1$-C$_6$)-alkyl,
4) (C$_1$-C$_4$)-perfluoroalkyl,
5) (C$_2$-C$_6$)-alkenyl,
6) (C$_2$-C$_6$)-alkynyl,
7) (C$_1$-C$_6$)-alkyloxy,
8) (C$_1$-C$_6$)-alkyl-S(O)$_n$—,
9) cyano,
10) —COOH,
11) —CO(C$_1$-C$_6$)-alkyl,
12) —CO$_2$(C$_1$-C$_6$)-alkyl,
13) —CONR$^8$R$^9$,
14) —NR$^8$R$^9$,
15) —O(C=O)—(C$_1$-C$_6$)-alkyl, and
16) —O(C=O)NR$^8$R$^9$, (t) heterocyclo other than heteroaryl which is optionally substituted with one or more substituents selected from the group consisting of:
1) halo,
52) —OH,
3) (C$_1$-C$_6$)-alkyl,
4) (C$_1$-C$_4$)-perfluoroalkyl,
5) (C$_2$-C$_6$)-alkenyl,
6) (C$_2$-C$_6$)-alkynyl,
7) (C$_1$-C$_6$)-alkyloxy,
8) (C$_1$-C$_6$)-alkyl-S(O)$_n$—,
9) cyano,
10) —COOH,
11) —CO(C$_1$-C$_6$)-alkyl,
12) —CO$_2$(C$_1$-C$_6$)-alkyl,
13) —CONR$^8$R$^9$,
14) —NR$^8$R$^9$,
15) —O(C=O)—(C$_1$-C$_6$)-alkyl, and
16) —O(C=O)NR$^8$R$^9$, (u) benzyl-S(O)$_n$—,
(v) (C$_2$-C$_{10}$)-alkenyl, which may optionally be substituted with one or more substituents selected from the group consisting of:
1) halo,
2) —OH,
3) (C$_1$-C$_6$)-alkyloxy,
4) (C$_1$-C$_6$)-alkyl-S(O)$_n$—,
5) cyano,
6) —COOH,
7) —CO(C$_1$-C$_6$)-alkyl,
8) —CO$_2$(C$_1$-C$_6$)-alkyl,
9) —CONR$^8$R$^9$,
10) —NR$^8$R$^9$,
11) —O(C=O)—(C$_1$-C$_6$)-alkyl, and
12) —O(C=O)NR$^8$R$^9$, (w) $(C_2-C_{10})$-alkynyl wherein alkynyl is optionally substituted with one or more substituents selected from the group consisting of:
1) halo,
2) —OH,
3) $(C_1-C_6)$-alkyloxy,
4) $(C_1-C_6)$-alkyl-$S(O)_n$—,
5) cyano,
6) —COOH,
7) —CO$(C_1-C_6)$-alkyl,
8) —CO$_2(C_1-C_6)$-alkyl,
9) —CONR$^8$R$^9$,
10) —NR$^8$R$^9$,
11) —O(C=O)—$(C_1-C_6)$-alkyl, and
12) —O(C=O)NR$^8$R$^9$, (x) —$(C_1-C_{10})$-alkyl, which may optionally be substituted with one or more substituents selected from the group consisting of:
1) halo,
2) —OH,
3) $(C_1-C_6)$-alkyloxy,
4) $(C_1-C_6)$-alkyl-$S(O)_n$—,
5) benzyl-$S(O)_n$—,
6) cyano,
7) —COOH,
8) —CO$(C_1-C_6)$-alkyl,
9) —CO$_2(C_1-C_6)$-alkyl,
10) —CONR$^8$R$^9$,
11) —NR$^8$R$^9$,
12) —O(C=O)—$(C_1-C_6)$-alkyl, and
13) —O(C=O)NR$^8$R$^9$, (y) =O;

R$^{14}$ is:
(a) halo,
(b) —OH,
(c) —O[(C=O)O$_r$]$_s$$(C_1-C_6)$-alkyl,
(d) —O[(C=O)O$_r$]$_s$$(C_2-C_6)$-alkenyl,
(e) —O[(C=O)O$_r$]$_s$aryl,
(f) —O[(C=O)O$_r$]$_s$heteroaryl,
(g) $(C_1-C_6)$-alkyl-$S(O)_n$—,
(h) aryl-$(C_1-C_6)$alkyloxy-,
(i) cyano,
(j) nitro,
(k) —NR$^8$R$^9$,
(l) —O(CO)NR$^8$R$^9$,
(m) —CHO,
(n) —COOH,
(o) —CO$(C_1-C_6)$-alkyl,
(p) —CO$_2(C_1-C_6)$-alkyl,
(q) —CONR$^8$R$^9$, (r) aryl, which may optionally be substituted with one or more substituents selected from the group consisting of:
1) halo,
2) —OH,
3) $(C_1-C_6)$-alkyl,
4) $(C_1-C_4)$-perfluoroalkyl,
5) $(C_2-C_6)$-alkenyl,
6) $(C_2-C_6)$-alkynyl,
7) $(C_1-C_6)$-alkyloxy,
8) $(C_1-C_6)$-alkyl-$S(O)_n$—,
9) cyano,
10) —COOH,
11) —CO$(C_1-C_6)$-alkyl,
12) —CO$_2(C_1-C_6)$-alkyl,
13) —CONR$^8$R$^9$,
14) —NR$^8$R$^9$,
15) —O(C=O)—$(C_1-C_6)$-alkyl, and
16) —O(C=O)NR$^8$R$^9$, (s) heteroaryl optionally substituted with one or more substituents selected from the group consisting of:
1) halo,
2) —OH,
3) $(C_1-C_6)$-alkyl,
4) $(C_1-C_4)$-perfluoroalkyl,
5) $(C_2-C_6)$-alkenyl,
6) $(C_2-C_6)$-alkynyl,
7) $(C_1-C_6)$-alkyloxy,
8) $(C_1-C_6)$-alkyl-$S(O)_n$—,
9) cyano,
10) —COOH,
11) —CO$(C_1-C_6)$-alkyl,
12) —CO$_2(C_1-C_6)$-alkyl,
13) —CONR$^8$R$^9$,
14) —NR$^8$R$^9$,
15) —O(C=O)—$(C_1-C_6)$-alkyl, and
16) —O(C=O)NR$^8$R$^9$, (t) heterocyclo other than heteroaryl which is optionally substituted with one or more substituents selected from the group consisting of:
1) halo,
2) —OH,
3) $(C_1-C_6)$-alkyl,
4) $(C_1-C_4)$-perfluoroalkyl,
5) $(C_2-C_6)$-alkenyl,
6) $(C_2-C_6)$-alkynyl,
7) $(C_1-C_6)$-alkyloxy,
8) $(C_1-C_6)$-alkyl-$S(O)_n$—,
9) cyano,
10) —COOH,
11) —CO$(C_1-C_6)$-alkyl,
12) —CO$_2(C_1-C_6)$-alkyl,
13) —CONR$^8$R$^9$,
14) —NR$^8$R$^9$,
15) —O(C=O)—$(C_1-C_6)$-alkyl, and
16) —O(C=O)NR$^8$R$^9$, (u) benzyl-$S(O)_n$—, (v) $(C_2-C_{10})$-alkenyl, which may optionally be substituted with one or more substituents selected from the group consisting of:
1) halo,
2) —OH,
3) $(C_1-C_6)$-alkyloxy,
4) $(C_1-C_6)$-alkyl-$S(O)_n$—,
5) cyano,
6) —COOH,
7) —CO$(C_1-C_6)$-alkyl,
8) —CO$_2(C_1-C_6)$-alkyl,
9) —CONR$^8$R$^9$,
10) —NR$^8$R$^9$,
11) —O(C=O)—$(C_1-C_6)$-alkyl, and
12) —O(C=O)NR$^8$R$^9$, (w) $(C_2-C_{10})$-alkynyl wherein alkynyl is optionally substituted with one or more substituents selected from the group consisting of:
1) halo,
2) —OH,
3) $(C_1-C_6)$-alkyloxy,
4) $(C_1-C_6)$-alkyl-$S(O)_n$—,
5) cyano,
6) —COOH,
7) —CO$(C_1-C_6)$-alkyl,
8) —CO$_2(C_1-C_6)$-alkyl,
9) —CONR$^8$R$^9$, 10) —NR$^8$R$^9$,
11) —O(C=O)—(C$_1$-C$_6$)-alkyl, and
12) —O(C=O)NR$^8$R$^9$,
  (x) —(C$_1$-C$_{10}$)-alkyl, which may optionally be substituted with one or more substituents selected from the group consisting of:
    1) halo,
    2) —OH,
    3) (C$_1$-C$_6$)-alkyloxy,
    4) (C$_1$-C$_6$)-alkyl-S(O)$_n$—,
    5) benzyl-S(O)$_n$—,
    6) cyano,
    7) —COOH,
    8) —CO(C$_1$-C$_6$)-alkyl,
    9) —CO$_2$(C$_1$-C$_6$)-alkyl,
    10) —CONR$^8$R$^9$,
    11) —NR$^8$R$^9$,
    12) —O(C=O)—(C$_1$-C$_6$)-alkyl, and
    13) —O(C=O)NR$^8$R$^9$;
R$^{16}$ and R$^{17}$ are independently:
  (a) aryl, which may optionally be substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_2$-C$_6$)-alkenyl,
    6) (C$_2$-C$_6$)-alkynyl,
    7) (C$_1$-C$_6$)-alkyloxy,
    8) (C$_1$-C$_6$)-alkyl-S(O)$_n$—,
    9) cyano,
    10) —COOH,
    11) —CO(C$_1$-C$_6$)-alkyl,
    12) —CO$_2$(C$_1$-C$_6$)-alkyl,
    13) —CONR$^8$R$^9$,
    14) —NR$^8$R$^9$,
    15) —O(C=O)—(C$_1$-C$_6$)-alkyl, and
    16) —O(C=O)NR$^8$R$^9$,
  (b) heteroaryl optionally substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_2$-C$_6$)-alkenyl,
    6) (C$_2$-C$_6$)-alkynyl,
    7) (C$_1$-C$_6$)-alkyloxy,
    8) (C$_1$-C$_6$)-alkyl-S(O)$_n$—,
    9) cyano,
    10) —COOH,
    11) —CO(C$_1$-C$_6$)-alkyl,
    12) —CO$_2$(C$_1$-C$_6$)-alkyl,
    13) —CONR$^8$R$^9$,
    14) —NR$^8$R$^9$,
    15) —O(C=O)—(C$_1$-C$_6$)-alkyl, and
    16) —O(C=O)NR$^8$R$^9$,
  (c) heterocyclo other than heteroaryl which is optionally substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_2$-C$_6$)-alkenyl,
    6) (C$_2$-C$_6$)-alkynyl,
    7) (C$_1$-C$_6$)-alkyloxy,
    8) (C$_1$-C$_6$)-alkyl-S(O)$_n$—,
    9) cyano,
    10) —COOH,
    11) —CO(C$_1$-C$_6$)-alkyl,
    12) —CO$_2$(C$_1$-C$_6$)-alkyl,
    13) —CONR$^8$R$^9$,
    14) —NR$^8$R$^9$,
    15) —O(C=O)—(C$_1$-C$_6$)-alkyl, and
    16) —O(C=O)NR$^8$R$^9$,
  (d) (C$_2$-C$_{10}$)-alkenyl, which may optionally be substituted with one or more substituents selected from the group consisting of:
    1) halo,
    2) —OH,
    3) (C$_1$-C$_6$)-alkyloxy,
    4) (C$_1$-C$_6$)-alkyl-S(O)$_n$—,
    5) cyano,
    6) —COOH,
    7) —CO(C$_1$-C$_6$)-alkyl,
    8) —CO$_2$(C$_1$-C$_6$)-alkyl,
    9) —CONR$^8$R$^9$,
    10) —NR$^8$R$^9$,
    11) —O(C=O)—(C$_1$-C$_6$)-alkyl, and
    12) —O(C=O)NR$^8$R$^9$,
  (e) (C$_2$-C$_{10}$)-alkynyl wherein alkynyl is optionally substituted with one or more substituents selected from the group consisting of:
    1) halo,
    2) —OH,
    3) (C$_1$-C$_6$)-alkyloxy,
    4) (C$_1$-C$_6$)-alkyl-S(O)$_n$—,
    5) cyano,
    6) —COOH,
    7) —CO(C$_1$-C$_6$)-alkyl,
    8) —CO$_2$(C$_1$-C$_6$)-alkyl,
    9) —CONR$^8$R$^9$,
    10) —NR$^8$R$^9$,
    11) —O(C=O)—(C$_1$-C$_6$)-alkyl, and
    12) —O(C=O)NR$^8$R$^9$,
  (f) —(C$_1$-C$_{10}$)-alkyl, which may optionally be substituted with one or more substituents selected from the group consisting of:
    1) halo,
    2) —OH,
    3) (C$_1$-C$_6$)-alkyloxy,
    4) (C$_1$-C$_6$)-alkyl-S(O)$_n$—,
    5) benzyl-S(O)$_n$—,
    6) cyano,
    7) —COOH,
    8) —CO(C$_1$-C$_6$)-alkyl,
    9) —CO$_2$(C$_1$-C$_6$)-alkyl,
    10) —CONR$^8$R$^9$,
    11) —NR$^8$R$^9$,
    12) —O(C=O)—(C$_1$-C$_6$)-alkyl, and
    13) —O(C=O)NR$^8$R$^9$,
or R$^{16}$ and R$^{17}$ are taken together with the nitrogen to which both are attached to form a 3- to 8-membered ring, which may optionally contain 1-4 heteroatoms selected from N, O, and S and be optionally substituted with one or more R$^{14}$'s;
R$^{18}$ is cyano, —COR$^{16}$ or —SO$_2$R$^{16}$;
R$^{19}$ is:
  (a) hydrogen,
  (b) (C$_1$-C$_6$)-alkyl,
  (c) —CO(C$_1$-C$_6$)-alkyl,
  (d) —CO(C$_1$-C$_6$)-aryl,
  (e) —CO(C$_1$-C$_6$)-heteroaryl,
  (f) —CO$_2$(C$_1$-C$_6$)-alkyl,
  (g) CO$_2$(C$_1$-C$_6$)-aryl, (h) $CO_2(C_1$-$C_6)$-heteroaryl,
(i) —$CONR^8R^9$,
(j) —$S(O)_n$-alkyl,
(k) —$S(O)_n$-aryl,
(l) —$S(O)_n$-heteroaryl, or
(m) —$S(O)_n$—$NR^8R^9$;

$R^{20}$ is independently:
(a) hydrogen,
(b) halo,
(c) —OH,
(d) —$O[(C=O)O_r]_s(C_1$-$C_6)$-alkyl,
(e) —$O[(C=O)O_r]_s(C_2$-$C_6)$-alkenyl,
(f) —$O[(C=O)O_r]_s$aryl,
(g) —$O[(C=O)O_r]_s$heteroaryl,
(h) $(C_1$-$C_6)$-alkyl-$S(O)_n$—,
(i) aryl-$(C_1$-$C_6)$alkyloxy-,
(j) cyano,
(k) nitro,
(l) —$NR^8R^9$,
(m) —$O(CO)NR^8R^9$,
(n) —CHO,
(o) COOH,
(p) —$CO(C_1$-$C_6)$-alkyl,
(q) —$CO_2(C_1$-$C_6)$-alkyl,
(r) —$CONR^8R^9$,
(s) aryl, which may optionally be substituted with one or more substituents selected from the group consisting of:
 1) halo,
 2) —OH,
 3) $(C_1$-$C_6)$-alkyl,
 4) $(C_1$-$C_4)$-perfluoroalkyl,
 5) $(C_2$-$C_6)$-alkenyl,
 6) $(C_2$-$C_6)$-alkynyl,
 7) $(C_1$-$C_6)$-alkyloxy,
 8) $(C_1$-$C_6)$-alkyl-$S(O)_n$—,
 9) cyano,
 10) —COOH,
 11) —$CO(C_1$-$C_6)$-alkyl,
 12) —$CO_2(C_1$-$C_6)$-alkyl,
 13) —$CONR^8R^9$,
 14) —$NR^8R^9$,
 15) —$O(C=O)$—$(C_1$-$C_6)$-alkyl, and
 16) —$O(C=O)NR^8R^9$,
(t) heteroaryl optionally substituted with one or more substituents selected from the group consisting of:
 1) halo,
 2) —OH,
 3) $(C_1$-$C_6)$-alkyl,
 4) $(C_1$-$C_4)$-perfluoroalkyl,
 5) $(C_2$-$C_6)$-alkenyl,
 6) $(C_2$-$C_6)$-alkynyl,
 7) $(C_1$-$C_6)$-alkyloxy,
 8) $(C_1$-$C_6)$-alkyl-$S(O)_n$—,
 9) cyano,
 10) —COOH,
 11) —$CO(C_1$-$C_6)$-alkyl,
 12) —$CO_2(C_1$-$C_6)$-alkyl,
 13) —$CONR^8R^9$,
 14) —$NR^8R^9$,
 15) —$O(C=O)$—$(C_1$-$C_6)$-alkyl, and
 16) —$O(C=O)NR^8R^9$,
(u) heterocyclo other than heteroaryl which is optionally substituted with one or more substituents selected from the group consisting of:
 1) halo,
 2) —OH,
 3) $(C_1$-$C_6)$-alkyl,
 4) $(C_1$-$C_4)$-perfluoroalkyl,
 5) $(C_2$-$C_6)$-alkenyl,
 6) $(C_2$-$C_6)$-alkynyl,
 7) $(C_1$-$C_6)$-alkyloxy,
 8) $(C_1$-$C_6)$-alkyl-$S(O)_n$—,
 9) cyano,
 10) —COOH,
 11) —$CO(C_1$-$C_6)$-alkyl,
 12) —$CO_2(C_1$-$C_6)$-alkyl,
 13) —$CONR^8R^9$,
 14) —$NR^8R^9$,
 15) —$O(C=O)$—$(C_1$-$C_6)$-alkyl, and
 16) —$O(C=O)NR^8R^9$,
(v) benzyl-$S(O)_n$—,
(w) $(C_2$-$C_{10})$-alkenyl, which may optionally be substituted with one or more substituents selected from the group consisting of:
 1) halo,
 2) —OH,
 3) $(C_1$-$C_6)$-alkyloxy,
 4) $(C_1$-$C_6)$-alkyl-$S(O)_n$—,
 5) cyano,
 6) —COOH,
 7) —$CO(C_1$-$C_6)$-alkyl,
 8) —$CO_2(C_1$-$C_6)$-alkyl,
 9) —$CONR^8R^9$,
 10) —$NR^8R^9$,
 11) —$O(C=O)$—$(C_1$-$C_6)$-alkyl, and
 12) —$O(C=O)NR^8R^9$,
(x) $(C_2$-$C_{10})$-alkynyl wherein alkynyl is optionally substituted with one or more substituents selected from the group consisting of:
 1) halo,
 2) —OH,
 3) $(C_1$-$C_6)$-alkyloxy,
 4) $(C_1$-$C_6)$-alkyl-$S(O)_n$—,
 5) cyano,
 6) —COOH,
 7) —$CO(C_1$-$C_6)$-alkyl,
 8) —$CO_2(C_1$-$C_6)$-alkyl,
 9) —$CONR^8R^9$,
 10) —$NR^8R^9$,
 11) —$O(C=O)$—$(C_1$-$C_6)$-alkyl, and
 12) —$O(C=O)NR^8R^9$,
(y) —$(C_1$-$C_{10})$-alkyl, which may optionally be substituted with one or more substituents selected from the group consisting of:
 1) halo,
 2) —OH,
 3) $(C_1$-$C_6)$-alkyloxy,
 4) $(C_1$-$C_6)$-alkyl-$S(O)_n$—,
 5) benzyl-$S(O)_n$—,
 6) cyano,
 7) —COOH,
 8) —$CO(C_1$-$C_6)$-alkyl,
 9) —$CO_2(C_1$-$C_6)$-alkyl,
 10) —$CONR^8R^9$,
 11) —$NR^8R^9$,
 12) —$O(C=O)$—$(C_1$-$C_6)$-alkyl, and
 13) —$O(C=O)NR^8R^9$;

$R^{21}$ is:
(a) $C_1$-$C_{10}$-alkyl optionally substituted with one or more $R^{11}$'s,
(b) $C_3$-$C_8$-cycloalkyl optionally substituted with one or more $R^{11}$'s, (c) aryl optionally substituted with one or more $R^{11}$'s, or (d) heterocyclyl optionally substituted with one or more $R^{11}$'s;

m is 1 to 5;
n is 0 to 3;
p is 1 or 2;
r is 0 to 5; and
s is 0 to 4.

In one embodiment, compounds of formula I are provided wherein $R^1$ is a monocylic aryl ring, for example, phenyl, which may be optionally substituted with one or more $R^{10}$'s.

In another embodiments of the invention, compounds of formula I are provided wherein $R^1$ is a monocylic heterocyclic ring, for example, pyridinyl, which may be optionally substituted with one or more $R^{10}$'s.

In yet another embodiment, compounds of formula I are provided wherein
$R^5$ is

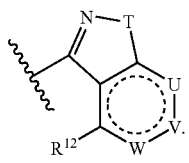

In still yet another embodiment, compounds of formula I are provided wherein $R^5$ is

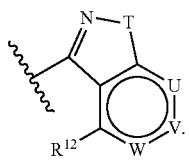

In one embodiment, compounds of formula I are provided wherein T is O, S, C=O, $NR^{19}$ or $CR^{20}$; and U, V, and W are $C(R^{20})_p$. In another embodiment, T is O, S, C=O or $NR^{19}$.

In yet another embodiment, compounds of formula I are provided wherein
$R^5$ is

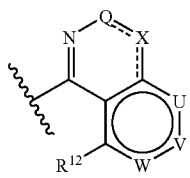

and both Q and X are not C=O.

In still yet another embodiment, compounds of formula I are provided wherein U, V, and W are $(CR^{20})_p$. In one embodiment, Q is C=O and X is O, N or $NR^{19}$. In another embodiment, Q is O or $NR^{19}$ and X is C=O.

In one embodiment, compounds of formula I are provide wherein:
$R^1$ is an aryl or heterocyclic ring, which may be optionally substituted with one or more $R^{10}$'s;
$R^2$ and $R^3$ are independently:
  (a) halo,
  (b) $(C_1-C_6)$-alkoxy optionally substituted with one or more $R^{11}$'s,
  (c) $(C_1-C_4)$-perfluoroalkyl,
  (d) —CO$(C_1-C_6)$-alkyl,
  (e) —CO$_2(C_1-C_6)$-alkyl,
  (f) —CONR$^8$R$^9$,
  (g) —O(CO)NR$^8$R$^9$,
  (h) —NR$^8$(CO)NR$^8$R$^9$,
  (i) —NR$^8$R$^9$,
  (j) hydrogen,
  (k) $C_1$-$C_{10}$-alkyl optionally substituted with one or more $R^{11}$'s,
  (l) aryl optionally substituted with one or more $R^{11}$'s,
  (m) heterocyclyl optionally substituted with one or more $R^{11}$'s, or
  (n) —NR$^8$(CO)OR$^{21}$,
provided that both $R^2$ and $R^3$ are not simultaneously hydrogen;
$R^4$ is:
  (a) hydrogen,
  (b) $C_1$-$C_{10}$-alkyl,
  (c) —CO$(C_1-C_6)$-alkyl,
  (d) —COaryl,
  (e) —COheterocyclyl,
  (f) —CO$_2(C_1-C_6)$-alkyl,
  (g) CO$_2$aryl, or
  (h) CO$_2$heterocyclyl;
$R^5$ is

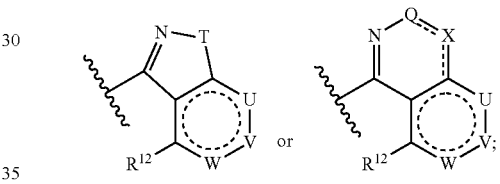

Q is a O, C=O, N, $NR^{19}$ or $C(R^{20})_p$;
T is O, S, C=O, N, $NR^{19}$ or $C(R^{20})_p$;
X, U, V and W are independently O, C=O or $C(R^{20})_p$;
$R^8$ and $R^9$ are independently:
  (a) hydrogen,
  (b) —[(C=O)O$_r$]$_s$aryl, wherein the aryl may be optionally substituted with one or more $R^{14}$'s,
  (c) —[(C=O)O$_r$]$_s$(C$_2$-C$_8$)-alkenyl, wherein the alkenyl may be optionally substituted with one or more $R^{14}$'s,
  (d) —[(C=O)O$_r$]$_s$(C$_1$-C$_8$)alkyl, wherein the alkyl may be optionally substituted with one or more $R^{14}$'s,
  (e) —S(O)$_p$(C$_1$-C$_8$)alkyl, wherein the alkyl may be optionally substituted with one or more $R^{14}$'s,
  (f) heterocyclyl optionally substituted with one or more $R^{14}$'s;
$R^{10}$ is:
  (a) halo,
  (b) —OH,
  (c) —O[(C=O)O$_r$]$_s$(C$_1$-C$_6$)-alkyl,
  (d) —O[(C=O)O$_r$]$_s$(C$_2$-C$_6$)-alkenyl,
  (e) —O[(C=O)O$_r$]$_s$aryl,
  (f) —O[(C=O)O$_r$]$_s$heteroaryl,
  (g) cyano,
  (h) nitro,
  (i) —NR$^8$R$^9$,
  (j) —O(CO)NR$^8$R$^9$,
  (k) —CO(C$_1$-C$_6$)-alkyl,
  (l) —CO$_2$(C$_1$-C$_6$)-alkyl,
  (m) —CONR$^8$R$^9$,
  (n) aryl, which may optionally be substituted with one or more substituents selected from the group consisting of:

1) halo,
2) —OH,
3) ($C_1$-$C_6$)-alkyl,
4) ($C_1$-$C_4$)-perfluoroalkyl,
5) ($C_1$-$C_6$)-alkyloxy,
6) cyano,
7) —CO($C_1$-$C_6$)-alkyl,
8) —$CO_2$($C_1$-$C_6$)-alkyl,
9) —$CONR^8R^9$,
10) —$NR^8R^9$,
11) —O(C=O)—($C_1$-$C_6$)-alkyl, and
12) —O(C=O)$NR^8R^9$, (o) heteroaryl optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy,
6) cyano,
7) —CO($C_1$-$C_6$)-alkyl,
8) —$CO_2$($C_1$-$C_6$)-alkyl,
9) —$CONR^8R^9$,
10) —$NR^8R^9$,
11) —O(C=O)—($C_1$-$C_6$)-alkyl, and
12) —O(C=O)$NR^8R^9$, (p) heterocyclo other than heteroaryl which is optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy,
6) cyano,
7) —CO($C_1$-$C_6$)-alkyl,
8) —$CO_2$($C_1$-$C_6$)-alkyl,
9) —$CONR^8R^9$,
10) —$NR^8R^9$,
11) —O(C=O)—($C_1$-$C_6$)-alkyl, and
12) —O(C=O)$NR^8R^9$, (q) —($C_1$-$C_{10}$)-alkyl, which may optionally be substituted with one or more substituents selected from the group consisting of:
1) halo,
2) —OH,
3) ($C_1$-$C_6$)-alkyloxy,
4) cyano,
5) —CO($C_1$-$C_6$)-alkyl,
6) —$CO_2$($C_1$-$C_6$)-alkyl,
7) —$CONR^8R^9$,
8) —$NR^8R^9$;
9) —O(C=O)—($C_1$-$C_6$)-alkyl, and
10) —O(C=O)$NR^8R^9$;

$R^{11}$ is:
(a) halo,
(b) —OH,
(c) —O[(C=O)$O_r$]$_s$($C_1$-$C_6$)-alkyl,
(d) —O[(C=O)$O_r$]$_s$aryl,
(e) —O[(C=O)$O_r$]$_s$heteroaryl,
(f) cyano,
(g) —$NR^8R^9$,
(h) —O(CO)$NR^8R^9$,
(i) —CO($C_1$-$C_6$)-alkyl,
(j) —$CO_2$($C_1$-$C_6$)-alkyl,
(k) —$CONR^8R^9$, (l) aryl, which may optionally be substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy,
6) cyano,
7) —CO($C_1$-$C_6$)-alkyl,
8) —$CO_2$($C_1$-$C_6$)-alkyl,
9) —$CONR^8R^9$,
10) —$NR^8R^9$,
11) —O(C=O)—($C_1$-$C_6$)-alkyl, and
12) —O(C=O)$NR^8R^9$, (m) heteroaryl optionally substituted with one or more substituents selected from the group consisting of:
1) halo,
2) —OH,
3) ($C_1$-$C_6$)-alkyl,
4) aryl-($C_1$-$C_6$)alkyloxy-,
5) ($C_1$-$C_4$)-perfluoroalkyl,
6) ($C_1$-$C_6$)-alkyloxy,
7) cyano,
8) —CO($C_1$-$C_6$)-alkyl,
9) —$CO_2$($C_1$-$C_6$)-alkyl,
10) —$CONR^8R^9$,
11) —$NR^8R^9$,
12) —O(C=O)—($C_1$-$C_6$)-alkyl, and
13) —O(C=O)$NR^8R^9$, (n) heterocyclo other than heteroaryl which is optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy,
6) cyano,
7) —CO($C_1$-$C_6$)-alkyl,
8) —$CO_2$($C_1$-$C_6$)-alkyl,
9) —$CONR^8R^9$,
10) —$NR^8R^9$,
11) —O(C=O)—($C_1$-$C_6$)-alkyl, and
12) —O(C=O)$NR^8R^9$, (o) —($C_1$-$C_{10}$)-alkyl, which may optionally be substituted with one or more substituents selected from the group consisting of:
1) halo,
2) —OH,
3) ($C_1$-$C_6$)-alkyloxy,
4) cyano,
5) —COOH,
6) —CO($C_1$-$C_6$)-alkyl,
7) —$CO_2$($C_1$-$C_6$)-alkyl,
8) —$CONR^8R^9$,
9) —$NR^8R^9$,
10) —O(C=O)—($C_1$-$C_6$)-alkyl, and
11) —O(C=O)$NR^8R^9$,
(p) —O($CH_2$)$_m$-heteroaryl as defined above;

$R^{12}$ is:
(a) halo,
(b) —OH,
(c) —O[(C=O)$O_r$]$_s$($C_1$-$C_6$)-alkyl,
(d) —O[(C=O)$O_r$]$_s$aryl,
(e) —O[(C=O)$O_r$]$_s$heteroaryl,
(f) cyano,
(g) nitro, (h) —NR$^8$R$^9$,
(i) —O(CO)NR$^8$R$^9$,
(j) —CO(C$_1$-C$_6$)-alkyl,
(k) —CO$_2$(C$_1$-C$_6$)-alkyl,
(l) —CONR$^8$R$^9$,
(m) aryl, which may optionally be substituted with one or more substituents selected from the group consisting of:
  1) halo,
  2) —OH,
  3) (C$_1$-C$_6$)-alkyl,
  4) (C$_1$-C$_4$)-perfluoroalkyl,
  5) (C$_2$-C$_6$)-alkenyl,
  6) (C$_2$-C$_6$)-alkynyl,
  7) (C$_1$-C$_6$)-alkyloxy,
  8) cyano,
  9) —COOH,
  10) —CO(C$_1$-C$_6$)-alkyl,
  11) —CO$_2$(C$_1$-C$_6$)-alkyl,
  12) —CONR$^8$R$^9$,
  13) —NR$^8$R$^9$,
  14) —O(C=O)—(C$_1$-C$_6$)-alkyl, and
  15) —O(C=O)NR$^8$R$^9$,
(n) heteroaryl optionally substituted with one or more substituents selected from the group consisting of:
  1) halo,
  2) —OH,
  3) (C$_1$-C$_6$)-alkyl,
  4) (C$_1$-C$_4$)-perfluoroalkyl,
  5) (C$_1$-C$_6$)-alkyloxy,
  6) cyano,
  7) —COOH,
  8) —CO(C$_1$-C$_6$)-alkyl,
  9) —CO$_2$(C$_1$-C$_6$)-alkyl,
  10) —CONR$^8$R$^9$,
  11) —NR$^8$R$^9$,
  12) —O(C=O)—(C$_1$-C$_6$)-alkyl, and
  13) —O(C=O)NR$^8$R$^9$,
(o) heterocyclo other than heteroaryl which is optionally substituted with one or more substituents selected from the group consisting of:
  1) halo,
  2) —OH,
  3) (C$_1$-C$_6$)-alkyl,
  4) (C$_1$-C$_4$)-perfluoroalkyl,
  5) (C$_1$-C$_6$)-alkyloxy,
  6) cyano,
  7) —CO(C$_1$-C$_6$)-alkyl,
  8) —CO$_2$(C$_1$-C$_6$)-alkyl,
  9) —CONR$^8$R$^9$,
  10) —NR$^8$R$^9$,
  11) —O(C=O)—(C$_1$-C$_6$)-alkyl, and
  12) —O(C=O)NR$^8$R$^9$,
(p) —(C$_1$-C$_{10}$)-alkyl, which may optionally be substituted with one or more substituents selected from the group consisting of:
  1) halo,
  2) —OH,
  3) (C$_1$-C$_6$)-alkyloxy,
  4) cyano,
  5) —CO(C$_1$-C$_6$)-alkyl,
  6) —CO$_2$(C$_1$-C$_6$)-alkyl,
  7) —CONR$^8$R$^9$,
  8) —NR$^8$R$^9$,
  9) —O(C=O)—(C$_1$-C$_6$)-alkyl, and
  10) —O(C=O)NR$^8$R$^9$,
(q) =O;

R$^{14}$ is:
(a) halo,
(b) —OH,
(c) —O[(C=O)O$_r$]$_s$(C$_1$-C$_6$)-alkyl,
(d) —O[(C=O)O$_r$]$_s$aryl,
(e) —O[(C=O)O$_r$]$_s$heteroaryl,
(f) cyano,
(g) nitro,
(h) —NR$^8$R$^9$,
(i) —O(CO)NR$^8$R$^9$,
(j) —CO(C$_1$-C$_6$)-alkyl,
(k) —CO$_2$(C$_1$-C$_6$)-alkyl,
(l) —CONR$^8$R$^9$,
(m) aryl, which may optionally be substituted with one or more substituents selected from the group consisting of:
  1) halo,
  2) —OH,
  3) (C$_1$-C$_6$)-alkyl,
  4) (C$_1$-C$_4$)-perfluoroalkyl,
  5) (C$_1$-C$_6$)-alkyloxy,
  6) cyano,
  7) —CO(C$_1$-C$_6$)-alkyl,
  8) —CO$_2$(C$_1$-C$_6$)-alkyl,
  9) —CONR$^8$R$^9$,
  10) —NR$^8$R$^9$,
  11) —O(C=O)—(C$_1$-C$_6$)-alkyl, and
  12) —O(C=O)NR$^8$R$^9$,
(n) heteroaryl optionally substituted with one or more substituents selected from the group consisting of:
  1) halo,
  2) —OH,
  3) (C$_1$-C$_6$)-alkyl,
  4) (C$_1$-C$_4$)-perfluoroalkyl,
  5) (C$_1$-C$_6$)-alkyloxy,
  6) cyano,
  7) —CO(C$_1$-C$_6$)-alkyl,
  8) —CO$_2$(C$_1$-C$_6$)-alkyl,
  9) —CONR$^8$R$^9$,
  10) —NR$^8$R$^9$,
  11) —O(C=O)—(C$_1$-C$_6$)-alkyl, and
  12) —O(C=O)NR$^8$R$^9$,
(o) heterocyclo other than heteroaryl which is optionally substituted with one or more substituents selected from the group consisting of:
  1) halo,
  2) —OH,
  3) (C$_1$-C$_6$)-alkyl,
  4) (C$_1$-C$_4$)-perfluoroalkyl,
  5) (C$_1$-C$_6$)-alkyloxy,
  6) cyano,
  7) —CO(C$_1$-C$_6$)-alkyl,
  8) —CO$_2$(C$_1$-C$_6$)-alkyl,
  9) —CONR$^8$R$^9$,
  10) —NR$^8$R$^9$,
  11) —O(C=O)—(C$_1$-C$_6$)-alkyl, and
  12) —O(C=O)NR$^8$R$^9$,
(p) —(C$_1$-C$_{10}$)-alkyl, which may optionally be substituted with one or more substituents selected from the group consisting of:
  1) halo,
  2) —OH,
  3) (C$_1$-C$_6$)-alkyloxy,
  4) cyano,
  5) —CO(C$_1$-C$_6$)-alkyl,
  6) —CO$_2$(C$_1$-C$_6$)-alkyl,
  7) —CONR$^8$R$^9$,
  8) —NR$^8$R$^9$, 9) —O(C=O)—($C_1$-$C_6$)-alkyl, and
10) —O(C=O)N$R^8R^9$;

$R^{19}$ is:
(a) hydrogen,
(b) ($C_1$-$C_6$)-alkyl,
(c) —CO($C_1$-$C_6$)-alkyl,
(d) —CO($C_1$-$C_6$)-aryl,
(e) —CO($C_1$-$C_6$)-heteroaryl,
(f) —$CO_2$($C_1$-$C_6$)-alkyl,
(g) $CO_2$($C_1$-$C_6$)-aryl,
(h) $CO_2$($C_1$-$C_6$)-heteroaryl, or
(i) —CONR$^8$R$^9$;

$R^{20}$ is:
(a) hydrogen,
(b) halo,
(c) —OH,
(d) —O[(C=O)$O_r$]$_s$($C_1$-$C_6$)-alkyl,
(e) —O[(C=O)$O_r$]$_s$aryl,
(f) —O[(C=O)$O_r$]$_s$heteroaryl,
(g) cyano,
(h) nitro,
(i) —NR$^8$R$^9$,
(j) —O(CO)NR$^8$R$^9$,
(k) —CO($C_1$-$C_6$)-alkyl,
(l) —$CO_2$($C_1$-$C_6$)-alkyl,
(m) —CONR$^8$R$^9$,
(n) aryl, which may optionally be substituted with one or more substituents selected from the group consisting of:
  1) halo,
  2) —OH,
  3) ($C_1$-$C_6$)-alkyl,
  4) ($C_1$-$C_4$)-perfluoroalkyl,
  5) ($C_1$-$C_6$)-alkyloxy,
  6) cyano,
  7) —CO($C_1$-$C_6$)-alkyl,
  8) —$CO_2$($C_1$-$C_6$)-alkyl,
  9) —CONR$^8$R$^9$,
  10) —NR$^8$R$^9$,
  11) —O(C=O)—($C_1$-$C_6$)-alkyl, and
  12) —O(C=O)NR$^8$R$^9$,
(o) heteroaryl optionally substituted with one or more substituents selected from the group consisting of:
  1) halo,
  2) —OH,
  3) ($C_1$-$C_6$)-alkyl,
  4) ($C_1$-$C_4$)-perfluoroalkyl,
  5) ($C_1$-$C_6$)-alkyloxy,
  6) cyano,
  7) —CO($C_1$-$C_6$)-alkyl,
  8) —$CO_2$($C_1$-$C_6$)-alkyl,
  9) —CONR$^8$R$^9$,
  10) —NR$^8$R$^9$,
  11) —O(C=O)—($C_1$-$C_6$)-alkyl, and
  12) —O(C=O)NR$^8$R$^9$,
(p) heterocyclo other than heteroaryl which is optionally substituted with one or more substituents selected from the group consisting of:
  1) halo,
  2) —OH,
  3) ($C_1$-$C_6$)-alkyl,
  4) ($C_1$-$C_4$)-perfluoroalkyl,
  5) ($C_1$-$C_6$)-alkyloxy,
  6) cyano,
  7) —CO($C_1$-$C_6$)-alkyl,
  8) —$CO_2$($C_1$-$C_6$)-alkyl,
  9) —CONR$^8$R$^9$, and
  10) —NR$^8$R$^9$,
(q) —($C_1$-$C_{10}$)-alkyl, which may optionally be substituted with one or more substituents selected from the group consisting of:
  1) halo,
  2) —OH,
  3) ($C_1$-$C_6$)-alkyloxy,
  4) cyano,
  5) —CO($C_1$-$C_6$)-alkyl,
  6) —$CO_2$($C_1$-$C_6$)-alkyl,
  7) —CONR$^8$R$^9$,
  8) —NR$^8$R$^9$,
  9) —O(C=O)—($C_1$-$C_6$)-alkyl, and
  10) —O(C=O)NR$^8$R$^9$;

$R^{21}$ is:
(a) $C_1$-$C_{10}$-alkyl optionally substituted with one or more $R^{11}$'s,
(b) aryl optionally substituted with one or more $R^{11}$'s, or
(c) heterocyclyl optionally substituted with one or more $R^{11}$'s;

m is 1 to 4;
p is 1 or 2;
r is 0 to 4; and
s is 0 to 3.

In another embodiment, compounds of formula I are provided wherein:
$R^1$ is an aryl or heterocyclic ring, which may be optionally substituted with one or more $R^{10}$'s;
$R^2$ and $R^3$ are independently:
(a) halo,
(b) ($C_1$-$C_6$)-alkoxy optionally substituted with one or more $R^{11}$'s,
(c) ($C_1$-$C_4$)-perfluoroalkyl,
(d) hydrogen,
(e) $C_1$-$C_{10}$-alkyl optionally substituted with one or more $R^{11}$'s,
(f) aryl optionally substituted with one or more $R^{11}$'s, or
(g) heterocyclyl optionally substituted with one or more $R^{11}$'s,
provided that both $R^2$ and $R^3$ are not simultaneously hydrogen;

$R^4$ is:
(a) hydrogen,
(b) $C_1$-$C_{10}$-alkyl,
(c) —CO($C_1$-$C_6$)-alkyl,
(d) —CO($C_1$-$C_6$)-aryl, or
(e) —CO($C_1$-$C_6$)-heteroaryl;

$R^5$ is

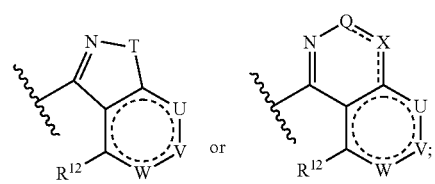

Q is a O, C=O, N, NR$^{19}$ or CR$^{20}$;
T is O, S, C=O, N or NR$^{19}$;
X, U, V and W are independently O, C=O or CR$^{20}$;
$R^8$ and $R^9$ are independently:
(a) hydrogen,
(b) —[(C=O)$O_r$]$_s$aryl, wherein the aryl may be optionally substituted with one or more $R^{14}$'s, (c) —[(C═O)O$_r$]$_s$(C$_1$-C$_8$)alkyl, wherein the alkyl may be optionally substituted with one or more R$^{14}$'s,
(d) heterocyclyl optionally substituted with one or more R$^{14}$'s;
R$^{10}$ is:
  (a) halo,
  (b) —O[(C═O)O$_r$]$_s$(C$_1$-C$_6$)-alkyl,
  (c) —O[(C═O)O$_r$]$_s$aryl,
  (d) —O[(C═O)O$_r$]$_s$heteroaryl,
  (e) cyano,
  (f) nitro,
  (g) aryl, which may optionally be substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy, and
    6) cyano,
  (h) heteroaryl optionally substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy, and
    6) cyano,
  (i) heterocyclo other than heteroaryl which is optionally substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy, and
    6) cyano,
  (j) —(C$_1$-C$_{10}$)-alkyl, which may optionally be substituted with one or more substituents selected from the group consisting of:
    1) halo,
    2) —OH,
    3) (C$_1$-C$_6$)-alkyloxy, and
    4) cyano;
R$^{11}$ is:
  (a) halo,
  (b) —OH,
  (c) —O[(C═O)O$_r$]$_s$(C$_1$-C$_6$)-alkyl,
  (d) —O[(C═O)O$_r$]$_s$aryl,
  (e) —O[(C═O)O$_r$]$_s$heteroaryl,
  (f) —NR$^8$R$^9$, provided that neither R$^8$ nor R$^9$ in this instance is —C(═O)-phenyl,
  (g) —O(CO)NR$^8$R$^9$,
  (h) aryl, which may optionally be substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy, and
    6) cyano,
  (i) heteroaryl optionally substituted with one or more substituents selected from the group consisting of:
    1) halo,
    2) —OH,
    3) (C$_1$-C$_6$)-alkyl,
    4) aryl-(C$_1$-C$_6$)alkyloxy-,
    5) (C$_1$-C$_4$)-perfluoroalkyl,
    6) (C$_1$-C$_6$)-alkyloxy, and
    7) cyano,
  (j) heterocyclo other than heteroaryl which is optionally substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy, and
    6) cyano,
  (k) —(C$_1$-C$_{10}$)-alkyl, which may optionally be substituted with one or more substituents selected from the group consisting of:
    1) halo,
    2) —OH,
    3) (C$_1$-C$_6$)-alkyloxy,
    4) cyano, and
    5) —COOH,
  (l) —O(CH$_2$)$_m$-heteroaryl as defined above;
R$^{12}$ is:
  (a) halo,
  (b) —O[(C═O)O$_r$]$_s$(C$_1$-C$_6$)-alkyl,
  (c) —O[(C═O)O$_r$]$_s$aryl,
  (d) —O[(C═O)O$_r$]$_s$heteroaryl,
  (e) aryl, which may optionally be substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy, and
    6) cyano,
  (f) heteroaryl optionally substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy,
    6) cyano, and
    7) —COOH,
  (g) heterocyclo other than heteroaryl which is optionally substituted with one or more substituents selected from the group consisting of:
    1) halo,
    2) —OH,
    3) (C$_1$-C$_6$)-alkyl,
    4) (C$_1$-C$_4$)-perfluoroalkyl,
    5) (C$_1$-C$_6$)-alkyloxy, and
    6) cyano,
  (h) —(C$_1$-C$_{10}$)-alkyl, which may optionally be substituted with one or more substituents selected from the group consisting of:
    1) halo,
    2) —OH,
    3) (C$_1$-C$_6$)-alkyloxy, and
    4) cyano,
  (i) ═O;
R$^{14}$ is:
  (a) halo,
  (b) —OH,
  (c) —O[(C═O)O$_r$]$_s$(C$_1$-C$_6$)-alkyl,
  (d) —O[(C═O)O$_r$]$_s$aryl,
  (e) —O[(C═O)O$_r$]$_s$heteroaryl,
  (f) aryl, which may optionally be substituted with one or more substituents selected from the group consisting of:

1) halo,
2) —OH,
3) ($C_1$-$C_6$)-alkyl,
4) ($C_1$-$C_4$)-perfluoroalkyl,
5) ($C_1$-$C_6$)-alkyloxy, and
6) cyano,
(g) heteroaryl optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy, and
6) cyano,
(h) heterocyclo other than heteroaryl which is optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy, and
6) cyano,
(i) —($C_1$-$C_{10}$)-alkyl, which may optionally be substituted with one or more substituents selected from the group consisting of:
1) halo,
2) —OH,
3) ($C_1$-$C_6$)-alkyloxy, and
4) cyano;
$R^{19}$ is:
(a) hydrogen,
(b) ($C_1$-$C_6$)-alkyl,
(c) —CO($C_1$-$C_6$)-alkyl,
(d) —$CO_2$($C_1$-$C_6$)-alkyl, or
(e) —$CONR^8R^9$;
$R^{20}$ is:
(a) hydrogen,
(b) halo,
(c) —OH,
(d) —O[(C=O)$O_r$]$_s$($C_1$-$C_6$)-alkyl,
(e) aryl, which may be optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy, and
6) cyano,
(f) heteroaryl optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy, and
6) cyano,
(g) heterocyclo other than heteroaryl which is optionally substituted with one or more substituents selected from the group consisting of:
1) halo,
2) —OH,
3) ($C_1$-$C_6$)-alkyl,
4) ($C_1$-$C_4$)-perfluoroalkyl,
5) ($C_1$-$C_6$)-alkyloxy, and
6) cyano, (h) —($C_1$-$C_{10}$)-alkyl, which may optionally be substituted with one or more substituents selected from the group consisting of:
1) halo,
2) —OH,
3) ($C_1$-$C_6$)-alkyloxy, and
4) cyano;
m is 1 to 3;
r is 0 to 3; and
s is 0 to 2.
In yet another embodiment, compounds of formula I are provided wherein:
$R^1$ is an aryl or heterocyclic ring, which may be optionally substituted with one or more $R^{10}$'s;
$R^2$ and $R^3$ are independently:
(a) hydrogen,
(b) $C_1$-$C_{10}$-alkyl optionally substituted with one or more $R^{11}$'s,
(c) aryl optionally substituted with one or more $R^{11}$'s, or
(d) heterocyclyl optionally substituted with one or more $R^{11}$'s,
provided that both $R^2$ and $R^3$ are not simultaneously hydrogen;
$R^4$ is hydrogen or $C_1$-$C_{10}$-alkyl;
$R^5$ is

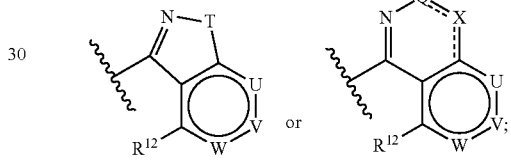

Q is a O, C=O, $NR^{19}$ or $CR^{20}$;
T is O, S, C=O or $NR^{19}$;
X, U, V and W are independently C=O or $CR^{20}$;
$R^8$ and $R^9$ are independently:
(a) hydrogen,
(b) —[(C=O)$O_r$]$_s$aryl,
(c) —[(C=O)$O_r$]$_s$($C_1$-$C_8$)alkyl, or
(d) heterocyclyl;
$R^{10}$ is:
(a) halo,
(b) —O[(C=O)$O_r$]$_s$($C_1$-$C_6$)-alkyl,
(c) —O[(C=O)$O_r$]$_s$heteroaryl,
(d) aryl,
(e) heteroaryl,
(f) heterocyclo, or
(g) —($C_1$-$C_{10}$)-alkyl;
$R^{11}$ is:
(a) —OH,
(b) —O[(C=O)$O_r$]$_s$($C_1$-$C_6$)-alkyl,
(c) —O[(C=O)$O_r$]$_s$aryl,
(d) —O[(C=O)$O_r$]$_s$heteroaryl,
(e) —O(CO)$NR^8R^9$,
(f) aryl,
(g) heteroaryl,
(h) heterocyclo,
(i) —($C_1$-$C_{10}$)-alkyl, or
(j) —O($CH_2$)$_m$-heteroaryl as defined above;
$R^{12}$ is:
(a) halo,
(b) —O[(C=O)$O_r$]$_s$($C_1$-$C_6$)-alkyl,
(c) —O[(C=O)$O_r$]$_s$aryl,
(d) —O[(C=O)$O_r$]$_s$heteroaryl, (e) aryl,
(f) heteroaryl,
(g) heterocyclo,
(h) —($C_1$-$C_{10}$)-alkyl, and
(i) =O;

$R^{19}$ is:
(a) hydrogen,
(b) ($C_1$-$C_6$)-alkyl, or
(c) —$CONR^8R^9$;

$R^2$ is:
(a) hydrogen,
(b) halo,
(c) —O[(C=O)$O_r$]$_s$($C_1$-$C_6$)-alkyl,
(d) aryl,
(e) heteroaryl,
(f) heterocyclo,
(g) —($C_1$-$C_{10}$)-alkyl;

m is 1 to 3;
r is 0 to 3; and
s is 0 to 2.

In one embodiment, compounds of formula I are provided wherein:

$R^1$ is phenyl or pyridinyl, which may be optionally-substituted with one or more $R^{10}$'s;

$R^2$ and $R^3$ are independently:
(a) hydrogen,
(b) $C_1$-$C_{10}$-alkyl optionally substituted with one or more $R^{11}$'s,
(c) aryl optionally substituted with one or more $R^{11}$'s, or
(d) heterocyclyl optionally substituted with one or more $R^{11}$'s, provided that both $R^2$ and $R^3$ are not simultaneously hydrogen;

$R^4$ is hydrogen;
$R^5$ is

[Structures depicted]

Q is a O, C=O or $CR^{20}$;
T is O, S or $NR^{19}$;
X, U, V and W are $CR^{20}$;
$R^8$ and $R^9$ are independently:
(a) hydrogen,
(b) aryl,
(c) ($C_1$-$C_8$)alkyl,
(d) heterocyclyl;

$R^{10}$ is:
(a) halo,
(b) —O($C_1$-$C_6$)-alkyl,
(c) —Oheteroaryl,
(d) aryl,
(e) heteroaryl,
(f) —($C_1$-$C_{10}$)-alkyl;

$R^{11}$ is:
(a) —O($C_1$-$C_6$)-alkyl,
(b) —Oaryl,
(c) —Oheteroaryl,
(d) —O(CO)$NR^8R^9$,
(e) aryl,
(f) heteroaryl,
(g) —($C_1$-$C_{10}$)-alkyl;

$R^{12}$ is:
(a) halo,
(b) —O($C_1$-$C_6$)-alkyl,
(c) —Oaryl,
(d) —Oheteroaryl,
(e) aryl,
(f) heteroaryl,
(g) —($C_1$-$C_{10}$)-alkyl, and
(h) =O;

$R^{19}$ is:
(a) hydrogen,
(b) ($C_1$-$C_6$)-alkyl, or
(c) —$CONR^8R^9$; and $R^{20}$ is:
(a) hydrogen,
(b) halo,
(c) —O($C_1$-$C_6$)-alkyl,
(d) aryl,
(e) heteroaryl,
(f) heterocyclo, or
(g) —($C_1$-$C_{10}$)-alkyl.

In another embodiment, compounds of the present invention are selected from the compounds exemplified in Examples 1 to 72.

Synthesis

Compounds of formula I of may be prepared as shown in the following reaction schemes and description thereof, as well as relevant literature procedures that may be used by one skilled in the art. Exemplary reagents and procedures for these reactions appear hereinafter and in the working examples set forth below.

Compounds of the formula I, where $R^5$ is

[Structure depicted]

T being O or $NR^{19}$, and U, V and W are independently $C(R^{20})_p$ or N, may be prepared using Scheme 1:

SCHEME 1

[Structures depicted: (II) with $NH_2TH$, T = O, $NR^{19}$ → (III) oxidation →]

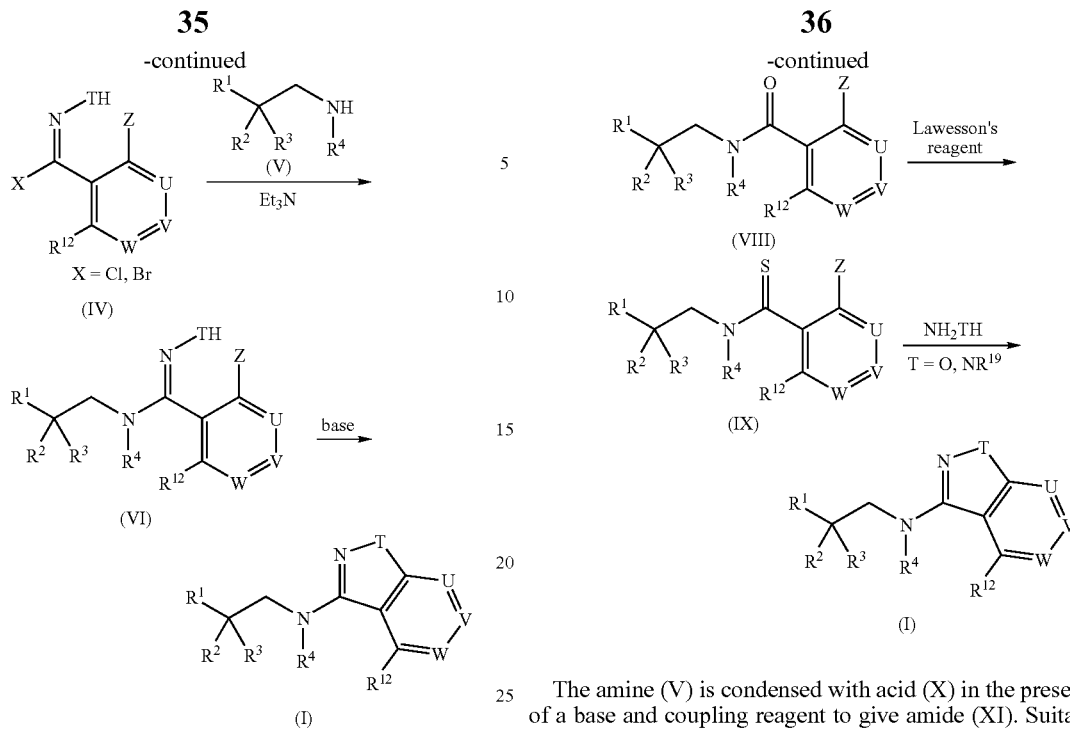

Aldehyde (II) is treated with hydroxylamine or an optionally substituted hydrazine to form (III), which is then oxidized to (IV) using a reagent such as N-chlorosuccimide or bromine. The addition of amine (V) in the presence of a base, such as triethyl amine, gives the coupled product (VI), which undergoes an intramolecular cyclization to give compounds of formula (I). In one embodiment, it may be necessary to induce cyclization of intermediate (VI) using a base, such as potassium t-butoxide or sodium hydride, in a solvent, such as tetrahydrofuran ("THF") or N,N-dimethylformamide ("DMF"), to give compounds of formula (I). Suitable Z substituents for cyclization are leaving groups such as halides (especially fluoro), nitro, hydroxyl and methoxyl groups. (see Fink, D. M; Kurys, B. E. Tetrahedron Lett Vol 37 no 7 pp 995-998, 1196).

Compounds of the formula I, where $R^5$ is

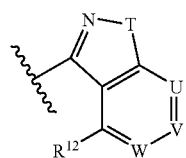

T being O or $NR^{19}$, and U, V and W are independently $C(R^{20})_p$ or N, may be prepared using Scheme 2:

SCHEME 2

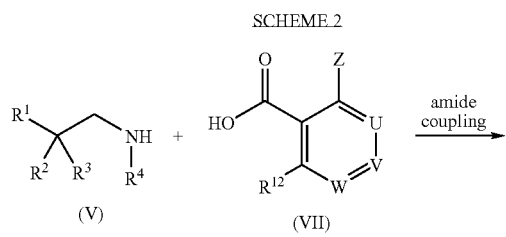

The amine (V) is condensed with acid (X) in the presence of a base and coupling reagent to give amide (XI). Suitable bases that may be used include, but are not limited to, tertiary amines such as triethyl amine. Suitable coupling reagents that may be used include, but are not limited to, any of the coupling reagents commonly used in peptide synthesis, for example, benzotriazol-1-yloxy-tris(dimethylamino)-phosphonium hexafluorophosphate ("BOP reagent"). The amide (XI) is then converted to the thioamide (XII) using Lawesson's reagent. Heating thioamide (XII) in the presence of hydroxylamine or an optionally substituted hydrazine forms compounds of formula (I). Suitable Z substituents for cyclization are leaving groups such as halides (especially fluoro), nitro, hydroxyl and methoxyl groups.

Compounds of the formula I, where $R^5$ is

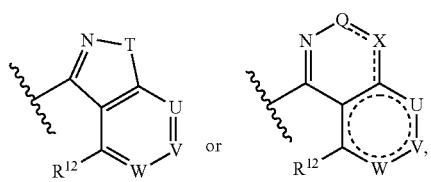

T being S or Q, X are independently N, $NR^{19}$ or $C(R^{20})_p$, and U, V and W are independently $C(R^{20})_p$ or N, may be prepared using Scheme 3:

SCHEME 3

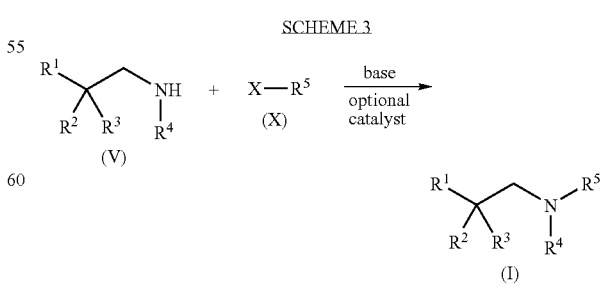

Displacement of a leaving group X (such as halo or triflate) on reagent (X)) by amine (V) results in formation of compounds of formula (I). Conditions may include deprotonation of the amine (V) using a strong base such as n-butyl lithium ("n-BuLi") in an aprotic solvent, such as THF, followed by addition of (X) (see *J. Med. Chem.* 1991, 34, 3316), or the use of a weaker base, such as potassium carbonate ("$K_2CO_3$") in a solvent, such as DMF. Methods of N-arylation of amines such as (V) using substrates such as (X) in the presence of transition metal catalysts, for example, copper and palladium (see Buchwald *J. Org. Chem.* 2000, 65, 1144)), can also be employed.

Compounds of the formula I, where $R^5$ is

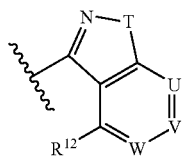

T being C=O, and U, V and W are independently $C(R^{20})_p$ or N, may be prepared using Scheme 4:

SCHEME 4

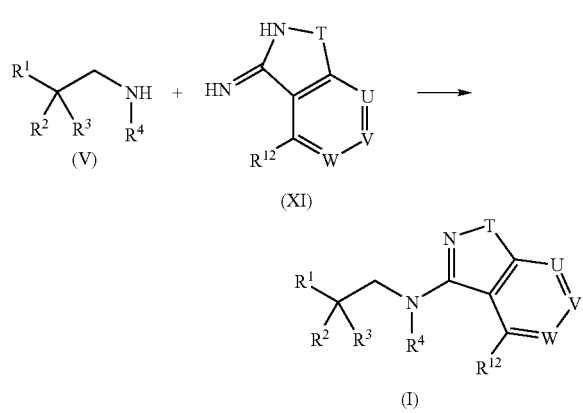

Condensation of the amine (V) with (XI) forms compounds of formula (I).

Compounds of formula (II) are either known compounds or may be prepared by conventional methods known to one of ordinary skill in the art. Examples of suitable methods include, but are not limited to, the methods shown in Scheme 5.

SCHEME 5

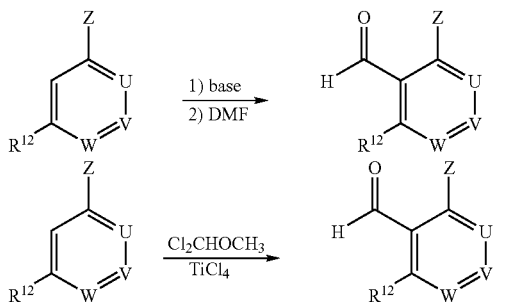

Compounds of formula (V) are either known compounds or may be prepared by conventional methods known to one of ordinary skill in the art. Examples of suitable methods include, but are not limited to, the methods shown in Scheme 6.

SCHEME 6

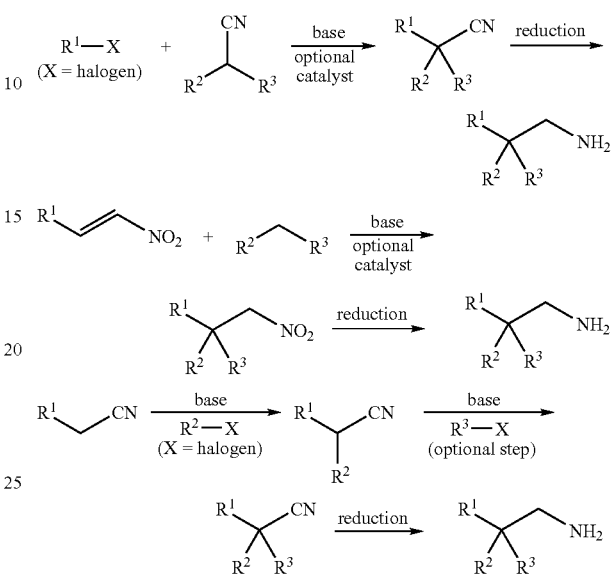

Compounds of formula (VII) are either known compounds or may be prepared by conventional methods known by one of ordinary skill in the art.

Compounds of formula (X) are either known compounds or may be prepared by conventional methods known by one of ordinary skill in the art. Examples of suitable methods include, but are not limited to, the methods shown in Scheme 7.

SCHEME 7

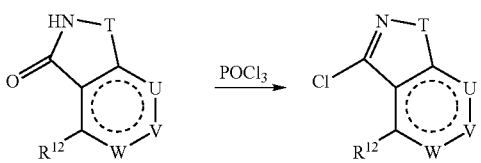

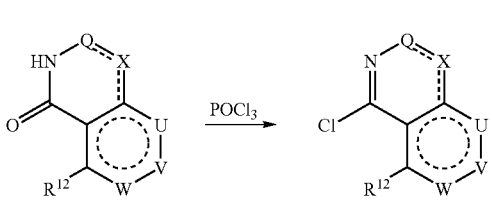

Compounds of formula (XI) may be prepared by conventional methods known to one of ordinary skill in the art. An example of a suitable method includes, but is not limited to, the method shown in Scheme 8.

SCHEME 8

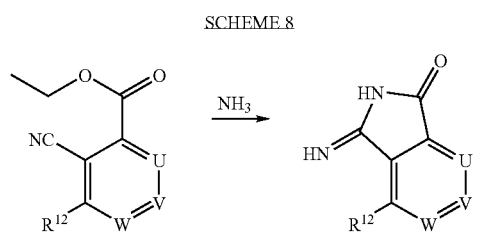

Compounds of formula (I) may also be prepared from other compounds of formula (I) by a variety of interconversion processes.

For example, according to a general interconversion process (IP.1), for compounds of formula (I) in which $R^{20}$ is a potential leaving group (such as halo or triflate), this group can be displaced by nucleophiles (such as alkoxides, amines or metalated variants of organic compounds) in the presence of transition metals when required.

According to another general interconversion process (IP.2), for compounds of formula (I) in which $R^4$=H, this group can be replaced with an alkyl or acyl group by reacting with an alkyl halide (or similar variants) or activated acid (or their variants) respectively, in the presence of an acid or base catalyst when necessary.

According to another general interconversion process (IP.3), for compounds of formula (I) in which $R^{20}$=H, this group can be replaced with a halide, especially chloro using N-chlorosuccinimide, by electrophilic aromatic substitution.

According to another general interconversion process (IP.4), for compounds of formula (I) in which $R^{20}$=H, this group can be replaced with an acyl group by Friedel-Crafts acylation.

According to another general interconversion process (IP.5), for compounds of formula (I) in which $R^{12}$ is —OCH$_3$, this group can be converted to —OH by reaction with boron tribromide.

According to another general interconversion process (IP.6), for compounds of formula (I) in which $R^{19}$=H, this group can be replaced with an alkyl or acyl group by reacting with an alkyl halide (or similar variants) or activated acid (or their variants) respectively, in the presence of an acid or base catalyst when necessary.

According to another general interconversion process (IP.7), for compounds of formula (I) in which Q is $C(R^{20})_p$ and this $R^{20}$=Cl, $R^{20}$ can be converted to —OH by hydrolysis using aqueous acid or to $NR^{19}$ by reaction with $NHR^{19}$ in the presence of a transition metal catalyst when necessary.

According to another general interconversion process (IP.8), for compounds of formula (I) in which T=O, reduction of the N—O bond using conditions such as hydrogenation in the presence of a catalyst followed by cyclization using doubly activated carbonyl source such as 1,1'-carbonyldiimidazole, gives compounds of formula (I) with Q=C=O and X=O.

According to another general interconversion process (IP.9), for compounds of formula (I) in which T=O, reduction of the N—O bond using conditions such as hydrogenation in the presence of a catalyst followed by cyclization using doubly activated sulfonyl source such as 1,1'-sulfonyldiimidazole, gives compounds of formula (I) with Q=SO$_2$ and X=O.

According to another general interconversion process (IP.10), for compounds of formula (I) in which T=C=O, reaction with an optionally substituted hydrazine $NH_2NHR^{19}$ gives compounds of formula (I) in which Q=$NR^{19}$ and X=C=O.

According to another general interconversion process (IP.11), for compounds of formula (I) in which Q=$NR^{19}$ and X=C=O, reaction with a dehydrating agent such as phosphorous oxychloride gives compounds of formula (I) in which Q=$NR^{19}$ and X=$C(R^{20})_p$ where $R^{20}$=Cl.

According to another general interconversion process (IP.11), for compounds of formula (I) in which Q=$NR^{19}$ and X=$C(R^{20})_p$ where $R^{20}$=Cl, this $R^{20}$=Cl may be displaced by nucleophiles (such as alkoxides and amines) to give a different $R^{20}$ or may be reduced by hydrogenation to give compounds where $R^{20}$=H.

During any of the above synthetic sequences it may be necessary to protect certain functional groups at required steps in the sequence. This may be achieved by utilizing protecting group such as those described by T. W. Greene and P. G. M. Wuts in *Protective Groups in Organic Synthesis*, John Wiley & Sons, 1991. The protecting groups may be removed at convenient subsequent steps in the synthesis using methods known in the art.

Utility

Compounds within the scope of the present invention inhibit the $K_v1$ subfamily of voltage-gated K+ channels, and as such are useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esauphagitis, functional dispepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma, chronic obstructive pulmonary disease, cystic fibrosis and atherosclerosis; cell poliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated K+ channels compounds of the present invention are useful to treat a variety of further disorders including resistance by transplantation of organs or tissue, graft-versus-host diseases brought about by medulla ossium transplantation, rheumatoid arthritis, systemic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are antiarrhythmic agents which are useful in the prevention and treatment (including partial alleviation or cure) of arrhythmias. As inhibitors of $K_v1.5$, compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio can also be greater than 4:1, even greater than 10:1. In addition, the ratio may be such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker can provide useful treatment for disorders such as: reflux esauphagitis, functional dispepsia, constipation, asthma, and diabetes. Additionally, $K_v1.5$ is known to be expressed in the anterior pituitary. Thus, administration of an $I_{Kur}$ blocker can stimulate growth hormone secretion. $I_{Kur}$ inhibitors can additionally be useful in cell poliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula I. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, naproxen, celebrex, vioxx and NSAIDs; antiplatelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g. sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; antithrombotic/thrombolytic agents such as tissue plasminogen activator (tPA), recombinant tPA, tenecteplase (TNK), lanoteplase (nPA), factor VIIa inhibitors, factor Xa inhibitors (such as razaxaban), XIa inhibitors, thromin inhibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., questran); antiploliferative agents such as cyclosporin A, taxol, FK 506, and adriamycin; antitumor agents such as taxol, adriamycin, epothilones, cisplatin and carboplatin; anti-diabetic agents such as biguanides (e.g. metformin), glucosidase inhibitors (e.g. acarbose), insulins, meglitinides (e.g. repaglinide), sulfonylureas (e.g. glimepiride, glyburide and glipizide), biguanide/glyburide combinations (i.e., glucovance), thiozolidinediones (e.g. troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g. cilostazol), and PDE V inhibitors (e.g., sildenafil); protein tyrosine kinase inhibitors; steroidal anti-inflammatory agents such as prednisone, and dexamethasone; and other anti-inflammatory agents such as enbrel. The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

Assays to determine the degree of activity of a compound as an $I_{Kur}$ inhibitor are well known in the art and are described in references such as *J. Gen. Physiol.* April; 101(4):513-43, and *Br. J. Pharmacol.* 1995 May; 115(2):267-74.

Assays to determine the degree of activity of a compound as an inhibitor of other members of the $K_v 1$ subfamily are also well known in the art. For example, inhibition of $K_v 1.1$, $K_v 1.2$ and $K_v 1.3$ can be measured using procedures described by Grissmer S, et al., *Mol Pharmacol* 1994 June; 45(6):1227-34. Inhibition of $K_v 1.4$ can be measured using procedures described by Petersen K R, and Nerbonne J M, *Pflugers Arch* 1999 February; 437(3):381-92. Inhibition of $K_v 1.6$ can be measured using procedures described by Bowlby M R, and Levitan I B, *J Neurophysiol* 1995 June; 73(6):2221-9. And inhibition of $K_v 1.7$ can be measured using procedures described by Kalman K, et al., *J Biol Chem* 1998 Mar. 6; 273(10):5851-7.

The following examples further illustrate the present invention, but of course, should not be construed as in any way limiting its scope.

INTERMEDIATES

Intermediate 1

2-Methyl-2-phenylpropaneamine

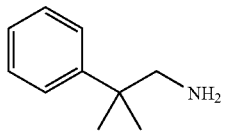

To a stirred solution of 2-methyl-2-phenylpropanenitrile (prepared in a similar manner as the preparation disclosed in *J. Am. Chem. Soc.* 2000, 122, 712; 3.99 g, 27.5 mmol) in anhydrous THF (50 mL) was added a solution of 1.0 molar (M) lithium aluminum hydride in THF (33 mL, 33 mmol). Upon completion of addition, the reaction mixture was heated to reflux where it stirred for 3 hours ("h" or "hr" or "hrs"). Upon completion of this period, the reaction mixture was cooled in an ice bath and then carefully quenched by the addition of 4 normal ("N") sodium hydroxide ("NaOH", ~5 mL) until the resulting effervescences ceased. The reaction mixture was then filtered through a pad of sodium sulfate ("$Na_2SO_4$") and the filter cake was washed with THF. The filtrate was concentrated under reduced pressure to provide Intermediate 1 as a colorless oil (4.1 g, 100%). $^1$H NMR (400 MHz, deuterated chloroform ("CDCl$_3$")) δ ppm 1.31 (s, 6 H), 2.80 (s, 2 H), 7.21 (td, J=5.82, 2.86 Hz, 1 H) 7.31-7.36 (m, 4 H).

Intermediate 2

2-(3-Methoxyphenyl)-2-methylpropan-1-amine

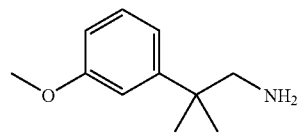

Intermediate 2 was prepared from 2-(3-methoxyphenyl)-2-methylpropanenitrile (prepared in a similar manner as the preparation disclosed in *J. Am. Chem. Soc.* 2000, 122, 712) in a similar manner as described for the preparation of Intermediate 1. $^1$H NMR (400 MHz, CDCl$_3$) δ ppm 1.20 (s, 6 H) 2.70 (s, 2 H) 3.72 (s, 3 H) 6.67 (dd, J=8.13, 2.42 Hz, 1 H) 6.80 (d, J=2.20 Hz, 1 H) 6.84 (d, J=7.03 Hz, 1 H) 7.17 (t, J=8.13 Hz, 1 H).

Intermediate 3

2-(4-Methoxyphenyl)-2-methylpropan-1-amine

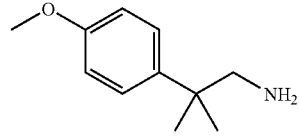

Intermediate 3 was prepared from 2-(4-methoxyphenyl)-2-methylpropanenitrile (prepared in a similar manner as the preparation disclosed in *J. Am. Chem. Soc.* 2000, 122, 712) in a similar manner as described for the preparation of Intermediate 1. $^1$H NMR (400 MHz, CDCl$_3$) δ ppm 1.19 (s, 6 H) 2.67 (s, 2 H) 3.70 (s, 3 H) 6.79 (d, J=8.79 Hz, 2 H) 7.17 (d, J=8.79 Hz, 2 H).

Intermediate 4

2-Methyl-2-(6-methylpyridin-2-yl)propanenitrile

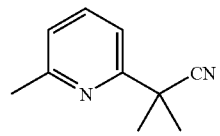

(Intermediate 4 was prepared in a similar manner to the preparation disclosed in *J. Am. Chem. Soc.* 2000, 122, 712). To a stirred solution of 2-fluoro-6-methylpyridine (4.31 g, 38.8 mmol) in toluene (150 mL) was added isobutyronitrile (13.9 mL, 155 mmol) followed by potassium bis(trimethylsilyl)amide (11.7 g, 59 mmol). Upon completion of addition, the reaction was heated to 80° C. for 1 h. After this time, the reaction was cooled to ambient temperature, poured into saturated ("satd") ammonium chloride ("NH$_4$Cl", 100 mL) and then extracted with toluene (2×100 mL). The combined organics were washed with water ("H$_2$O", 100 mL), dried over magnesium sulphate ("Mg$_2$SO$_4$") and filtered. The volatiles were removed under reduced pressure to yield a residue. The residue was subjected to chromatography on silica gel eluting with 5% ethyl acetate ("EtOAc")/hexanes to provide Intermediate 4 as a pale yellow oil (4.91 g, 86%). $^1$H NMR (400 MHz, CDCl$_3$) δ ppm 1.74 (s, 6 H), 2.54 (s, 3 H), 7.07 (d, J=7.91 Hz, 1 H), 7.37 (d, J=7.91 Hz, 1 H), 7.58 (t, J=7.91 Hz, 1 H).

Intermediate 5

2-Methyl-2-(pyridin-2-yl)propanenitrile

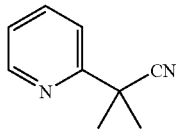

Intermediate 5 was prepared from 2-fluoropyridine and isobutyronitrile in a similar manner as described for the preparation of Intermediate 4. $^1$H NMR (400 MHz, CDCl$_3$) δ ppm 1.65 (s, 6 H) 7.13 (dd, J=7.03, 5.27 Hz, 1 H) 7.47 (d, J=7.91 Hz, 1 H) 7.62 (td, J=7.80, 1.98 Hz, 1 H) 8.49 (d, J=3.95 Hz, 1 H).

Intermediate 6

2-Methyl-2-(5-methylpyridin-2-yl)propanenitrile

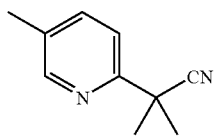

Intermediate 6 was prepared from 2-fluoro-5-methylpyridine and isobutyronitrile in a similar manner as described for the preparation of Intermediate 4. $^1$H NMR (400 MHz, CDCl$_3$) δ ppm 1.46 (s, 6 H) 2.06 (s, 3 H) 7.18-7.21 (m, 1 H) 7.25-7.29 (m, 1 H) 8.13-8.16 (m, 1 H).

Intermediate 7

2-Methyl-2-(6-(trifluoromethyl)pyridin-2-yl)propanenitrile

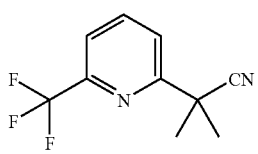

(Intermediate 7 was prepared in a similar manner to the preparation described in *Angew. Chem. Int. Ed.* 2003, 42, 5051). To a stirred solution of bis(dibenzylideneacetone)palladium (0) ("Pd$_2$(dba)$_3$", 100 mg, 0.11 mmol) and potassium t-butoxide (617 mg, 5.5 mmol) in toluene (11 mL) was added 2,8,9-tri-i-butyl-2,5,8,9-tetraza-1-phosphabicyclo[3.3.3]undecane (75 mg, 0.22 mmol) in toluene (2 mL) followed by 2-chloro-6-(trifluoromethyl) pyridine, (500 mg, 2.75 mmol). Upon completion of addition, the reaction mixture was stirred for 20 minutes. After this time, isobutyronitrile (0.30 mL) was added and the resulting mixture was heated at 90° C. for 5 h. Upon completion of this period, the reaction mixture was poured into H$_2$O (20 mL) and extracted with toluene (3×20 mL). The combined extracts were dried over Na$_2$SO$_4$, and filtered. The volatiles were removed under reduced pressure to provide a residue. The residue was subjected to chromatography on silica gel using 0 to 25% EtOAc/hexanes to provide Intermediate 7 as a clear oil. (120 mg, 20%).

Intermediate 8

2-Methyl-2-(6-methylpyridin-2-yl)propan-1-amine

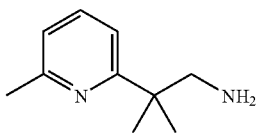

To a stirred solution of Intermediate 4 (2.4 g, 16 mmol) in ethanol (100 mL) was added Raney 2800 nickel (5 mL of slurry in water). Upon completion of addition, the reaction mixture was stirred under hydrogen gas ("H$_2$") at 70 atmospheres ("atm") for 6 h and then filtered through celite. The volatiles were removed under reduced pressure to provide Intermediate 8 as a clear colorless oil (1.83 g, 69%). $^1$H NMR (400 MHz, CDCl$_3$) δ ppm 1.31 (s, 6 H), 2.52 (s, 3 H), 2.92 (s, 2 H), 6.94 (d, J=7.47 Hz, 1 H), 7.09 (d, J=7.91 Hz, 1 H), 7.50 (t, J=7.91 Hz, 1 H).

Intermediate 9

2-Methyl-2-(6-(trifluoromethyl)pyridin-2-yl)propan-1-amine

Intermediate 9 was prepared from Intermediate 7 in a similar manner as described for the preparation of Intermediate 8. m/z (ES⁺) 219 (M+H).

Intermediate 10

2-Methyl-2-(pyridin-2-yl)propan-1-amine

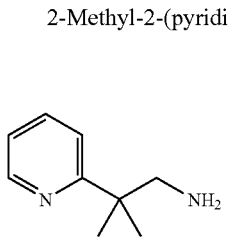

Intermediate 10 was prepared from Intermediate 5 in a similar manner as described for the preparation of Intermediate 8. ¹H NMR (400 MHz, CDCl₃) δ ppm 1.34 (s, 6 H), 2.95 (s, 2 H) 7.09-7.13 (m, 1 H) 7.32 (d, J=7.91 Hz, 1 H) 7.60-7.67 (m, 1 H) 8.58 (d, J=3.52 Hz, 1 H).

Intermediate 11

2-Methyl-2-(5-methylpyridin-2-yl)propan-1-amine

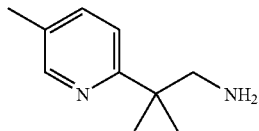

Intermediate 11 was prepared from Intermediate 6 in a similar manner as described for the preparation of Intermediate 8. m/z (ES⁺) 164 (M+H).

Intermediate 12

(+/−)-3-(2-Nitro-1-phenylethyl)pentane-2,4-dione

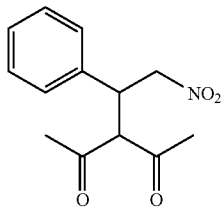

(Intermediate 12 was prepared in a similar manner to the preparation described in *Synthesis* 1982, 467). To a stirred solution of 2,4-pentanedione (2.05 mL, 20 mmol) and β-nitrostyrene (2.98 g, 20 mmol) in chloroform (20 mL) was added nickel(II) acetylacetonate (51 mg, 0.20 mmol). Upon completion of addition, the reaction mixture was heated at 60° C. for 48 h. After this time, the reaction mixture was cooled to ambient temperature and then filtered through celite. The volatiles were removed under reduced pressure to provide a residue. The residue was subjected to chromatography on silica gel eluting with 10 to 40% EtOAc/hexanes to provide Intermediate 12 as a pale yellow solid (1.10 g, 22%). ¹H NMR (400 MHz, CDCl₃) δ ppm 1.92 (s, 3 H), 2.28 (s, 3 H), 4.19-4.23 (m, 1 H), 4.33-4.37 (m, 1 H), 4.57-4.66 (m, 2 H), 7.14-7.18 (m, 2 H), 7.27-7.33 (m, 3 H).

Intermediate 13

(+/−)-3,5-Dimethyl-4-(2-nitro-1-phenylethyl)-1H-pyrazole

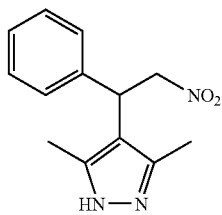

To a suspension of Intermediate 12 (100 mg, 0.40 mmol) in methanol ("MeOH", 3 mL) was added hydrazine monohydrate (21 uL, 0.44 mmol). Upon completion of addition, the reaction mixture was stirred for 16 h. After this time, the volatiles were removed under reduced pressure to provide Intermediate 13 (98 mg, 99%), which was used without further purification. ¹H NMR (400 MHz, CDCl₃) δ ppm 2.19 (s, 6 H), 4.85-4.93 (m, 2 H), 5.06 (dd, J=17.14, 11.43 Hz, 1 H), 7.16 (d, J=7.47 Hz, 2 H), 7.23-7.28 (m, 1 H), 7.33 (t, J=7.25 Hz, 2 H).

Intermediate 14

(+/−)-1,3,5-Trimethyl-4-(2-nitro-1-phenylethyl)-1H-pyrazole

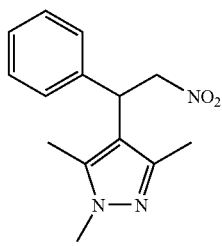

Intermediate 14 was prepared from Intermediate 12 and methylhydrazine in a similar manner as described for the preparation of Intermediate 13. ¹H NMR (400 MHz, CDCl₃) δ ppm 2.13 (s, 3 H), 2.15 (s, 3H), 3.70 (s, 3 H), 4.85-4.93 (m, 2 H), 5.06 (dd, J=17.14, 11.43 Hz, 1 H), 7.16 (d, J=7.47 Hz, 2 H), 7.23-7.28 (m, 1 H), 7.33 (t, J=7.25 Hz, 2 H).

Intermediate 15

(+/−)-3,5-Dimethyl-4-(2-nitro-1-phenylethyl)isoxazole

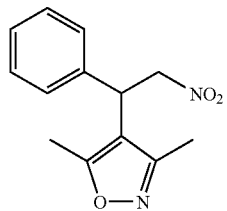

To a suspension of Intermediate 12 (100 mg, 0.40 mmol) in hot t-butyl alcohol ("t-BuOH", 5 mL) was added hydroxylamine hydrochloride (31 mg, 0.44 mmol). Upon completion of addition, the reaction mixture was heated at reflux where it stirred for 3 h. After this time, the reaction mixture was cooled to ambient temperature. Once at the prescribed temperature, the volatiles were removed under reduced pressure to provide a residue. The residue was brought up into EtOAc (25 mL), washed with a satd sodium bicarbonate solution ("NaHCO$_3$", 10 ml) and brine (10 mL), dried over MgSO$_4$, and filtered. Once again, the volatiles were removed under reduced pressure to provide Intermediate 15 as a brown solid (105 mg), which was used without further purification. $^1$H NMR (400 MHz, CDCl$_3$) δ ppm 2.13 (s, 3 H), 2.38 (s, 3H), 4.79-4.90 (m, 2 H), 5.03 (dd, J=11.86, 6.15 Hz, 1 H), 7.14 (d, J=7.03 Hz, 2 H), 7.23-7.28 (m, 1 H), 7.30-7.38 (m, 2 H).

Intermediate 16

(+/−)-2-(3,5-Dimethyl-1H-pyrazol-4-yl)-2-phenylethanamine

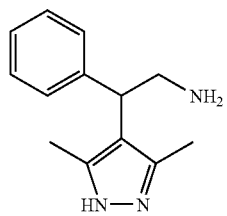

To a stirred solution of Intermediate 13 (98 mg, 0.40 mmol) in methanol (3 mL) was added 10% palladium on carbon (catalytic amount). Upon completion of addition, the reaction mixture was stirred under H$_2$ (1 atm) for 3 days. After this time, the reaction mixture was filtered through celite to provide Intermediate 16, which was used without further purification.

Intermediate 17

(+/−)-2-Phenyl-2-(1,3,5-trimethyl-1H-pyrazol-4-yl)ethanamine

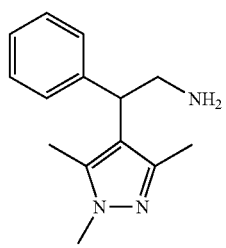

Intermediate 17 was prepared from Intermediate 14 in a similar manner as described for the preparation of Intermediate 16.

Intermediate 18

(+/−)-2-(3,5-Dimethylisoxazol-4-yl)-2-phenylethanamine

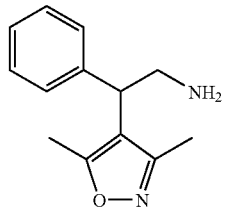

Intermediate 18 was prepared from Intermediate 15 in a similar manner as described for the preparation of Intermediate 16.

Intermediate 19

3,6-Difluoro-2-methoxybenzaldehyde

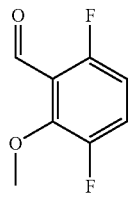

To a stirred solution of 2,5-difluoroanisole (570 mg, 4.0 mmol) in THF (4 mL) at −78° C. was added dropwise a 1.4M solution of secondary butyl lithium ("sec-BuLi") in hexane (3.0 mL, 4.2 mmol). Upon completion of addition, the reaction mixture was stirred for 0.5 h and then DMF (0.38 mL, 4.9 mmol) was added at such a rate as to keep the temperature below −70° C. After addition was complete, the reaction mixture was stirred for 0.5 h and then allowed to warm to ambient temperature over a 0.5 h period. Once at the prescribed temperature, the reaction mixture was quenched by the addition of 3N HCl (6 mL) and then extracted with diethyl ether ("Et$_2$O", 3×30 mL). The combined organics were washed with H$_2$O (15 mL), brine (15 mL), dried over Na$_2$SO$_4$, and filtered. The volatiles were removed under reduced pressure to provide a residue. The residue was subjected to chromatography on silica gel eluting with 0 to 10% EtOAc/hexanes to provide Intermediate 19 as a pale yellow oil (530 mg, 76%). $^1$H NMR (400 MHz, CDCl$_3$) δ ppm 4.01 (s, 3 H), 6.73 (td, J=9.34, 3.30 Hz, 1 H), 7.21 (ddd, J=10.99, 9.23, 4.83 Hz, 1 H), 10.26 (s, 1 H).

Intermediate 20

2-Fluoro-3,6-dimethoxybenzaldehyde

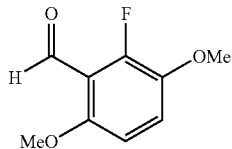

To a stirred solution of 2-fluoro-1,4-dimethoxybenzene (500 mg, 3.2 mmol) in THF (10 mL) at −78° C. was added dropwise a 2.5M solution of n-BuLi in hexane (1.28 mL, 3.2 mmol). The reaction mixtured was stirred for 1 h, and then DMF (0.27 mL, 3.5 mmol) was added at such a rate as to keep the temperature below −70° C. Upon completion of addition, the reaction mixture was stirred for 3 h and then quenched at −78° by addition of a solution of acetic acid ("HOAc") in THF. Water was added and the reaction mixture was extracted with ethyl acetate. The organic extracts were dried over MgSO$_4$, filtered, and the solvent was removed under reduced pressure to provide Intermediate 20 as a yellow solid (518 mg, 88%), which was used without further purification.

Intermediate 21

6-Fluoro-2,3-dimethoxybenzaldehyde

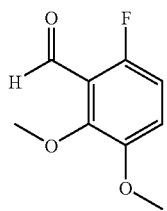

Intermediate 21 was prepared from 4-fluoro-1,2-dimethoxybenzene in a similar manner as described for the preparation of Intermediate 20. $^1$H NMR (400 MHz, CDCl$_3$) δ ppm 3.88 (s, 3 H), 3.98 (s, 3 H), 6.85 (t, J=9.45 Hz, 1 H), 7.09 (dd, J=9.23, 5.27 Hz, 1 H), 10.39 (s, 1 H).

Intermediates 22a and 22b

4-Chloro-2-fluoro-6-methoxybenzaldehyde and 2-chloro-6-fluoro-4-methoxybenzaldehyde

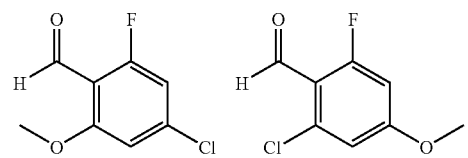

A mixture of intermediates 22a and 22b was prepared from 1-chloro-3-fluoro-5-methoxybenzene in a similar manner as described for the preparation of Intermediate 20.

Intermediate 23

3,5-Dimethoxypyridine

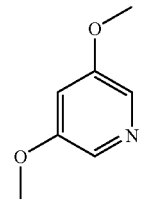

To a vial charged with 2,5-difluoropyridine (127 mg, 1.1 mmol) was added a 25% solution of sodium methoxide in methanol (2 mL). Upon completion of addition, the reaction mixture was heated at 135° C. under microwave conditions for 15 min. At the conclusion of this period, the reaction mixture was diluted with brine (5 mL) and extracted with EtOAc (3×5 mL). The combined extracts were dried over Na$_2$SO$_4$ and filtered. The volatiles were removed under reduced pressure to provide a residue. The residue was subjected to chromatography on silica gel eluting with 0 to 60% EtOAc/hexanes to provide Intermediate 23 as a yellow oil (139 mg, 91%). $^1$H NMR (400 MHz, CDCl$_3$) δ ppm 3.80 (s, 6 H), 6.87 (t, J=2.20 Hz, 1 H), 7.78 (d, J=2.20 Hz, 2 H).

Intermediate 24

3,5-dimethoxyisonicotinaldehyde

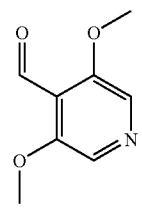

To a stirred solution of lithium diisopropylamide ("LDA", 1.2 mmol) in THF (4 mL) at −78° C. was added a solution of Intermediate 23 (139 mg, 1.0 mmol) at a rate which kept the temperature below −70° C. The reaction mixture was stirred for 30 minutes and then DMF (0.12 mL, 1.5 mmol) was added dropwise. Upon completion of addition, the reaction mixture was stirred for 1 h and then diluted with EtOAc (10 mL). The resulting mixture was washed with satd NaHCO$_3$ (5 mL), brine (5 mL), dried over Na$_2$SO$_4$ and filtered. The volatiles were removed under reduced pressure to provide a residue. The residue was subjected to chromatography on silica gel eluting with 0 to 70% EtOAc/hexanes to provide Intermediate 24 as a pale yellow solid (75 mg, 45%). $^1$H NMR (400 MHz, CDCl$_3$) δ ppm 3.95 (s, 6 H), 8.11 (s, 2 H), 10.44 (s, 1 H).

Intermediate 25

4,6-Dimethoxypyrimidine-5-carbaldehyde

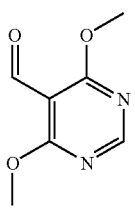

Intermediate 25 was prepared from 4,6-dimethoxypyrimidine in a similar manner as described for the preparation of Intermediate 21. $^1$H NMR (400 MHz, CDCl$_3$) δ ppm 4.09 (s, 6 H), 8.51 (s, 1 H), 10.35 (s, 1 H).

Intermediates 26A and 26B 2,6-Difluoro-4-methoxybenzaldehyde and
2,4-difluoro-6-methoxybenzaldehyde

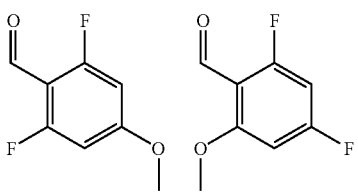

(Intermediates 26A and 26B were prepared in a similar manner to the preparation described in WO 2004046133). To a stirred solution of 3,5-difluoroanisole (1.0 g, 7.0 mmol) in dichloromethane (6 mL) at 0° C. was added dropwise titanium tetrachloride (1.23 mL, 11.2 mmol) and dichloromethyl methyl ether (0.63 mL, 7.0 mmol). Upon completion of addition, the reaction mixture was stirred for 1 h and then poured into ice-water (50 mL). The resulting mixture was extracted with dichloromethane (3×50 mL). The combined organics were washed with H$_2$O (50 mL), brine (50 mL), dried over Na$_2$SO$_4$ and filtered. The volatiles were removed under reduced pressure to provide a residue. The residue was subjected to chromatography on silica gel eluting with 0 to 20% EtOAc/hexanes to give 2,6-difluoro-4-methoxybenzaldehyde, Intermediate 26A [less polar material, 230 mg, 19%, $^1$H NMR (400 MHz, CDCl$_3$) δ ppm 3.85 (s, 3 H), 6.47 (d, J=10.55 Hz, 2 H), 10.17 (s, 1 H)] and 2,4-difluoro-6-methoxybenzaldehyde, Intermediate 26B [more polar material, 740 mg, 62%, $^1$H NMR (400 MHz, CDCl$_3$) δ ppm 3.91 (s, 3 H) 6.43-6.51 (m, 2 H) 10.30 (s, 1 H)], both as white solids.

Intermediate 27

2-Ethyl-6-fluorobenzaldehyde

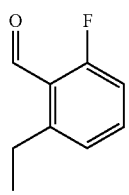

To a vial charged with 2-chloro-6-fluorobenzaldehyde (158 mg, 1.0 mmol), 2,4,6-trivinylcyclotriboroxane pyridine complex (380 mg, 1.0 mmol), tetrakis(triphenylphosphine)palladium(0) (52 mg, 5 mol %) and potassium carbonate (280 mg, 2.0 mmol) was added a 3:1 mixture of 1,2-dimethoxyethane and water-(2 mL). Upon completion of addition, the reaction was heated at 180° C. for 1 h under microwave conditions and then diluted with EtOAc (5 mL). The resulting mixture was washed with satd NaHCO$_3$ (5 mL), dried over Na$_2$SO$_4$ and filtered. The volatiles were removed under reduced pressure to provide crude 2-fluoro-6-vinylbenzaldehyde. The crude 2-fluoro-6-vinylbenzaldehyde was dissolved in methanol (5 mL) and 10% palladium on carbon was added. The resulting reaction mixture was stirred under an atmosphere of H$_2$ for 3 h and then filtered through celite. Once again, the volatiles were removed under reduced pressure to provide Intermediate 27 (approximately 300 mg) as a pale yellow oil, which was used without further purification.

Intermediate 28

5-Methoxyquinazoline-2,4(1H,3H)-dione

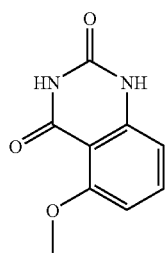

To a suspension of 2-amino-6-methoxybenzoic acid (1.25 g, 7.5 mmol) in a mixture of H$_2$O (45 mL) and acetic acid (0.75 mL) at 35° C. was added a solution of sodium cyanate (1.2 g, 18 mmol) in H$_2$O (5 mL). The reaction mixture was stirred for 0.5 h and then NaOH (13 g, 330 mmol) was added in small portions to provide a precipitate. After cooling to room temperature, the pH of the reaction mixture was adjusted to 7 with concentrated HCl. The resulting precipitate was filtered, washed thoroughly with water and dried in an oven to provide Intermediate 28 as a white solid (1.0 g, 69%)

$^1$H NMR (400 MHz, (CD$_3$)$_2$SO) δ ppm 3.80 (s, 3 H), 6.68-6.71 (m, 2 H), 7.49 (t, J=8.35 Hz, 1 H), 10.88 (s, 1 H), 10.98 (s, 1 H).

Intermediate 29

2,4-Dichloro-5-methoxyquinazoline

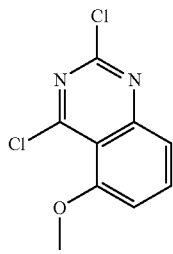

To a flask charged with Intermediate 28 (310 mg, 1.6 mmol) was added phosphorous oxychloride (10 mL) followed by N,N-dimethylaniline (0.2 mL). Upon completion of addition, the reaction mixture was heated at reflux for 4 h. The volatiles were then removed from the reaction mixture under reduced pressure to provide a residue. To the residue was added satd NaHCO$_3$ followed by EtOAc. The organic layer was separated, dried over Na$_2$SO$_4$ and filtered. The volatiles were removed under reduced pressure to provide another residue. This residue was subject to chromatography on silica gel eluting with 10 to 20% EtOAc/hexanes to provide Intermediate 29 as a white solid (180 mg, 49%). $^1$H NMR (400 MHz, CDCl$_3$) δ ppm 4.03 (s, 3 H), 7.02 (d, J=8.35 Hz, 1 H), 7.55 (d, J=8.35 Hz, 1 H), 7.85 (t, J=8.35 Hz, 1 H).

Intermediate 30

(+/−)-4-(benzyloxy)-2-(3-fluorophenyl)butanenitrile

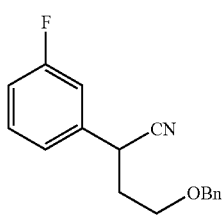

To a stirred solution of 3-fluorophenylacetonitrile (1.0 ml, 8.6 mmol) in toluene (20 ml) at 60° C. was added 50% sodium amide ("NaNH$_2$", 1.0 ml, 13 mmol) in one portion. The resulting solution was stirred for 10 min and then a solution of 2-benzyloxyethyl bromide (1.2 ml, 8.0 mmol) in toluene (20 ml) was added dropwise over a 0.5 h period. Upon completion of addition, the reaction mixture was stirred for an additional 1 h. At the conclusion of this period, the reaction mixture was cooled to ambient temperature and then quenched by adding a few drops of aq. 1N hydrochloric acid ("HCl"). The reaction mixture was then diluted with EtOAc (100 ml) and washed with brine (20 ml×2). The organic layer was separated, dried over MgSO$_4$ and concentrated under reduced pressure to provide an oily mixture. The oily mixture was purified on silica eluting with 0-50% EtOAc/hexanes to provide Intermediate 30 (0.78 g, 2.9 mmol, 36%) as a colorless oil.

Intermediate 31

(+/−)-4-(benzyloxy)-2-(3-fluorophenyl)butan-1-amine

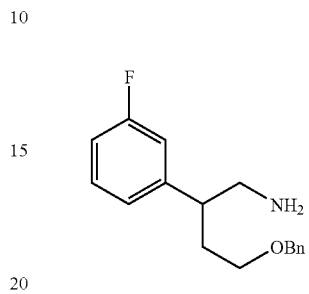

To a stirred solution of Intermediate 30 (3.5 g, 13 mmol) and cobalt(II) chloride hexahydrate ("CoCl$_2$.6H$_2$O", 6.1 g, 26 mmol) in MeOH (50 ml) was added sodium borohydride ("NaBH$_4$", 2.5 g, 65 mmol) in several portions over a 2 h period. The resulting dark solution was stirred for 12 h at 25° C. After this time, the reaction mixture was concentrated under reduced pressure to provide a dark solid. The dark solid was partitioned at aq. ammonium hydroxide ("NH$_4$OH", 50 ml) and EtOAc (200 ml). The aqueous and organic layers were separated and the aqueous layer was further washed with EtOAc (50 ml×2). The organic layers were combined, washed with brine, dried over MgSO$_4$ and concentrated under reduced pressure to provide Intermediate 31 a yellow oil, which was used in the following reaction without further purification.

Intermediate 32

(+/−)-4-amino-3-(3-fluorophenyl)butan-1-ol

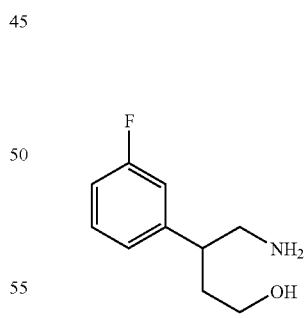

A methanolic solution of Intermediate 31 (0.5 g, 1.8 mmol) was stirred with 10% palladium on carbon ("Pd/C", catalytic amount) under H$_2$ at ambient temperature for 12 h. At the conclusion of this period, the reaction mixture was filtered and concentrated under reduced pressure to provide Intermediate 32 (0.31 g, 94%) as a colorless oil.

Intermediate 33

(+/−)-4-(benzyloxy)-2-phenylbutanenitrile

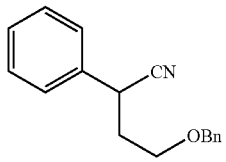

Intermediate 33 was prepared from phenylacetonitrile in a similar manner as described for the preparation of Intermediate 30.

Intermediate 34

(+/−)-4-(benzyloxy)-2-phenylbutan-1-amine

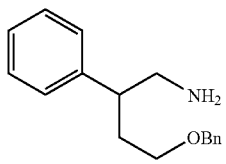

Intermediate 34 was prepared from Intermediate 33 in a similar manner as described for the preparation of Intermediate 31.

Intermediate 35

(+/−)-4-amino-3-phenylbutan-1-ol

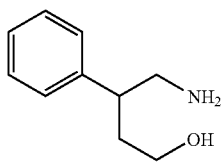

Intermediate 35 was prepared from Intermediate 34 in a similar manner as described for the preparation of Intermediate 32.

Intermediate 36

Methyl 2-amino-3-methoxybenzoate

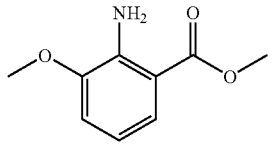

2-amino-3-methoxybenzoic acid (22.8 g, 137 mmol) was suspended in a mixture of benzene (300 mL) and methanol (120 mL) and a 2M solution of TMS-diazomethane in hexane was added dropwise until a yellow color remained and the evolution of nitrogen stopped (~90 mL). The solvent was evaporated to afford Intermediate 36 (25.2 g) as a brown solid which was used with out further purification. $^1$H NMR (400 MHz, CDCl$_3$) δ ppm 3.87 (s, 6 H), 6.01 (bs, 2 H), 6.58 (t, J=7.91 Hz, 1 H), 6.85 (d, J=7.91 Hz, 1 H), 7.47 (d, J=7.91 Hz, 1 H).

Intermediate 37

Methyl 2-cyano-3-methoxybenzoate

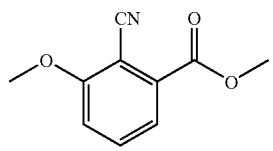

A suspension of methyl-2-amino-3-methoxybenzoate (Intermediate 36, 2.27 g, 12.5 mmol) in water (10 mL) and con. HCl (2 mL) was cooled to 0 deg. C. and a solution of sodium nitrite (1.04 g, 15 mmol) in water (10 mL) was added dropwise. The resulting solution was stirred cold for 30 min. then added to a suspension of copper(I)cyanide (3.4 g, 38 mmol) in water (100 mL). The resulting suspension was heated at 60 deg. C. for 3 h, cooled, chloroform was added and the mixture was filtered through celite. The organic layer was dried (MgSO4), the solvent was evaporated and the residue was flash chromatographed eluting with 0-50% hexane-ethyl acetate affording Intermediate 37 (0.56 g, 23.5%) as a yellow solid. $^1$H NMR (400 MHz, CDCl$_3$) δ ppm 3.99 (s, 6 H), 7.20 (d, J=8.35 Hz, 1 H), 7.61 (t, J=8.13 Hz, 1 H), 7.68 (d, J=7.47 Hz, 1 H).

Intermediate 38

3-Imino-4-methoxyisoindolin-1-one

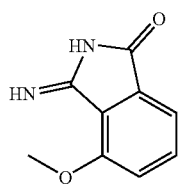

A suspension of methyl-2-cyano-3-methoxybenzoate (Intermediate 37, 570 mg, 2.98 mmol) in methanol (20 mL) was saturated with anhydrous ammonia and stirred for three days. The solvent was evaporated to give Intermediate 38 (430 mg, 97%) as a yellow solid which was used without further purification. $^1$H NMR (400 MHz, (CD$_3$)$_2$SO)) δ ppm 3.88 (s, 3 H), 7.19 (d, J=7.47 Hz, 1 H), 7.29 (d, J=8.35 Hz, 1 H), 7.56 (t, J=7.91 Hz, 1 H), 8.55-8.78 (bs, 1H), 10.28-10.55 (bs, 1H).

EXAMPLES

Example 1

4-Methoxy-N-(2-methyl-2-phenylpropyl)benzo[d]isoxazol-3-amine

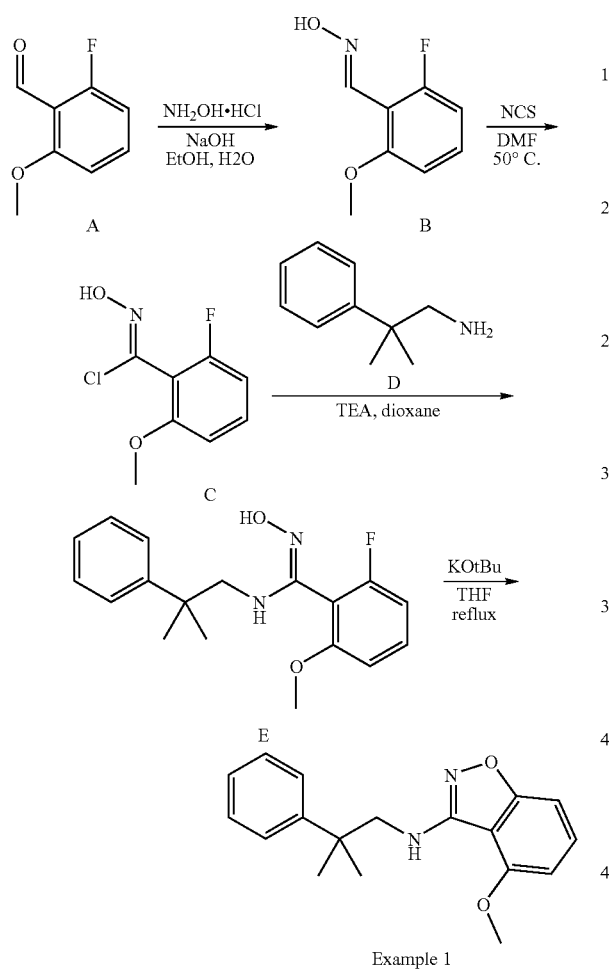

Example 1

Compound B: To a flask charged with 2-fluoro-6-methoxylbenzaldehyde (Compound A, 2.43 g, 15.8 mmol) and hydroxylamine hydrochloride ("NH₂OH.HCl", 1.2 g, 17.3 mmol) in ethanol (60 mL) and H₂O (120 mL) was added-aq. NaOH (50% w/w 3.2 mL). The reaction mixture was stirred at room temperature for 1 hour. At the conclusion of this period, the reaction was neutralized with concentrated HCl to pH 7 and then extracted with methylene chloride ("CH$_2$Cl$_2$", 3×200 mL). The combined organic layers were washed with brine (100 mL), dried over Na$_2$SO$_4$ and filtered. The volatiles were removed under reduced pressure to provide 2-fluoro-6-methoxybenzaldehyde oxime, Compound B, as a white solid (2.45 g, 92%). m/z (ES$^+$) 169 (M+H).

Compound C: A portion of Compound B (100 mg, 0.59 mmol) was dissolved in DMF (2.5 mL) and then N-chlorosuccinimide (79 mg, 0.59 mmol) was added. Upon completion of addition, the reaction mixture was heated at 50° C. for 30 minutes. At the conclusion of this period, the reaction mixture was over ice and then diluted with EtOAc (15 mL). The resulting mixture was washed with H$_2$O (3×8 mL) and brine (8 mL), dried over Na$_2$SO$_4$ and filtered. The volatiles were removed under reduced pressure to provide a residue containing 2-fluoro-6-methoxybenzoyl chloride oxime, Compound C, as a clear oil (133 mg).

Compound E: The residue containing Compound C was taken up in anhydrous 1,4-dioxane (2 mL) and then a solution of Intermediate 1 (Compound D, 88 mg, 0.59 mmol) in 1,4-dioxane (1 mL) was added followed by triethylamine (90 μL, 0.65 mmol). The reaction was stirred at room temperature overnight and then diluted with H$_2$O (2 mL). The resulting mixture was extracted with Et$_2$O (3×5 mL), and the combined organic layers were dried over Na$_2$SO$_4$ and filtered. The volatiles were removed under reduced pressure to provide a residue. The residue was subjected to chromatography on silica gel eluting with 20 to 100% EtOAc/hexanes to provide 2-fluoro-N'-hydroxy-6-methoxy-N-(2-methyl-2-phenylpropyl)benzamidine, Compound E, as clear oil (135 mg, 72% for 2 steps). $^1$H NMR (400 MHz, CDCl$_3$) δ ppm 1.25 (s, 6 H), 3.00 (d, J=6.15 Hz, 2 H), 3.83 (s, 3 H), 5.23 (t, J=6.15 Hz, 1 H), 6.68-6.77 (m, 2 H), 7.19-7.24 (m, 1 H) 7.29-7.38 (m, 5 H).

Example 1: To a solution of Compound E (135 mg, 0.43 mmol) in THF (4 mL) was added potassium tert-butoxide (53 mg, 0.47 mmol). The reaction was heated at reflux for 2 hours and then allowed to cool to ambient temperature. Once at the prescribed temperature, the reaction mixture was diluted with H$_2$O (4 mL) and extracted with EtOAc (3×8 mL). The combined organic layers were dried over Na$_2$SO$_4$ and filtered. The volatiles were removed under reduced pressure to provide a residue. The residue was subjected to chromatography in silica gel eluting with 0% to 40% EtOAc/hexanes to provide Example 1 as a clear oil (105 mg, 83%). $^1$H NMR (400 MHz, CDCl$_3$) δ ppm 1.46 (s, 6 H), 3.54 (d, J=6.15 Hz, 2 H), 3.74 (s, 3 H), 4.66 (t, J=5.49 Hz, 1 H), 6.43 (d, J=7.91 Hz, 1 H), 6.91 (d, J=8.35 Hz, 1 H), 7.24-7.33 (m, 2 H), 7.38 (t, J=7.69 Hz, 2 H), 7.44-7.47 (m, 2 H).

Example 2

(R)-4-Methoxy-N-(2-phenylpropyl)benzo[d]isoxazol-3-amine

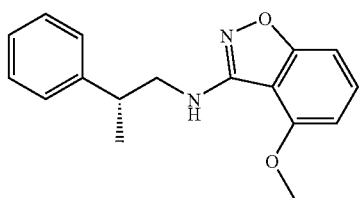

Example 2 was prepared from 2-fluoro-6-methoxylbenzaldehyde and (R)-2-phenylpropan-1-amine in a similar manner as described for the preparation of Example 1. $^1$H NMR (400 MHz, CDCl$_3$) δ ppm 1.37 (d, J=7.03 Hz, 3 H), 3.16-3.25 (m, 1 H), 3.42 (ddd, J=12.74, 8.57, 3.74 Hz, 1 H), 3.60-3.67 (m, 1 H), 3.79 (s, 3 H), 4.87 (bs, 1 H), 6.46 (d, J=7.91 Hz, 1 H), 6.93 (d, J=8.35 Hz, 1 H) 7.24-7.33 (m, 6 H).

Example 3

(S)-4-Methoxy-N-(2-phenylpropyl)benzo[d]isoxazol-3-amine

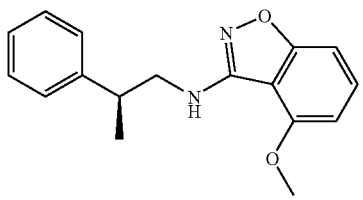

Example 3 was prepared from 2-fluoro-6-methoxylbenzaldehyde and (S)-2-phenylpropan-1-amine in a similar manner as described for the preparation of Example 1. $^1$H NMR (400 MHz, CDCl$_3$) δ ppm 1.37 (d, J=7.03 Hz, 3 H), 3.16-3.25 (m, 1 H), 3.42 (ddd, J=12.74, 8.57, 3.74 Hz, 1 H), 3.60-3.67 (m, 1 H), 3.79 (s, 3 H), 4.87 (bs, 1 H), 6.46 (d, J=7.91 Hz, 1 H), 6.93 (d, J=8.35 Hz, 1 H) 7.24-7.33 (m, 6 H).

Example 4

(+/−)-N-(2-(4-chlorophenyl)propyl)-4-methoxybenzo[d]isoxazol-3-amine

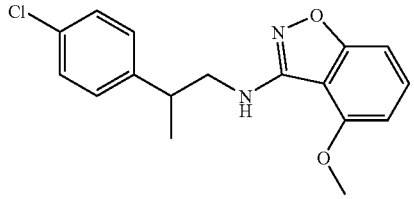

Example 4 was prepared from 2-fluoro-6-methoxylbenzaldehyde and (+/−)-2-(4-chlorophenyl)propan-1-amine in a similar manner as described for the preparation of Example 1. $^1$H NMR (400 MHz, CDCl$_3$) δ ppm 1.33 (d, J=7.03 Hz, 3 H) 3.21 (dq, J=7.25, 7.10 Hz, 1 H) 3.38 (ddd, J=12.85, 8.46, 4.17 Hz, 1 H) 3.59 (ddd, J=12.96, 6.81, 6.59 Hz, 1 H) 3.81 (s, 3 H) 4.84 (bs, 1 H) 6.46 (d, J=7.91 Hz, 1 H) 6.92 (d, J=8.35 Hz, 1 H) 7.17-7.34 (m, 5 H).

Example 5

(+/−)-4-Methoxy-N-(2-phenyl-2-(1,3,5-trimethyl-1H-pyrazol-4-yl)ethyl)benzo[d]isoxazol-3-amine

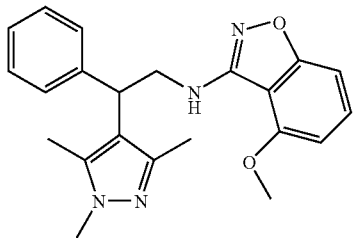

Example 5 was prepared from 2-fluoro-6-methoxylbenzaldehyde and Intermediate 17 in a similar manner as described for the preparation of Example 1. $^1$H NMR (400 MHz, CDCl$_3$) δ ppm 2.00 (s, 3 H), 2.08 (s, 3 H), 3.66 (s, 3 H), 3.69-3.78 (m, 1 H), 3.77 (s, 3 H), 4.04-4.11 (m, 1 H), 4.34 (dd, J=9.23, 6.59 Hz, 1 H), 4.89 (dd, J=6.59, 4.83 Hz, 1 H), 6.42 (d, J=7.91 Hz, 1 H), 6.89 (d, J=8.35 Hz, 1 H), 7.15 (t, J=6.81 Hz, 1 H), 7.19-7.30 (m, 5 H).

Example 6

(+/−)-N-(2-(3,5-dimethyl-1H-pyrazol-4-yl)-2-phenylethyl)-4-methoxybenzo[d]isoxazol-3-amine

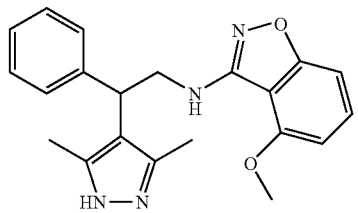

Example 6 was prepared from 2-fluoro-6-methoxylbenzaldehyde and Intermediate 16 in a similar manner as described for the preparation of Example 1. $^1$H NMR (400 MHz, CDCl$_3$) δ ppm 2.17 (s, 6 H), 3.79-3.87 (m, 1 H), 3.82 (s, 3 H), 4.12 (ddd, J=12.96, 6.81, 6.59 Hz, 1 H), 4.45 (dd, J=8.79, 7.03 Hz, 1 H), 4.94 (bt, J=5.71 Hz, 1 H), 6.48 (d, J=7.91 Hz, 1 H), 6.95 (d, J=8.35 Hz, 1 H), 7.19-7.36 (m, 6 H).

Example 7

(+/−)-N-(2-(3,5-dimethylisoxazol-4-yl)-2-phenylethyl)-4-methoxybenzo[d]isoxazol-3-amine

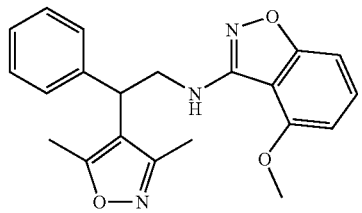

Example 7 was prepared from 2-fluoro-6-methoxylbenzaldehyde and Intermediate 18 in a similar manner as described for the preparation of Example 1. $^1$H NMR (400 MHz, CDCl$_3$) δ ppm 2.06 (s, 3 H), 2.31 (s, 3 H), 3.80-3.87 (m, 1 H), 3.84 (s, 3 H), 4.10 (dt, J=13.18, 6.59 Hz, 1 H), 4.37-4.42 (m, 1 H), 4.94 (t, J=5.71 Hz, 1H), 6.50 (d, J=7.91 Hz, 1 H), 6.96 (d, J=8.35 Hz, 1 H), 7.22-7.28 (m, 3 H), 7.30-7.38 (m, 3 H).

Example 8

4-Methoxy-N-(2-(3-methoxyphenyl)-2-methylpropyl)benzo[d]isoxazol-3-amine

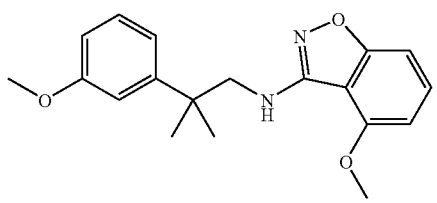

Example 8 was prepared from 2-fluoro-6-methoxylbenzaldehyde and Intermediate 2 in a similar manner as described for the preparation of Example 1. $^1$H NMR (400 MHz, CDCl$_3$) δ ppm 1.37 (s, 6 H), 3.44 (d, J=5.71 Hz, 2 H), 3.69 (s, 3 H), 3.76 (s, 3 H), 4.63 (t, J=5.49 Hz, 1 H), 6.37 (d, J=7.91 Hz, 1 H), 6.74 (dd, J=7.91, 2.20 Hz, 1 H), 6.84 (d, J=8.35 Hz, 1 H), 6.93 (t, J=1.98 Hz, 1 H), 6.97 (d, J=7.91 Hz, 1 H), 7.19-7.24 (m, 2 H).

Example 9

4-Methoxy-N-(2-(4-methoxyphenyl)-2-methylpropyl)benzo[d]isoxazol-3-amine

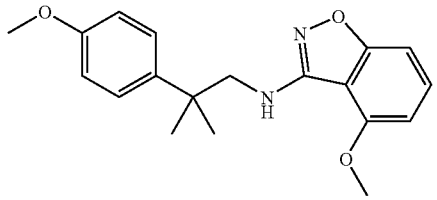

Example 9 was prepared from 2-fluoro-6-methoxylbenzaldehyde and Intermediate 3 in a similar manner as described for the preparation of Example 1. $^1$H NMR (400 MHz, CDCl$_3$) δ ppm 1.36 (s, 6 H), 3.43 (d, J=6.15 Hz, 2 H), 3.70 (s, 3 H), 3.75 (s, 3 H), 4.61 (t, J=5.49 Hz, 1 H), 6.37 (d, J=8.35 Hz, 1 H), 6.83-6.87 (m, 3 H), 7.24 (t, J=8.13 Hz, 1 H), 7.28-7.32 (m, 2 H).

Example 10

4-Methoxy-N-(2-methyl-2-(pyridin-2-yl)propyl)benzo[d]isoxazol-3-amine

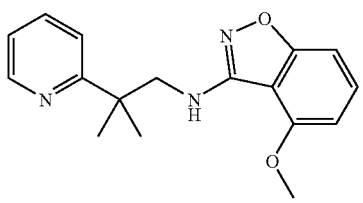

Example 10 was prepared from 2-fluoro-6-methoxylbenzaldehyde and Intermediate 10 in a similar manner as described for the preparation of Example 1. $^1$H NMR (400 MHz, CDCl$_3$) δ ppm 1.46 (s, 6 H), 3.65 (d, J=6.15 Hz, 2 H), 3.86 (s, 3 H), 5.99 (t, J=5.49 Hz, 1 H), 6.46 (d, J=7.91 Hz, 1 H), 6.90 (d, J=8.35 Hz, 1 H), 7.15 (dd, J=7.03, 5.27 Hz, 1 H), 7.26-7.32 (m, 1 H), 7.38 (d, J=8.35 Hz, 1 H), 7.66 (td, J=7.80, 1.98 Hz, 1 H), 8.59 (d, J=3.95 Hz, 1 H).

Example 11

4-Methoxy-N-(2-methyl-2-(5-methylpyridin-2-yl)propyl)benzo[d]isoxazol-3-amine

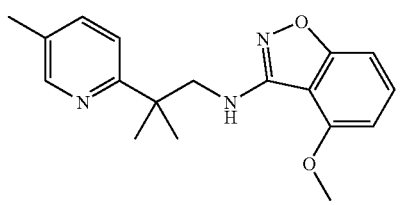

Example 11 was prepared from 2-fluoro-6-methoxylbenzaldehyde and Intermediate 11 in a similar manner as described for the preparation of Example 1. $^1$H NMR (400 MHz, CDCl$_3$) δ ppm 1.43 (s, 6 H), 2.31 (s, 3 H), 3.60 (d, J=5.71 Hz, 2 H), 3.86 (s, 3 H), 6.00 (t, J=5.49 Hz, 1 H), 6.45 (d, J=8.35 Hz, 1 H), 6.89 (d, J=8.35 Hz, 1H), 7.24-7.31 (m, 2 H), 7.46 (dd, J=8.35, 2.20 Hz, 1 H), 8.40 (d, J=2.20 Hz, 1 H).

Example 12

4-Methoxy-N-(2-methyl-2-(6-methylpyridin-2-yl)propyl)benzo[d]isoxazol-3-amine

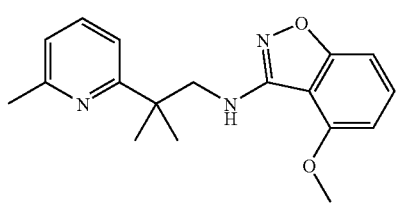

Example 12 was prepared from 2-fluoro-6-methoxylbenzaldehyde and Intermediate 8 in a similar manner as described for the preparation of Example 1. $^1$H NMR (400 MHz, CDCl$_3$) δ ppm 1.44 (s, 6 H), 2.60 (s, 3 H), 3.63 (d, J=6.15 Hz, 2 H), 3.91 (s, 3 H), 6.37 (t, J=5.27 Hz, 1 H), 6.50 (d, J=7.91 Hz, 1 H), 6.93 (d, J=8.35 Hz, 1 H), 7.00 (d, J=7.47 Hz, 1 H), 7.16 (d, J=7.91 Hz, 1 H), 7.32 (t, J=8.13 Hz, 1 H), 7.55 (t, J=7.69 Hz, 1 H).

Example 13

4-Methoxy-N-(2-methyl-2-(6-(trifluoromethyl)pyridin-2-yl)propyl)benzo[d]isoxazol-3-amine

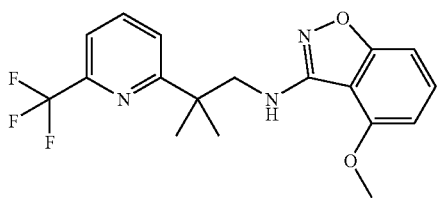

Example 13 was prepared from 2-fluoro-6-methoxybenzaldehyde and Intermediate 9 in a similar manner as described for the preparation of Example 1. $^1$H NMR (400 MHz, CDCl$_3$) δ ppm 1.48 (s, 6 H) 3.76 (d, J=6.15 Hz, 2 H) 3.86 (s, 3 H) 5.85 (t, J=6.15 Hz, 1 H) 6.48 (d, J=7.91 Hz, 1 H) 6.92 (d, J=8.35 Hz, 1 H) 7.32 (t, J=8.13 Hz, 1 H) 7.55 (d, J=7.47 Hz, 1 H) 7.59 (d, J=7.91 Hz, 1 H) 7.85 (t, J=7.91 Hz, 1 H).

Example 14

7-Fluoro-4-methoxy-N-(2-methyl-2-phenylpropyl)benzo[d]isoxazol-3-amine

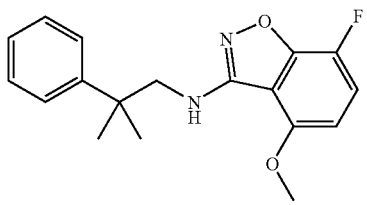

Example 14 was prepared from 2,3-difluoro-6-methoxybenzaldehyde and Intermediate 1 in a similar manner as described for the preparation of Example 1. $^1$H NMR (400 MHz, CDCl$_3$) δ ppm 1.37 (s, 6 H), 3.45 (d, J=6.15 Hz, 2 H), 3.63 (s, 3 H), 4.60 (t, J=5.71 Hz, 1 H), 6.21 (dd, J=8.79, 2.20 Hz, 1 H), 6.90-6.96 (m, 1 H), 7.16-7.21 (m, 1 H), 7.31 (t, J=7.69 Hz, 2 H), 7.34-7.39 (m, 2 H).

Example 15

6-Fluoro-4-methoxy-N-(2-methyl-2-phenylpropyl)benzo[d]isoxazol-3-amine

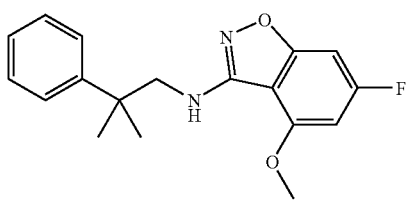

Example 15 was prepared from Intermediate 26B and Intermediate 1 in a similar manner as described for the preparation of Example 1. $^1$H NMR (400 MHz, CDCl$_3$) δ ppm 1.44 (s, 6 H), 3.50 (d, J=5.71 Hz, 2 H), 3.72 (s, 3 H), 4.50-4.57 (m, 1H), 6.22 (dd, J=10.99, 1.76 Hz, 1 H), 6.61 (dd, J=8.35, 1.76 Hz, 1 H), 7.24-7.28 (m, 1 H), 7.38 (t, J=7.69 Hz, 2 H), 7.42-7.46 (m, 2 H).

Example 16

4-Fluoro-6-methoxy-N-(2-methyl-2-phenylpropyl)benzo[d]isoxazol-3-amine

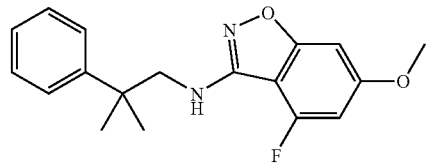

Example 16 was prepared from Intermediate 26A and Intermediate 1 in a similar manner as described for the preparation of Example 1. $^1$H NMR (400 MHz, CDCl$_3$) ppm 1.38 (s, 6 H), 3.48 (d, J=6.15 Hz, 2 H), 3.75 (s, 6 H), 4.03 (bs, 1 H), 6.31 (dd, J=11.42, 1.76 Hz, 1 H), 6.53 (d, J=2.20 Hz, 1 H), 7.16-7.23 (m, 1 H), 7.29-7.38 (m, 4 H).

Example 17

5-Fluoro-4-methoxy-N-(2-methyl-2-phenylpropyl)benzo[d]isoxazol-3-amine

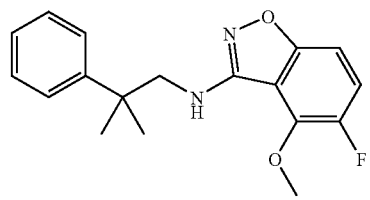

Example 17 was prepared from Intermediate 19 and Intermediate 1 in a similar manner as described for the preparation of Example 1. $^1$H NMR (500 MHz, CDCl$_3$) δ ppm 1.44 (s, 6 H), 3.52 (d, J=6.05 Hz, 2 H), 3.85 (d, J=3.30 Hz, 3 H), 4.55 (bs, 1 H), 6.85 (dd, J=8.80, 2.75 Hz, 1 H), 7.11 (dd, J=12.65, 9.35 Hz, 1 H), 7.23-7.28 (m, 1 H), 7.38 (t, J=7.97 Hz, 2 H), 7.42-7.45 (m, 2 H).

Example 18

4-Chloro-N-(2-methyl-2-phenylpropyl)benzo[d]isoxazol-3-amine

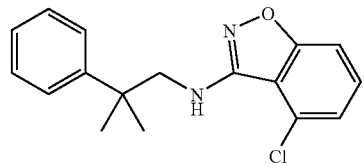

Example 18 was prepared from 2-chloro-6-nitrobenzaldehyde and Intermediate 1 in a similar manner as described for the preparation of Example 1. $^1$H NMR (400 MHz, CDCl$_3$) δ ppm 1.48 (s, 6 H), 3.58 (d, J=5.71 Hz, 2 H), 4.73 (bs, 1H), 7.05 (d, J=7.47 Hz, 1 H), 7.24-7.41 (m, 5 H), 7.43-7.48 (m, 2 H).

Example 19

4,7-Dimethoxy-N-(2-methyl-2-phenylpropyl)benzo[d]isoxazol-3-amine

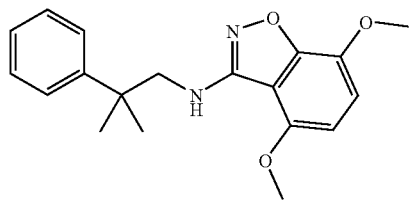

Example 19 was prepared from Intermediate 20 and Intermediate 1 in a similar manner as described for the preparation of Example 1. $^1$H NMR (400 MHz, CDCl$_3$) δ ppm 1.45 (s, 6 H), 3.53 (d, J=6.15 Hz, 2 H), 3.68 (s, 3 H), 3.93 (s, 3 H), 4.68 (t, J=5.93 Hz, 1 H), 6.31 (d, J=8.35 Hz, 1 H), 6.76 (d, J=8.35 Hz, 1 H), 7.24-7.28 (m, 1 H), 7.38 (t, J=7.47 Hz, 2 H), 7.43-7.47 (m, 2 H); mass spec m/z 326 (M+H).

Example 20

4-Fluoro-7-methoxy-N-(2-methyl-2-phenylpropyl)benzo[d]isoxazol-3-amine

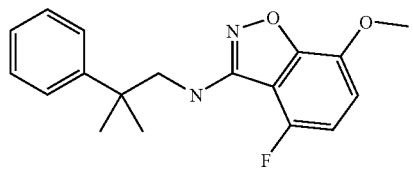

Example 20 was prepared from Intermediate 21 and Intermediate 1 in a similar manner as described for the preparation of Example 1. $^1$H NMR (400 MHz, CDCl$_3$) δ ppm 1.45 (s, 6 H), 3.58 (d, J=6.15 Hz, 2 H), 3.96 (s, 3 H), 4.20 (m, 1 H) 6.65 (t, J=9.01 Hz, 1 H), 6.77 (dd, J=9.0, 3.95 Hz, 1 H) 7.26 (m, 1 H) 7.35-7.45 (m, 4 H); mass spec m/z 315 (M+H).

Example 21

4,5-Dimethoxy-N-(2-methyl-2-phenylpropyl)benzo[d]isoxazol-3-amine

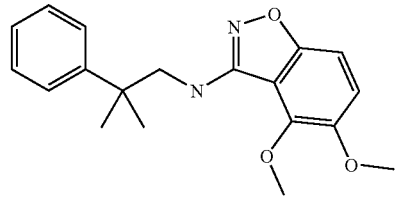

Example 21 was prepared from Intermediate 21 and Intermediate 1 in a similar manner as described for the preparation of Example 1. $^1$H NMR (400 MHz, Solvent) δ ppm 1.46 (s, 6 H), 3.55 (d, J=5.71 Hz, 2 H), 3.71 (s, 3 H), 3.82 (s, 3 H), 4.62 (m, 1 H) 6.94 (d, J=8.79 Hz, 1 H) 7.07 (d, J=8.79 Hz, 1 H) 7.23-7.28 (m, 1 H) 7.38 (m, 2 H), 7.45 (m, 2 H); mass spec m/z 326 (M+H).

Example 22

4-Methoxy-N-(2-methyl-2-phenylpropyl)isoxazolo[5,4-c]pyridin-3-amine

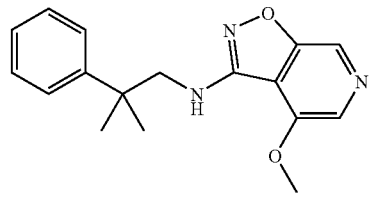

Example 22 was prepared from Intermediate 23 and Intermediate 1 in a similar manner as described for the preparation of Example 1. $^1$H NMR (400 MHz, CDCl$_3$) δ ppm 1.39 (s, 6 H), 3.48 (d, J=6.15 Hz, 2 H), 3.81 (s, 3 H), 4.51 (t, J=5.49 Hz, 1 H), 7.18-7.23 (m, 1 H), 7.31-7.39 (m, 4 H), 7.84 (s, 1 H), 8.38 (s, 1 H).

Example 23

4-Ethyl-N-(2-methyl-2-phenylpropyl)benzo[d]isoxazol-3-amine

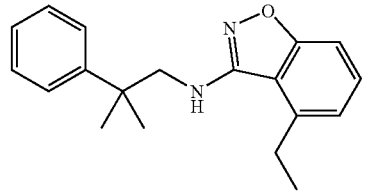

Example 23 was prepared from Intermediate 27 and Intermediate 1 in a similar manner as described for the preparation of Example 1. ¹H NMR (400 MHz, CDCl₃) δ ppm 0.91 (t, J=7.69 Hz, 3 H), 1.42 (s, 6 H), 2.42 (q, J=7.62 Hz, 2 H), 3.52 (d, J=5.71 Hz, 2 H), 3.76 (bs, 1 H), 6.77 (d, J=7.03 Hz, 1 H), 7.12 (d, J=8.35 Hz, 1H), 7.17-7.25 (m, 2 H), 7.31 (t, J=7.69 Hz, 2 H), 7.37-7.41 (m, 2 H).

Example 24

6-Chloro-4-methoxy-N-(2-methyl-2-phenylpropyl) benzo[d]isoxazol-3-amine

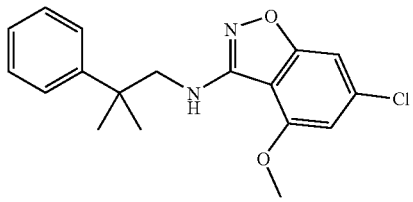

Example 24 was prepared from Intermediate 22a and Intermediate 1 in a similar manner as described for the preparation of Example 1. ¹H NMR (400 MHz, CDCl₃) δ ppm 1.44 (s, 6 H), 3.50 (d, J=6.15 Hz, 2 H), 3.73 (s, 3 H), 4.54 (m, 1 H), 6.44 (s, 1 H), 6.93 (s, 1 H), 7.26 (m, 1 H), 7.37 (m, 2 H), 7.43 (m, 2 H); mass spec m/z 331 (M+H).

Example 25

4-Chloro-6-methoxy-N-(2-methyl-2-phenylpropyl) benzo[d]isoxazol-3-amine

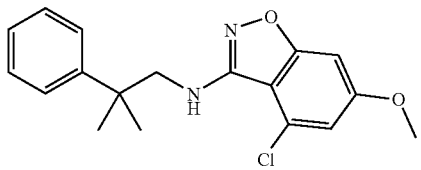

Example 25 was prepared from Intermediate 22b and Intermediate 1 in a similar manner as described for the preparation of Example 1. ¹H NMR (400 MHz, CDCl₃) δ ppm 1.45 (s, 6 H), 3.53 (d, J=6.05 Hz, 2 H), 3.81 (s, 3 H), 4.58 (m, 1 H) 6.67 (s, 1 H), 6.69 (s, 1 H), 7.26 (m, 1 H), 7.36 (t, J=7.70 Hz, 2 H) 7.44 (d, J=7.70 Hz, 2 H); mass spec m/z 331 (M+H).

Example 26

4-Methoxy-N-(2-methyl-2-phenylpropyl)isoxazolo [5,4-d]pyrimidin-3-amine

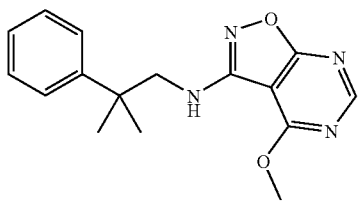

Example 26 was prepared from Intermediate 25 and Intermediate 1 in a similar manner as described for the preparation of Example 1. ¹H NMR (400 MHz, CDCl₃) δ ppm 1.38 (s, 6 H), 3.48 (d, J=6.15 Hz, 2 H), 3.96 (s, 3 H), 4.26 (bs, 1 H), 7.17-7.23 (m, 1 H), 7.28-7.38 (m, 4 H), 8.50 (s, 1 H).

Example 27

4,6-Dimethoxy-N-(2-methyl-2-phenylpropyl)benzo [d]isoxazol-3-amine

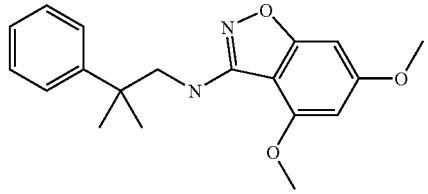

To a vial charged with Example 15 (25 mg, 0.080 mmol) was added a solution of 25% sodium methoxide in methanol (2 mL). Upon completion of addition, the reaction mixture was heated at 125° C. for 6 minutes under microwave conditions. After this time, the reaction mixture was diluted with CH₂Cl₂ (4 mL), washed with H₂O (2 mL) and brine (2 mL), dried over Na₂SO₄ and filtered. The volatiles were removed under reduced pressure to provide a residue. The residue was subjected to chromatography on silica gel eluting with 0% to 15% EtOAc/hexanes to provide Example 27 as a clear colorless oil (22 mg, 85%). ¹H NMR (400 MHz, CDCl₃) δ ppm 1.44 (s, 6 H), 3.51 (d, J=6.15 Hz, 2 H), 3.69 (s, 3 H), 3.80 (s, 3 H), 4.51 (t, J=5.71 Hz, 1 H), 6.06 (s, 1 H), 6.39 (d, J=1.76 Hz, 1 H), 7.24-7.28 (m, 1 H), 7.38 (t, J=7.69 Hz, 2 H), 7.43-7.47 (m, 2 H).

Example 28

4,7-Dichloro-N-(2-methyl-2-phenylpropyl)benzo[d] isoxazol-3-amine

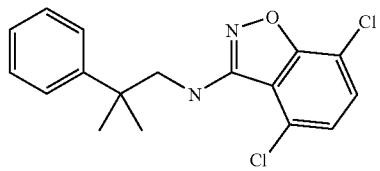

Example 28 was prepared from 3,6-dichloro-2-methoxybenzoic acid and Intermediate 1 in a similar manner as described for the preparation of Example 64 utilizing hydroxylamine in place of methyl hydrazine in the final step in which cyclization was conducted using sodium hydride in THF. ¹H NMR (500 MHz, CDCl₃) δ ppm 1.47 (s, 6 H)

3.54-3.59 (m, 2 H) 4.75 (bs, 1 H) 6.99 (d, J=8.35 Hz, 1H) 7.24-7.28 (m, 1 H), 7.32-7.47 (m, 5 H).

Example 29

4-Methoxy-N-methyl-N-(2-methyl-2-phenylpropyl)benzo[d]isoxazol-3-amine

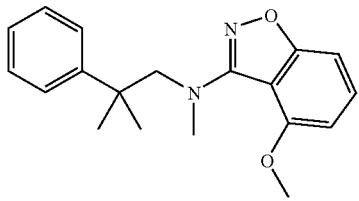

To a stirred solution of Example 1 (26 mg, 0.088 mmol) in DMF (1 mL) at 0° C. was added a 60% dispersion of sodium hydride ("NaH") in oil (3.5 mg, 0.09 mmol). The reaction mixture was stirred for 15 minutes and then iodomethane (16 uL, 0.26 mmol) was added. Upon completion of addition, the reaction mixture was allowed to warm to ambient temperature where it stirred overnight. The reaction mixture was then diluted with EtOAc (20 mL), washed with H$_2$O (3×5 mL) and brine (5 mL), dried over Na$_2$SO$_4$ and filtered. The volatiles were removed under reduced pressure to provide a residue. The residue was subjected to chromatography on silica gel eluting with 10% EtOAc/hexanes to provide Example 29 as a clear colorless oil (13 mg, 48%). $^1$H NMR (400 MHz, CDCl$_3$) δ ppm 1.34 (s, 6 H), 2.75 (s, 3 H), 3.90 (s, 2 H), 3.93 (s, 3 H), 6.58 (d, J=7.91 Hz, 1 H), 7.01 (d, J=8.35 Hz, 1H), 7.16 (t, J=7.47 Hz, 1 H), 7.26-7.30 (m, 2 H), 7.37 (t, J=8.13 Hz, 1 H), 7.42 (d, J=7.47 Hz, 2 H).

Examples 30 and 31

5-Chloro-4-methoxy-N-(2-methyl-2-phenylpropyl)benzo[d]isoxazol-3-amine and 7-chloro-4-methoxy-N-(2-methyl-2-phenylpropyl)benzo[d]isoxazol-3-amine

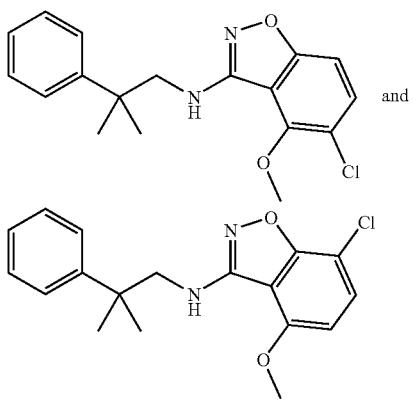

To a stirred solution of Example 1 (78 mg, 0.26 mmol) in DMF (1 mL) was added N-chlorosuccinimide (35 mg, 0.26 mmol). Upon completion of addition, the reaction mixture was heated at 50° C. for 2 h. After this time, the reaction mixture was diluted with EtOAc (5 mL), washed with H$_2$O (3×2 mL) and brine (2 mL), dried over Na$_2$SO$_4$ and filtered. The volatiles were removed under reduced pressure to provide a residue. The residue was subjected to chromatography on silica gel eluting with 5 to 10% EtOAc/hexanes to provide 5-chloro-4-methoxy-N-(2-methyl-2-phenylpropyl)benzo[d]isoxazol-3-amine, Example 30, as a clear colorless oil [less polar compound, 45 mg, 52%, $^1$H NMR (500 MHz, CDCl$_3$) δ ppm 1.46 (s, 6 H), 3.56 (d, J=6.05 Hz, 2 H), 3.63 (s, 3 H), 4.50 (t, J=5.50 Hz, 1 H), 7.01 (d, J=8.80 Hz, 1 H), 7.26 (t, J=7.42 Hz, 1 H), 7.33 (d, J=8.80 Hz, 1 H), 7.38 (t, J=7.70 Hz, 2 H), 7.43-7.46 (m, 2 H)] and 7-chloro-4-methoxy-N-(2-methyl-2-phenylpropyl)benzo[d]isoxazol-3-amine, Example 31, as a white solid [more polar compound, 23 mg, 27%, $^1$H NMR (500 MHz, CDCl$_3$) δ ppm 1.45 (s, 6 H), 3.53 (d, J=6.05 Hz, 2 H), 3.72 (s, 3 H), 4.64 (t, J=5.77 Hz, 1 H), 6.37 (d, J=8.80 Hz, 1 H), 7.24-7.27 (m, 2 H), 7.38 (t, J=7.97 Hz, 2 H), 7.42-7.46 (m, 2 H)].

Examples 32 and 33

5-Chloro-4-methoxy-N-(2-methyl-2-(6-methylpyridin-2-yl)propyl)benzo[d]isoxazol-3-amine and 7-chloro-4-methoxy-N-(2-methyl-2-(6-methylpyridin-2-yl)propyl)benzo[d]isoxazol-3-amine

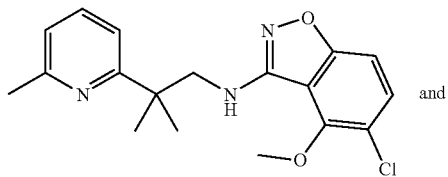

5-Chloro-4-methoxy-N-(2-methyl-2-(6-methylpyridin-2-yl)propyl)benzo[d]isoxazol-3-amine, Example 32 [a clear colorless oil, less polar compound, $^1$H NMR (400 MHz, CDCl$_3$) δ ppm 1.45 (s, 6 H), 2.62 (s, 3 H), 3.61 (d, J=5.71 Hz, 2 H), 3.93 (s, 3 H), 6.70 (bt, J=5.49 Hz, 1 H), 7.01-7.06 (m, 2 H), 7.16 (d, J=7.91 Hz, 1 H), 7.38 (d, J=8.79 Hz, 1 H), 7.56 (t, J=7.91 Hz, 1 H)] and 7-chloro-4-methoxy-N-(2-methyl-2-(6-methylpyridin-2-yl)propyl)benzo[d]isoxazol-3-amine, Example 33 [a white solid, more polar compound, $^1$H NMR (400 MHz, CDCl$_3$) δ ppm 1.43 (s, 6 H), 2.59 (s, 3 H), 3.62 (d, J=6.15 Hz, 2 H), 3.90 (s, 3 H), 6.44 (d, J=8.35 Hz, 1 H), 6.48 (bs, 1 H), 7.01 (d, J=7.91 Hz, 1 H), 7.15 (d, J=7.91 Hz, 1 H), 7.29 (d, J=8.35 Hz, 1 H), 7.55 (t, J=7.91 Hz, 1 H)], were prepared from Example 12 in a similar manner as described for the preparation of Example 29.

Examples 33 and 34

5-Bromo-4-methoxy-N-(2-methyl-2-phenylpropyl)benzo[d]isoxazol-3-amine and 7-bromo-4-methoxy-N-(2-methyl-2-phenylpropyl)benzo[d]isoxazol-3-amine

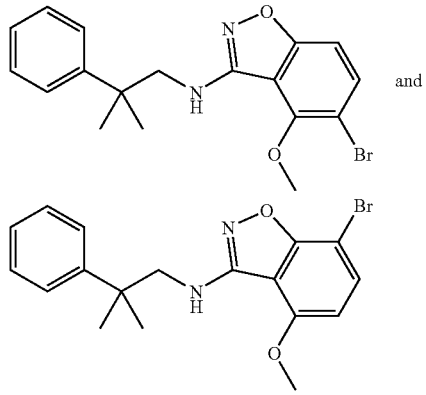

and

5-Bromo-4-methoxy-N-(2-methyl-2-phenylpropyl)benzo[d]isoxazol-3-amine, Example 33 [a clear colorless oil, less polar compound, $^1$H NMR (400 MHz, CDCl$_3$) δ ppm 1.45 (s, 6 H), 3.54-3.58 (m, 5 H), 4.46 (t, J=5.71 Hz, 1 H), 6.96 (d, J=8.79 Hz, 1 H), 7.22-7.26 (m, 1 H), 7.36 (t, J=7.69 Hz, 2 H), 7.44 (t, J=8.13 Hz, 3H)], and 7-bromo-4-methoxy-N-(2-methyl-2-phenylpropyl)benzo[d]isoxazol-3-amine, Example 34 [a white solid, more polar compound, $^1$H NMR (400 MHz, CDCl$_3$) δ ppm 1.44 (s, 6 H), 3.52 (d, J=6.15 Hz, 2 H), 3.71 (s, 3 H), 4.63 (t, J=5.71 Hz, 1 H), 6.32 (d, J=8.35 Hz, 1 H), 7.24-7.28 (m, 1 H), 7.35-7.45 (m, 5 H)], were prepared from Example 1 in a similar manner as described for the preparation of Example 29 using N-bromosuccinimide in place of N-chlorosuccinimide.

Example 35

N-(2-Methyl-2-phenylpropyl)-4-vinylbenzo[d]isoxazol-3-amine

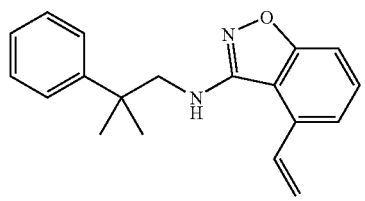

To a vial charged with Example 18 (30 mg, 0.10 mmol), 2,4,6-trivinylcyclotriboroxane pyridine complex (38 mg, 0.1 mmol), tetrakis(triphenylphosphine)palladium(0) (5 mg, 5 mol %) and potassium carbonate (28 mg, 0.20 mmol) was added a 3:1 mixture of 1,2-dimethoxyethane and water (1 mL). The reaction mixture was heated at 180° C. under microwave conditions for 20 minutes. After this time, the reaction mixture was diluted with EtOAc (5 mL), washed with satd NaHCO$_3$ (5 mL), dried over Na$_2$SO$_4$ and filtered. The volatiles were removed under reduced pressure to provide a residue. The residue was subjected to chromatography on silica gel eluting with 0 to 6% EtOAc/hexanes to provide Example 35 as a clear colorless oil (9 mg, 31%). $^1$H NMR (400 MHz, CDCl$_3$) δ ppm 1.40 (s, 6 H), 3.51 (d, J=5.27 Hz, 2 H), 3.94 (s, 1 H), 5.13 (d, J=10.99 Hz, 1 H), 5.34 (d, J=18.46 Hz, 1 H), 6.58 (dd, J=17.58, 10.99 Hz, 1 H), 6.95 (d, J=7.47 Hz, 1 H), 7.17-7.22 (m, 2 H), 7.27-7.39 (m, 5 H).

Example 36

3-(2-Methyl-2-phenylpropylamino)benzo[d]isoxazol-4-ol

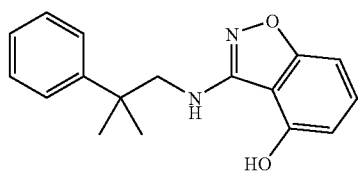

To a stirred solution of Example 1 (30 mg, 0.10 mmol) in 1,2-dichloroethane (1 mL) was added boron tribromide dimethylsulfide complex (125 mg, 0.4 mmol). Upon completion of addition, the reaction mixture was heated at 190° C. under microwave conditions for 10 minutes. At the conclusion of this period, the reaction mixture was diluted with CH$_2$Cl$_2$ (5 mL), washed with satd NaHCO$_3$ (5 mL), dried over Na$_2$SO$_4$ and filtered. The volatiles were removed under reduced pressure to provide a residue. The residue was subjected to preparative High Performance Liquid Chromatography ("HPLC", YMC ODS, 5 u 30×100 mm column, with flow rate of 40 mL/min over 10 min period. 50 to 100% Solvent B. Solvent A=10/90/0.1% MeOH/H$_2$O/trifluoroacetic acid ("TFA"). Solvent B=90/10/0.1%.) to provide Example 36 as a white film (2 mg, 7%). $^1$H NMR (400 MHz, CD$_3$OD) δ ppm 1.43 (s, 6 H), 3.49 (s, 2 H), 6.42 (d, J=7.91 Hz, 1 H), 6.74 (d, J=8.35 Hz, 1 H), 7.20-7.26 (m, 2 H), 7.35 (t, J=7.91 Hz, 2 H), 7.47 (d, J=8.35 Hz, 2 H).

Example 37

4-Methoxy-N-(2-methyl-2-phenylpropyl)-7-(1H-pyrazol-4-yl)benzo[d]isoxazol-3-amine

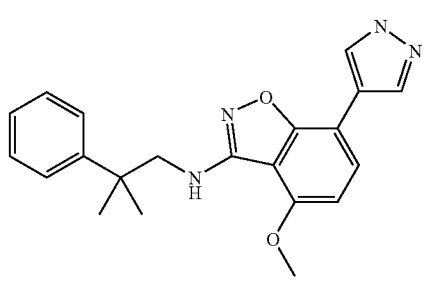

Example 37 was prepared from Example 34 and 4-(4,4,5,5-tetramethyl-1,3,2-dioxaborolan-2-yl)-1H-pyrazole in a similar manner as described for the preparation of Example 35. $^1$H NMR (400 MHz, CDCl$_3$) δ ppm 1.40 (s, 6 H), 3.49 (d, J=6.15 Hz, 2 H), 3.70 (s, 3 H), 4.67 (bt, J=5.93 Hz, 1 H), 6.43

(d, J=8.35 Hz, 1 H), 7.17-7.24 (m, 2 H), 7.32 (t, J=7.91 Hz, 2 H), 7.37-7.42 (m, 2 H), 7.46 (d, J=8.35 Hz, 1 H), 8.12 (s, 2 H).

Example 38

4-Methoxy-N-(2-methyl-2-phenylpropyl)-5-(1H-pyrazol-4-yl)benzo[d]isoxazol-3-amine

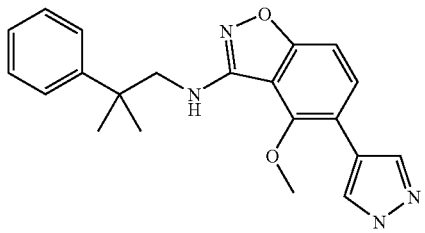

Example 38 was prepared from Example 33 and 4-(4,4,5,5-tetramethyl-1,3,2-dioxaborolan-2-yl)-1H-pyrazole in a similar manner as described for the preparation of Example 35. $^1$H NMR (400 MHz, CDCl$_3$) δ ppm 1.42 (s, 6 H), 3.24 (s, 3 H), 3.55 (d, J=5.71 Hz, 2 H), 4.49 (t, J=5.49 Hz, 1 H), 6.11 (bs, 1 H), 7.06 (d, J=8.35 Hz, 1 H), 7.17-7.22 (m, 1 H), 7.32 (t, J=7.69 Hz, 2 H), 7.41 (t, J=7.91 Hz, 3H), 7.88 (s, 2 H).

Examples 39 and 40

N-(4-methoxybenzo[d]isoxazol-3-yl)-N-(2-methyl-2-phenylpropyl)formamide and 4-methoxy-3-(2-methyl-2-phenylpropylamino)benzo[d]isoxazole-7-carbaldehyde

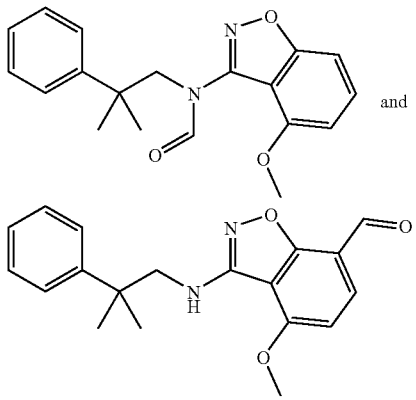

Examples 39 and 40 were prepared from Example 1 in a similar manner as described for the preparation of Intermediate 23 to give as the major product N-(4-methoxybenzo[d]isoxazol-3-yl)-N-(2-methyl-2-phenylpropyl)formamide, Example 39 [a clear colorless oil, less polar compound, $^1$H NMR (400 MHz, CDCl$_3$) δ ppm 1.37 (s, 6 H), 3.98 (s, 3 H), 4.33 (s, 2 H), 6.60 (d, J=7.91 Hz, 1 H), 6.83 (t, J=7.25 Hz, 1H), 6.95 (t, J=7.69 Hz, 2 H), 7.01 (d, J=8.35 Hz, 1 H), 7.21 (d, J=7.47 Hz, 2 H), 7.42 (t, J=8.35 Hz, 1 H), 8.55 (s, 1 H)] and 4-methoxy-3-(2-methyl-2-phenylpropylamino)benzo[d]isoxazole-7-carbaldehyde, Example 40 [a white solid, more polar compound, $^1$H NMR (400 MHz, CDCl$_3$) δ ppm 1.46 (s, 6 H), 3.55 (d, J=6.15 Hz, 2 H), 3.84 (s, 3 H), 4.63 (bs, 1 H), 6.58 (d, J=8.35 Hz, 1 H), 7.25-7.30 (m, 1 H), 7.39 (t, J=7.69 Hz, 2 H), 7.43-7.48 (m, 2 H), 7.90 (d, J=8.35 Hz, 1 H), 10.25 (s, 1 H)].

Example 41

4-Methoxy-1-methyl-N-(2-methyl-2-phenylpropyl)-1H-indazol-3-amine

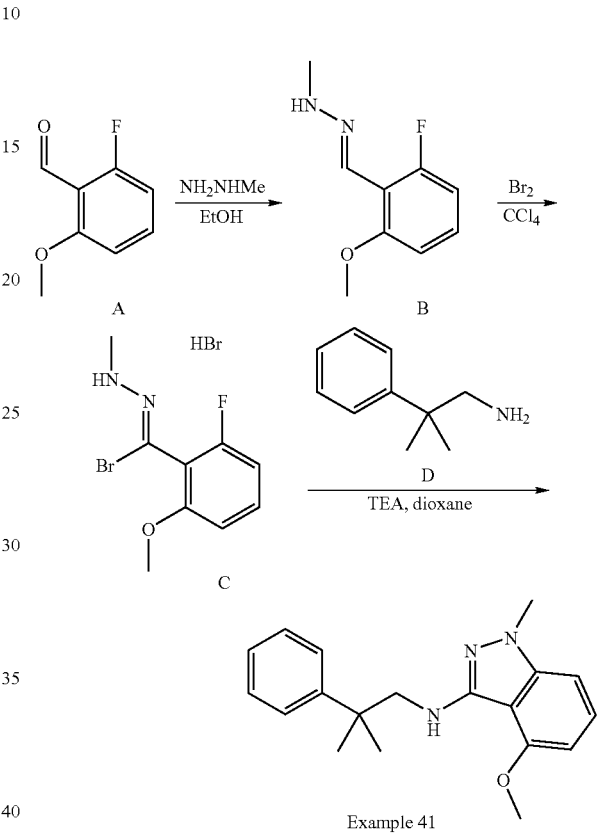

Example 41

Hydrozone B: To a solution of 2-fluoro-6-methoxybenzaldehye (Compound A, 154 mg, 1.0 mmol) in ethanol (5 mL) was added N-methyl hydrazine (46 mg, 1.0 mmol). The reaction mixture was heated at reflux for 1 h and then allowed to cool to ambient temperature. Once at the prescribed temperature, the volatiles were removed under reduced pressure to provide a residue. The residue was brought up into H$_2$O (5 mL) and extracted with Et$_2$O (3×5 mL). The combined organic extracts were dried over MgSO$_4$ and then filtered. The volatiles were removed under reduced pressure to provide crude hydrazone B (165 mg, 0.91 mmol, 91%).

Compound C: The hydrazone B was dissolved in carbon tetrachloride (5 mL). The resulting solution was cooled to −15° C. and then a solution of bromine (38 uL, 0.74 mmol) in carbon tetrachloride (10 mL) was added dropwise at such a rate as to maintain the temperature at −15° C. Upon completion of addition, the reaction mixture was allowed to warm to ambient temperature. Once at the prescribed temperature, the reaction mixture was stirred for 1 h and then the solvent was decanted to provide the 1-(bromo(2-fluoro-6-methoxyphenyl)methylene)-2-methylhydrazine hydrobromide salt, Compound C.

Example 41: Compound C was triturated with carbon tetrachloride (5 ml) to provide a residue. To the residue of C was added dioxane (8 mL). The resulting mixture was cooled in an ice-bath and then a solution of Intermediate 1 (Compound D, 270 mg, 1.8 mmol) in dioxane (2 mL) followed by triethylamine (0.14 mL, 1.0 mmol) were added. Upon completion of addition, the reaction mixture was allowed to warm to ambient temperature where it stirred overnight. At the conclusion of this period, the reaction was diluted with satd NaHCO$_3$ (5 mL) and extracted with Et$_2$O (3×5 mL). The combined organic extracts were dried over Na$_2$SO$_4$ and filtered. The volatiles were removed under reduced pressure to provide a residue. The residue was subject to chromatography on silica gel eluting with 5 to 40% EtOAc/hexanes to provide Example 41 as a white solid (52 mg, 17%). $^1$H NMR (400 MHz, CDCl$_3$) δ ppm 1.46 (s, 6 H), 3.53 (d, J=6.15 Hz, 2 H), 3.69 (s, 3 H), 3.75 (s, 3 H), 4.46 (bt, J=5.71 Hz, 1 H), 6.14 (d, J=7.91 Hz, 1 H), 6.65 (d, J=8.35 Hz, 1 H), 7.10-7.15 (m, 1H), 7.21-7.26 (m, 1 H), 7.36 (t, J=7.69 Hz, 2 H), 7.47 (d, J=7.03 Hz, 2 H).

Example 42

4-Methoxy-N-(2-methyl-2-phenylpropyl)-1H-indazol-3-amine

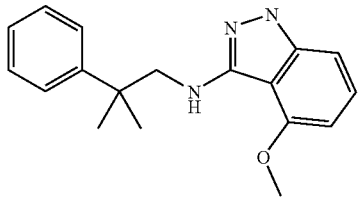

Example 42 was prepared from Intermediate 1 in a similar manner as described for the preparation of Example 64 utilizing hydrazine in the final step. $^1$H NMR (400 MHz, CDCl$_3$) δ ppm 1.46 (s, 6 H), 3.55 (d, J=6.15 Hz, 2 H), 3.72 (s, 3 H), 4.58 (bt, J=5.93 Hz, 1 H), 6.23 (d, J=7.47 Hz, 1 H), 6.78 (d, J=7.91 Hz, 1 H), 7.15 (t, J=7.91 Hz, 1 H), 7.22-7.27 (m, 1 H), 7.37 (t, J=7.69 Hz, 2 H), 7.47 (d, J=7.47 Hz, 2H).

Example 43

1-Isopropyl-4-methoxy-N-(2-methyl-2-phenylpropyl)-1H-indazol-3-amine

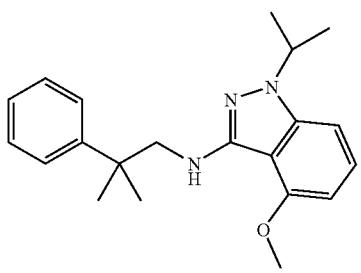

To a stirred solution of Example 42 (16 mg, 0.054 mmol) in DMF (0.5 mL) was added potassium carbonate (8.3 mg, 0.06 mmol) followed by 2-bromopropane (18 uL, 0.12 mmol). Upon completion of addition, the reaction mixture was heated at 100° C. for 6 h. At the conclusion of this period, the reaction mixture was subjected to preparative HPLC (Rt=7.76 minutes using YMC ODS 5 u 30×100 mm column with flow rate of 40 mL/min over 10 min period; 20 to 100% Solvent B. Solvent A=10/90/0.1% MeOH/H$_2$O/TFA. Solvent B=90/10/0.1%) to provide Example 43 as a pink film (1.3 mg, 7%). $^1$H NMR (500 MHz, CDCl$_3$) δ ppm 1.44 (s, 6 H), 1.45 (s, 3 H), 1.47 (s, 3 H), 3.56 (s, 2 H), 3.69 (s, 3 H), 6.14 (d, J=7.70 Hz, 1 H), 6.73 (d, J=8.80 Hz, 1 H), 7.09 (t, J=7.97 Hz, 1 H), 7.21-7.24 (m, 1 H), 7.35 (t, J=7.70 Hz, 2 H), 7.47 (d, J=8.25 Hz, 2 H).

Example 44

4-Methoxy-N-(2-methyl-2-phenylpropyl)benzo[d]isothiazol-3-amine

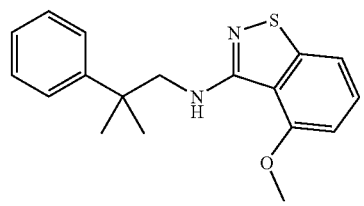

To a stirred solution of Intermediate 1 (93 mg, 0.62 mmol) in THF (6 mL) at −78° C. was added a solution of 1.6 M n-BuLi in hexane (0.39 mL, 0.62 mmol) at a rate which kept the temperature below −70° C. Upon completion of addition, a solution of 3-chloro-4-methoxybenzo[d]isothiazole (prepared in a similar manner as the preparation described in *J. Med. Chem.* 1991, 34, 3316; 50 mg, 0.25 mmol) in THF (1.5 mL) was added at a rate which kept the temperature below −70° C. The reaction mixture was then allowed to warm to 0° C. Once at the prescribed temperature, the reaction mixture was quenched with satd NH$_4$Cl (5 mL). The organic layer was evaporated on the rotovap and the aqueous layer was extracted with CH$_2$Cl$_2$ (3×10 mL). The combined organic extracts were dried over MgSO$_4$ and filtered. The volatiles were removed under reduced pressure to provide a residue. The residue was subjected to chromatography on silica gel eluting with 0 to 20% EtOAc/hexanes to provide Example 44 as a clear colorless oil (15 mg, 19%). $^1$H NMR (400 MHz, CDCl$_3$) δ ppm 1.45 (s, 6 H), 3.66 (s, 3 H), 3.73 (d, J=5.27 Hz, 2 H), 6.06 (bt, J=5.05 Hz, 1 H), 6.53 (d, J=7.47 Hz, 1 H), 7.21-7.29 (m, 3 H), 7.38 (t, J=7.69 Hz, 2 H), 7.47 (d, J=7.47 Hz, 2 H).

Example 45

4-Methoxy-N-(2-methyl-2-(6-methylpyridin-2-yl)propyl)benzo[d]isothiazol-3-amine

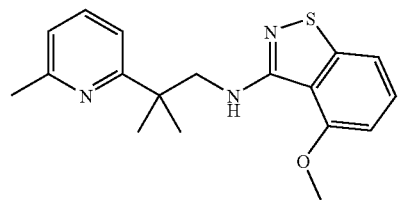

Example 45 was prepared from Intermediate 8 in a similar manner as described for the preparation of Example 44. $^1$H NMR (400 MHz, CDCl$_3$) δ ppm 1.45 (s, 6 H), 2.58 (s, 3 H), 3.82-3.85 (m, 5 H), 6.60 (d, J=7.47 Hz, 1 H), 6.92 (bt, J=5.05 Hz, 1 H), 6.99 (d, J=7.47 Hz, 1 H), 7.18 (d, J=7.91 Hz, 1 H), 7.23-7.32 (m, 2H), 7.54 (t, J=7.69 Hz, 1 H).

Example 46

8-Methoxy-N-(2-methyl-2-phenylpropyl)isoquinolin-1-amine

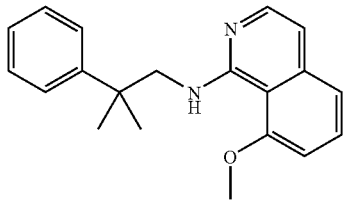

To a vial charged with Intermediate 1 (18 mg, 0.12 mmol), 1-chloro-8-methoxyisoquinoline (prepared in a similar manner as the preparation described in *Heterocycles* 1996, 42, 415; 20 mg, 0.10 mmol), tris(dibenzylideneacetone)dipalladium (0) (3.7 mg, 4 mol %), 2,2'-bis(diphenylphosphino)-1,1'-binaphthyl (5 mg, 8 mol %) and sodium t-butoxide (14 mg, 0.14 mmol) was added toluene (0.5 mL). Upon completion of addition, the reaction mixture was heated at 75° C. for 14 h. After this time, the reaction mixture was diluted with brine (5 mL), extracted with Et$_2$O (3×5 mL), dried over Na$_2$SO$_4$ and filtered. The volatiles were removed under reduced pressure to provide a residue. The residue was subjected to chromatography on silica gel eluting with 25% EtOAc/hexanes to provide Example 46 as a yellow solid (24 mg, 77%). $^1$H NMR (400 MHz, CDCl$_3$) δ ppm 1.46 (s, 6 H), 3.53 (s, 3 H), 3.83 (d, J=4.83 Hz, 2 H), 6.62 (d, J=7.91 Hz, 1 H), 6.69 (d, J=5.71 Hz, 1 H), 7.12 (d, J=7.47 Hz, 1 H), 7.22-7.29 (m, 1 H), 7.31-7.40 (m, 4 H), 7.49 (d, J=8.35 Hz, 2 H), 7.88 (d, J=5.71 Hz, 1 H).

Example 47

5-Methoxy-N-(2-methyl-2-phenylpropyl)quinazolin-4-amine

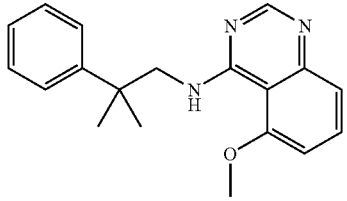

Example 47 was prepared from Intermediate 1 and 4-chloro-5-methoxyquinazoline (prepared in a similar manner as the preparation described in Tetrahedron 2004, 60, 5373) in a similar manner as described for the preparation of Example 46. $^1$H NMR (400 MHz, CDCl$_3$) δ ppm 1.45 (s, 6 H), 3.55 (s, 3 H), 3.88 (d, J=3.52 Hz, 2 H), 6.65 (d, J=7.91 Hz, 1 H), 7.26-7.36 (m, 2 H), 7.41 (t, J=6.81 Hz, 2H), 7.46-7.52 (m, 3 H), 7.64 (bs, 1 H), 8.51 (s, 1 H).

Example 48

4-Chloro-8-methoxy-N-(2-methyl-2-phenylpropyl)isoquinolin-1-amine

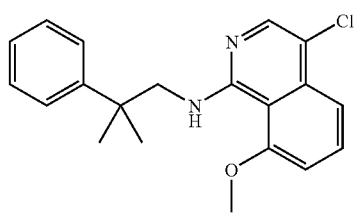

Example 48 was prepared from Example 46 in a similar manner as described for the preparation of Examples 30 and 31. $^1$H NMR (400 MHz, CDCl$_3$) δ ppm 1.36 (s, 6 H), 3.51 (s, 3 H), 3.72 (d, J=5.27 Hz, 2 H), 6.71 (dd, J=6.81, 1.98 Hz, 1 H), 7.18 (t, J=7.25 Hz, 1 H), 7.31 (t, J=7.91 Hz, 2 H), 7.39-7.46 (m, 4 H), 7.80 (s, 1 H).

Examples 49 and 50

8-Chloro-5-methoxy-N-(2-methyl-2-phenylpropyl)quinazolin-4-amine and 6-chloro-5-methoxy-N-(2-methyl-2-phenylpropyl)quinazolin-4-amine

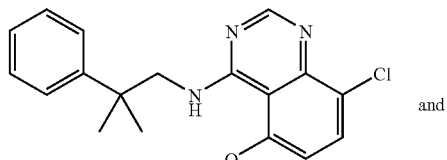

and

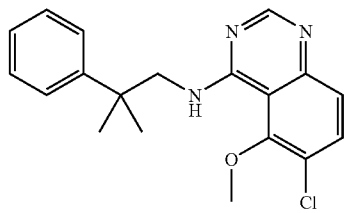

Examples 49, 8-chloro-5-methoxy-N-(2-methyl-2-phenylpropyl)quinazolin-4-amine [a pale blue solid, less polar compound, $^1$H NMR (500 MHz, CDCl$_3$) δ ppm 1.45 (s, 6 H), 3.55 (s, 3 H), 3.90 (d, J=5.50 Hz, 2 H), 6.59 (d, J=8.80 Hz, 1 H), 7.29 (t, J=7.15 Hz, 1 H), 7.42 (t, J=7.70 Hz, 2 H), 7.45-7.49 (m, 2 H), 7.62 (d, J=8.25 Hz, 1 H), 7.70 (bs, 1 H), 8.64 (s, 1 H)], and 50, 6-chloro-5-methoxy-N-(2-methyl-2-phenylpropyl)quinazolin-4-amine [a white solid, more polar compound, $^1$H NMR (500 MHz, CDCl$_3$) δ ppm 1.48 (s, 6 H) 3.29 (s, 3 H) 3.92 (d, J=4.95 Hz, 2 H) 7.26-7.29 (m, 1 H) 7.41 (t, J=7.70 Hz, 2 H) 7.46-7.50 (m, 3 H) 7.58 (d, J=8.80 Hz, 1 H)

7.67 (bs, 1 H) 8.53 (s, 1 H)], were prepared from Example 47 in a similar manner as described for the preparation of Examples 30 and 31.

Example 51

2-Chloro-5-methoxy-N-(2-methyl-2-phenylpropyl) quinazolin-4-amine

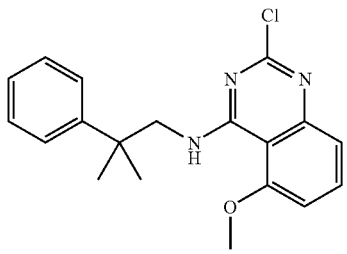

To a stirred solution of Intermediate 29 (80 mg, 0.35 mmol) in THF (5 mL) was added Intermediate 1 (52 mg, 0.35 mmol) followed by triethylamine (0.12 mL, 0.88 mmol). Upon completion of addition, the reaction mixture was stirred for 1 h. At the conclusions of this period, the volatiles were removed under reduced pressure to provide a residue. The residue was subjected to chromatography on silica gel eluting with 0 to 30% EtOAc/hexanes to provide Example 51 as a white solid (82 mg, 69%). $^1$H NMR (400 MHz, CDCl$_3$) δ ppm 1.45 (s, 6 H), 3.55 (s, 3 H), 3.88 (d, J=5.27 Hz, 2 H), 6.64 (d, J=7.91 Hz, 1 H), 7.23-7.32 (m, 2 H), 7.40-7.51 (m, 5 H), 7.77 (bs, 1 H).

Example 52

5-Methoxy-4-(2-methyl-2-phenylpropylamino) quinazolin-2(1H)-one

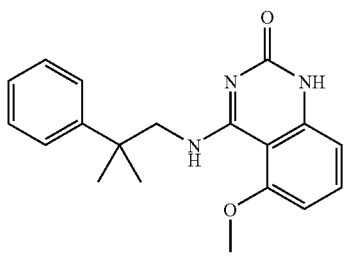

To a flask charged with Example 51 (80 mg, 0.23 mmol) was added acetic acid (2 mL). The reaction mixture was heated at 70° C. for 5 h, and then the volatiles were removed under reduced pressure to provide a residue. To the residue was added satd NaHCO$_3$ followed by EtOAc. The organic layer was separated, washed with brine, dried over Na$_2$SO$_4$ and filtered. The volatiles were removed under reduced pressure to provide another residue. This residue was subjected to chromatography on silica gel eluting with 0 to 10% MeOH/ CH$_2$Cl$_2$ to provide Example 52 as a white solid (73 mg, 96%). $^1$H NMR (400 MHz, CDCl$_3$) δ ppm 1.43 (s, 6 H), 3.50 (s, 3 H), 3.98 (d, J=5.27 Hz, 2 H), 6.41 (d, J=8.35 Hz, 1 H), 6.98 (d, J=8.35 Hz, 1 H), 7.25-7.35 (m, 2 H), 7.40 (t, J=7.25 Hz, 2 H), 7.44-7.48 (m, 2 H), 7.74 (bs, 1 H), 11.99 (bs, 1 H).

Example 53

5-Methoxy-1-methyl-4-(2-methyl-2-phenylpropylamino)quinazolin-2(1H)-one

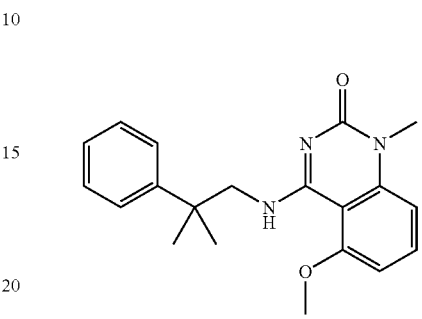

To a stirred solution of Example 52 (32 mg, 0.1 mmol) in DMF (1 mL) was added a 60% dispersion of sodium hydride in oil (4 mg, 0.1 mmol). The reaction mixture was stirred for 10 minutes and then iodomethane (6.2 uL, 0.1 mmol) was added. Upon completion of addition the reaction mixture was stirred for 2 h. At the conclusion of this period, the reaction mixture was diluted with EtOAc, washed with brine, dried over Na$_2$SO$_4$ and filtered. The volatiles were removed under reduced pressure to provide a residue. The residue was subjected to preparative HPLC (Rt=8.03 minutes using YMC ODS-A 5 u 20×100 mm column with flow rate of 20 mL/min over 10 min period; 20 to 100% Solvent B. Solvent A=10/90/ 0.1% MeOH/H$_2$O/TFA. Solvent B=90/10/0.1%) to provide Example 53 as a white solid (10 mg, 30%). $^1$H NMR (500 MHz, CDCl$_3$) δ ppm 1.41 (s, 6 H), 3.50 (s, 3 H), 3.54 (s, 3 H), 3.94 (d, J=4.95 Hz, 2 H), 6.49 (d, J=8.25 Hz, 1 H), 6.76 (d, J=8.25 Hz, 1 H), 7.25-7.28 (m, 1 H), 7.37-7.45 (m, 5 H), 7.71 (bs, 1 H).

Example 54

8-Chloro-5-methoxy-4-(2-methyl-2-phenylpropylamino)quinazolin-2(1H)-one

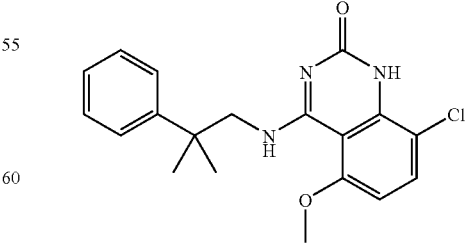

Example 54 was prepared from Example 52 in a similar manner as described for the preparation of Examples 30 and 31. $^1$H NMR (400 MHz, CDCl$_3$) δ ppm 1.42 (s, 6 H), 3.50 (s, 3 H), 3.96 (d, J=5.27 Hz, 2 H)—, 6.42 (d, J=8.79 Hz, 1 H), 7.25-7.31 (m, 1 H), 7.39-7.46 (m, 5 H), 7.76 (bs, 1 H), 8.26 (bs, 1 H).

Example 55

5-Methoxy-4-(2-methyl-2-phenylpropylamino)-2H-benzo[e][1,3]oxazin-2-one

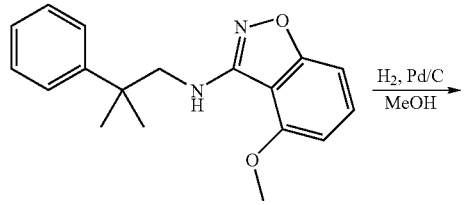

A

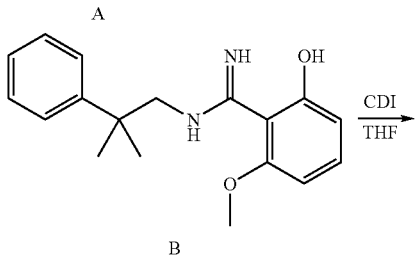

B

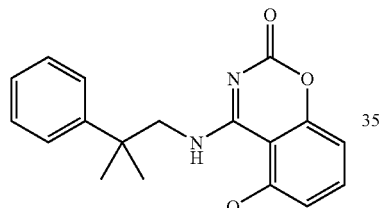

Example 55

Compound B: Compound A (prepared in a similar manner as described the preparation of Example 1, 116 mg, 0.39 mmol) was dissolved in MeOH (10 mL) and then palladium (10% on charcoal, 24 mg) was added. The reaction mixture was stirred under H₂ at atmospheric pressure for 16 h. At the conclusion of this period, the reaction mixture was flushed with nitrogen and then filtered through celite. The solvent was removed under reduced pressure to provide Compound B (117 mg) as a gray solid. ¹H NMR (400 MHz, CDCl₃) δ ppm 1.51 (s, 6 H), 3.34 (d, J=3.08 Hz, 2 H) 3.68 (br-s, 3 H), 5.95 (d, J=8.35 Hz, 1 H), 6.49 (d, J=8.79 Hz, 1 H), 7.08 (t, J=8.35 Hz, 1 H), 7.26 (m, 1 H), 7.35-7.45 (m, 4 H).

Example 55: Compound B (30 mg, 0.10 mmol) was dissolved in THF (0.4 mL) and then carbonyldiimidizole ("CDI", 24 mg, 0.15 mmol) was added. The resulting mixture was heated at 140° C. in a microwave reactor for 5 min. After this time, more CDI (0.23 mg, 0.15 mmol) was added and the reaction mixture was heated at 150° C. in a microwave reactor for 5 min. At the conclusion of this period, the reaction mixture was subjected to chromatography on silica gel eluting with 40 to 100% EtOAc/hexanes to provide Example 55 (19 mg) as a white solid. ¹H NMR (400 MHz, CDCl₃) δ ppm 1.43 (s, 6 H), 3.53 (s, 3 H), 3.96 (d, J=5.71 Hz, 2 H), 6.58 (d, J=8.35 Hz, 1 H), 6.86 (d, J=8.79 Hz, 1 H), 7.26 (m, 1 H), 7.39-7.48 (m, 5 H), 7.86 (s, 1 H), mass spec m/z 325 (M+H).

Examples 56 and 57

Isomers 1 and 2 of 3-(3-fluoro-phenyl)-4-(4-methoxy-benzo[d]isoxazol-3-ylamino)-butan-1-ol

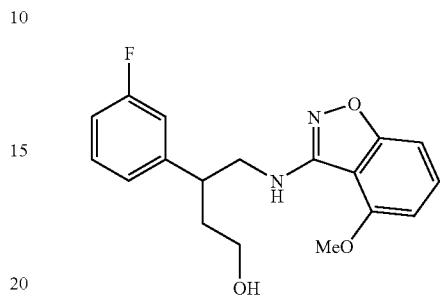

Examples 56 and 57 were prepared from 2-fluoro-6-methoxybenzaldehyde and Intermediate 32 in a similar manner as described for the preparation of Example 1. The enantiomers were separated by preparative-chiral HPLC (CHIRALCEL® OD® 5 cm×50 cm) eluting isocratically with 20% isopropanol/heptane to provide Example 56 (140 mg) and Example 57 (135 mg).

Example 58

Isomer 1 of ethyl-carbamic acid 3-(3-fluoro-phenyl)-4-(4-methoxy-benzo[d]isoxazol-3-ylamino)-butyl ester

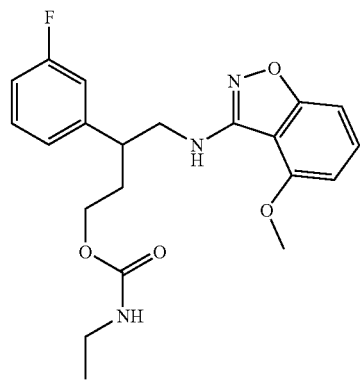

A solution of Example 56 (20 mg, 0.060 mmol) and ethyl isocyanate ("EtNCO", 50 μL) in THF (2 ml) was placed in a sealed tube and stirred at 100° C. for 10 h. After this time, the reaction mixture was concentrated under reduced pressure to provide an oily residue. The oily residue was subjected to column chromatography on silica gel eluting with 0-100% EtOAc/Hex to provide Example 58 (16.1 mg, 0.040 mmol, 66%) as a colorless oil. [M+H]=402.2.

Example 59

Isomer 2 of ethylcarbamic acid 3-(3-fluoro-phenyl)-4-(4-methoxy-benzo [d]isoxazol-3-ylamino)-butyl ester

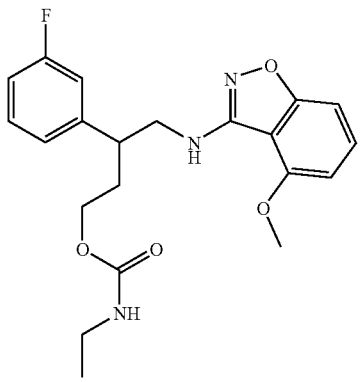

Example 59 was prepared from Example 57 in a similar manner as described for the preparation of Example 58. [M+H]=402.2.

Example 60

(+/−)-4-(4-methoxybenzo[d]isoxazol-3-ylamino)-3-phenylbutan-1-ol

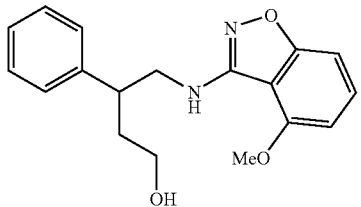

Example 60 were prepared from 2-fluoro-6-methoxybenzaldehyde and Intermediate 35 in a similar manner as described for the preparation of Example 1. [M+H]=313.2

Examples 61 and 62

Isomer 1 and Isomer 2 of 4-(4-methoxybenzo[d]isoxazol-3-ylamino)-3-phenylbutyl ethylcarbamate

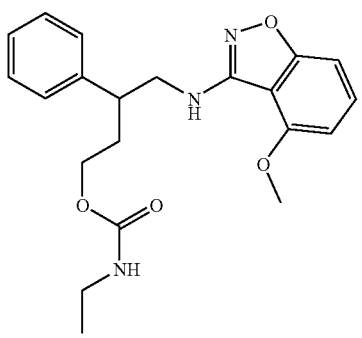

Examples 61 and 62 were prepared from Example 60 in a similar manner as described for the preparation of Example 58. The enantiomers were separated by preparative-chiral HPLC (CHIRALCEL® OD® 5 cm×50 cm) eluting isocratically with 35% isopropanol/heptane to provide Example 61 and Example 62. [M+H]=384.2.

Example 63

(+/−)-(4-Benzyloxy-2-(3-fluoro-phenyl)-butyl]-(4-methoxy-1-methyl-1H-indazol-3-yl)-amine

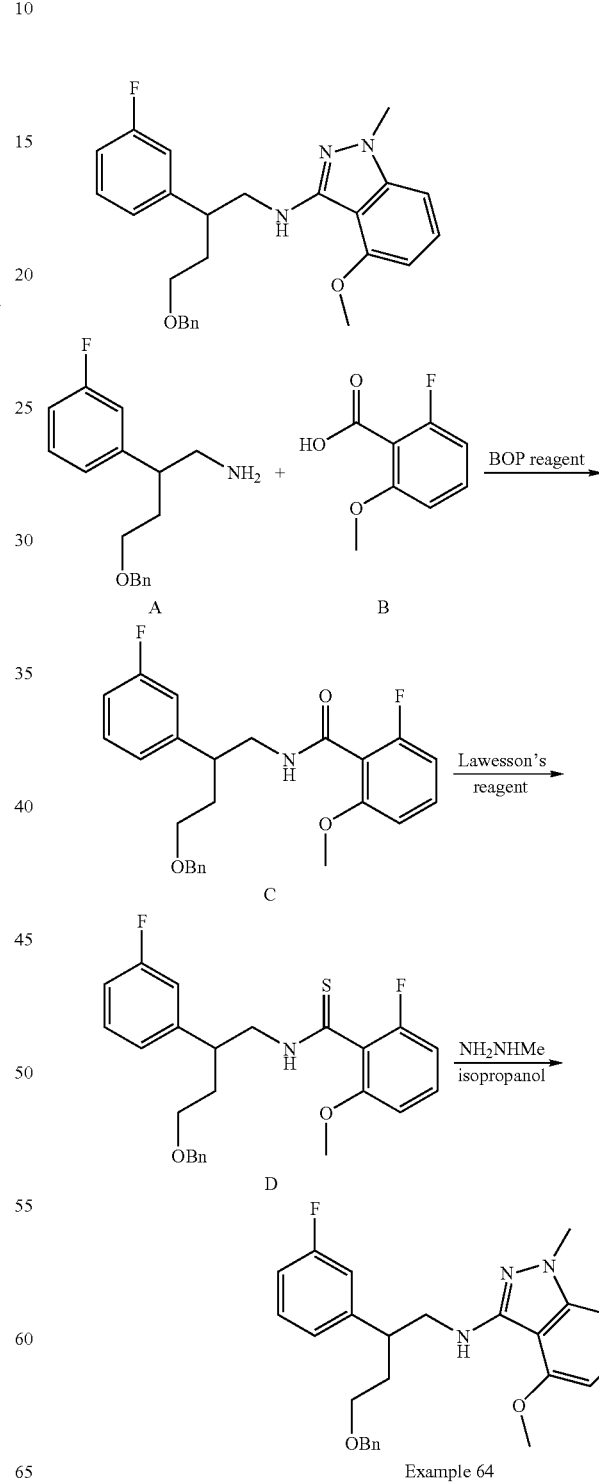

Compound C: To a stirred solution of Compound 2 (Intermediate 31, 0.50 g, 1.9 mmol) and triethylamaine ("Et$_3$N", 0.5 ml) in THF (40 ml) was added in one portion both 6-fluoro-2-methoxybenzoic acid (Compounds B, 0.38 g, 2.2 mmol) and BOP reagent (1.2 g, 2.2 mmol). Upon completion of addition, the resulting solution was stirred at ambient temperature for 6 h. After this time, the reaction mixture was concentrated under reduced pressure to provide an oily residue. The oily residue was purified by silica gel chromatography, eluted with 0-100% EtOAc/Hexane to provide Compound C (0.41 g, 0.96 mmol, 50%) as a colorless oil.

Compound D: A solution of Compound C (0.41 g, 0.96 mmol) and Lawesson's reagent (0.23 g, 0.58 mmol) in toluene (10 ml) was stirred at 85° C. for 12 h. At the conclusion of this period, the reaction mixture was concentrated under reduced pressure to provide an oily residue. The oily residue was purified by silica gel chromatography, eluted with 0-80% EtOAc/Hexane to provide Compound D (0.41 g, 96%).

Example 63: A solution of Compound D (45 mg, 0.1 mmol) and methylhydrazine (0.1 ml) in i-PO ("i-PO", 1 ml) was stirred at 200° C. under microwave conditions for 0.5 h. At the conclusion of this period, the reaction mixture was concentrated under reduced pressure to provide an oily residue. The oily residue was subjected to preparative HPLC (YMC S5 ODS 30×250 mm reverse phase column; 30 min gradient from 70:30 A:B to 100% B, where solvent A=90:10:0.1H$_2$O: MeOH: TFA and solvent B=90:10:0.1 MeOH: H$_2$O: TFA) to provide Example 63 (18.2 mg, 43%). [M+H]=433.0.

Example 64

(+/−)-(4-Benzyloxy-2-(3-fluoro-phenyl)-butyl]-(4-methoxy-1H-indazol-3-yl)-amine

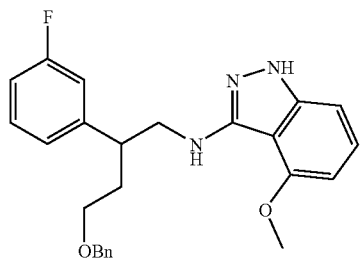

A solution of Compound D of Example 63 (45 mg, 0.1 mmol) and hydrazine hydrate (0.2 ml) in isopropyl alcohol (1 ml) of was stirred at 100° C. for 12 h. After this time, the reaction mixture was concentrated under reduced pressure to provide an oily residue. The oily residue was subjected to preparative HPLC (as described in the preparation of Example 64) to provide Example 64 (12.2 mg, 28%). [M+H] =419.0.

Example 65

(+/−)-(4-Benzyloxy-2-phenyl-butyl)-(4-chloro-1-methyl-1H-pyrazolo[4,3-c]pyridin-3-yl)-amine

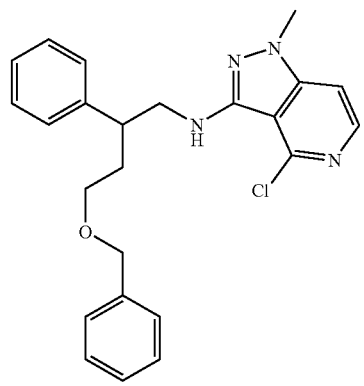

Example 65 was prepared in a similar manner as described for the preparation of Example 63 using 2-chloro-4-fluoronicotinic acid as Compound B. [M+H]=442.1.

Example 66

(+/−)-(4-Benzyloxy-2-phenyl-butyl)-(1-methyl-1H-pyrazolo[3,4-b]pyrazin-3-yl)-amine

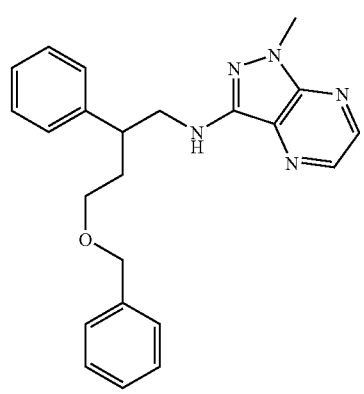

Example 66 was prepared in a similar manner as described for the preparation of Example 63 using 3-fluoropyrazine-2-carboxylic acid as Compound B. [M+H]=391.0.

Example 67

4-methoxy-3-(2-methyl-2-phenylpropylamino)-1H-isoindol-1-one

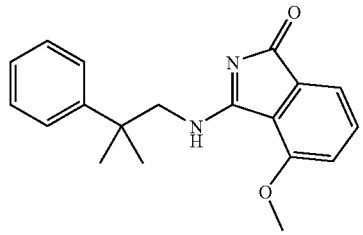

A mixture of 2-methyl-2-phenylpropan-1-amine (Intermediate 1, 500 mg, 2.8 mmol) and 3-imino-4-methoxyisoindolin-1-one (Intermediate 38, 430 mg, 2.8 mmol) in isopropanol (20 mL) was heated at 70° C. for 4 h, the solvent was evaporated and the residue was flash chromatographed 0-100% ethyl acetate-hexane to give Example 67 (530 mg, 62%) as a yellow solid. Recrystallization from butyl acetate produced a white solid mp 138-140° C. $^1$H NMR (400 MHz, CDCl$_3$) δ ppm 1.46 (s, 6H), 3.71 (s, 3 H), 3.91 (d, J=6.15 Hz, 2 H), 6.73 (bs, 1 H), 6.92 (d, J=8.35 Hz, 1 H), 7.28-7.34 (m, 2 H), 7.40-7.48 (m, 5 H).

Example 68

5-Methoxy-4-(2-methyl-2-phenylpropylamino)phthalazin-1(2H)-one

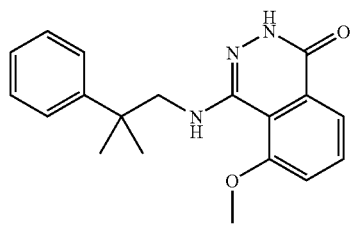

A stirred solution of 4-methoxy-3-(2-methyl-2-phenylpropylamino)-1H-isoindol-1-one (Example 68, 0.40 g, 1.3 mmol) in ethanol (10 mL) was treated with hydrazine hydrate (0.13 mL, 2.6 mmol). After two hours the precipitated solid was removed by filtration, the filtrate was concentrated under vacuum, the residue suspended in ethyl acetate then filtered to give Example 68 (0.125 g, 30%) as a tan powder. $^1$H NMR (400 MHz, CD$_3$OD) δ ppm 1.46 (s, 6 H), 3.64 (s, 2 H), 3.68 (s, 3H), 7.28 (t, J=7.25 Hz, 1 H), 7.38-7.45 (m, 3 H), 7.50-7.54 (m, 2 H), 7.75-7.84 (bs, 1 H), 7.88 (d, J=7.47 Hz, 1 H).

Example 69

4-Chloro-8-methoxy-N-(2-methyl-2-phenylpropyl)phthalazin-1-amine

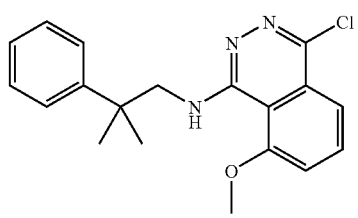

A mixture of 5-methoxy-4-(2-methyl-2-phenylpropylamino)phthalazin-1(2 H)-one (Example 69, 73 mg, 0.23 mmol) and phosphorus oxychloride (1 mL) was heated in a microwave reactor at 150° C. for five minutes. The solvent was removed under vacuum, the residue was partitioned between chloroform and sodium bicarbonate, the organic fraction was dried over magnesium sulfate and the solvent was removed under vacuum. The residue was purified by flash chromatography using a 0-100% ethyl acetate-hexane gradient to afford Example 69 (20 mg, 25%) as a white solid. [M+H]/z 342. $^1$H NMR (400 MHz, CDCl$_3$) δ ppm 1.46 (s, 6 H), 3.59 (s, 3 H), 3.93 (d, J=4.83 Hz, 2 H), 6.99-7.05 (m, 2 H), 7.25-7.30 (m, 1 H), 7.41 (t, J=7.69 Hz, 2 H), 7.49 (d, J=8.35 Hz, 2 H), 7.61-7.64 (m, 2 H).

Example 70

4,8-dimethoxy-N-(2-methyl-2-phenylpropyl)phthalazin-1-amine

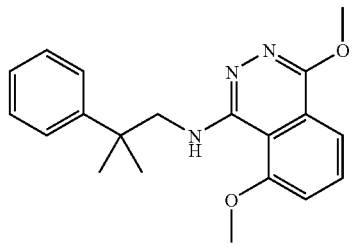

A mixture of 4-chloro-8-methoxy-N-(2-methyl-2-phenylpropyl)phthalazin-1-amine (Example 70, 20 mg, 0.059 mmol) and potassium carbonate (60 mg, 0.43 mmol) in methanol (1 mL) was heated in a microwave reactor at a pressure priority of twenty bar for ten minutes. The solid was filtered off, the solvent was removed under vacuum and the residue was purified by flash chromatography using 0-100% ethyl acetate-hexane mixture affording Example 70 (12 mg, 61%) as a tan gum. [M+H]/z 338. $^1$H NMR (400 MHz, CDCl$_3$) δ ppm 1.47 (s, 6 H), 3.58 (s, 3 H), 3.92 (d, J=5.27 Hz, 2 H), 4.10 (s, 3 H), 6.72 (bs, 1 H), 7.24-7.28 (m, 1 H), 7.39 (t, J=7.69 Hz, 2 H), 7.50 (d, J=7.03 Hz, 2 H), 7.57-7.64 (m, 2 H).

Example 71

8-methoxy-N-(2-methyl-2-phenylpropyl)phthalazin-1-amine

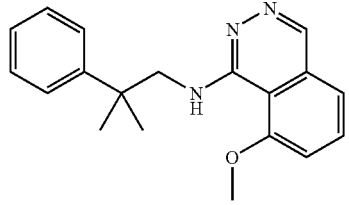

A mixture of 4-chloro-8-methoxy-N-(2-methyl-2-phenylpropyl)phthalazin-1-amine (Example 70, 30 mg, 0.088 mmol), ammonium formate (60 mg, 0.95 mmol) and 10% palladium on carbon (10 mg) in methanol was heated at 65° C. for three hours. The catalyst was removed by filtration through a pad of celite and the solvent was removed under vacuum. The residue was partitioned between water and methylene chloride, the organic layer was dried over magnesium sulfate, the solvent was removed and the product was purified by flash chromatography using 0-100% ethyl acetate-hexane to afford Example 71 (11 mg, 41%) as a tan gum. [M+H]/z 308. $^1$H NMR (400 MHz, CDCl$_3$) δ ppm 1.48 (s, 6 H), 3.59 (s, 3 H), 3.98 (d, J=4.83 Hz, 2H), 6.97 (d, J=7.91 Hz, 1 H), 7.02 (bs, 1 H), 7.23-7.32 (m, 2 H), 7.40 (t, J=7.69 Hz, 2 H), 7.50 (d, J=7.91 Hz, 2 H), 7.59 (t, J=7.91 Hz, 1 H), 8.71 (s, 1 H).

Example 72

5-methoxy-N-(2-methyl-2-phenylpropyl)benzo[e][1,2,3]oxathiazin-2-one-4-amine

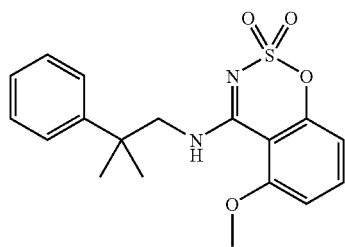

A mixture of potassium fluoride (15 mg, 0.25 mmol) and sulfonyl diimidazole (100 mg, 0.51 mmol in DMF (0.5 mL) was heated to 90° C. then a solution of 2-hydroxy-6-methoxy-N-(2-methyl-2-phenylpropyl)benzamidine (Compound B of Example 55, 76 mg, 0.25 mmol) in DMF (0.5 mL) was added slowly. The temperature was raised to 135° and maintained for two hours. The reaction was cooled, partitioned between chloroform and water, the organic solution was dried over magnesium sulfate and the solvent was removed under vacuum. The residue was purified by flash chromatography using 0-100% ethyl acetate-hexane gradient to afford Example 72 (25 mg, 25%) as a white solid. [M+H]/z 361. $^1$H NMR (400 MHz, CDCl$_3$) δ ppm 1.44 (s, 6 H), 3.51 (s, 3 H), 3.82 (d, J=5.27 Hz, 2 H), 6.69 (d, J=8.35 Hz, 1 H), 6.86 (d, J=7.91 Hz, 1 H), 7.28-7.34 (m, 1 H), 7.40-7.48 (m, 5 H), 7.93 (bs, 1 H).

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon particular embodiments, it will be obvious to those of ordinary skill in the art that variations in the particular compounds and methods may be used and that it is intended that the invention may be practiced otherwise than as specifically described herein. Accordingly, this invention includes all modifications encompassed within the spirit and scope of the invention as defined by the claims that follow.

What is claimed is:

1. A compound selected from the group consisting of:

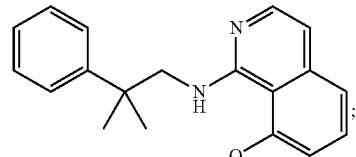

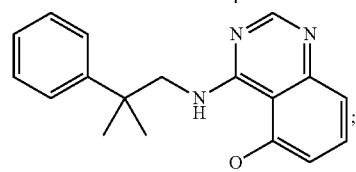

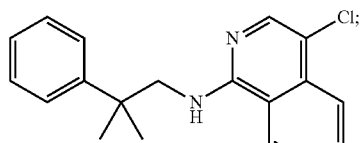

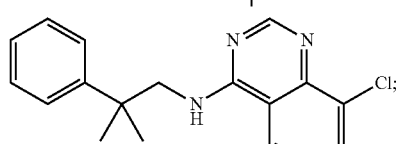

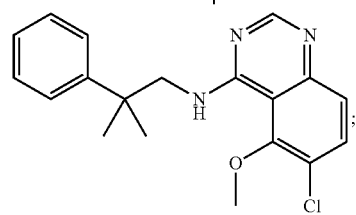

95
-continued
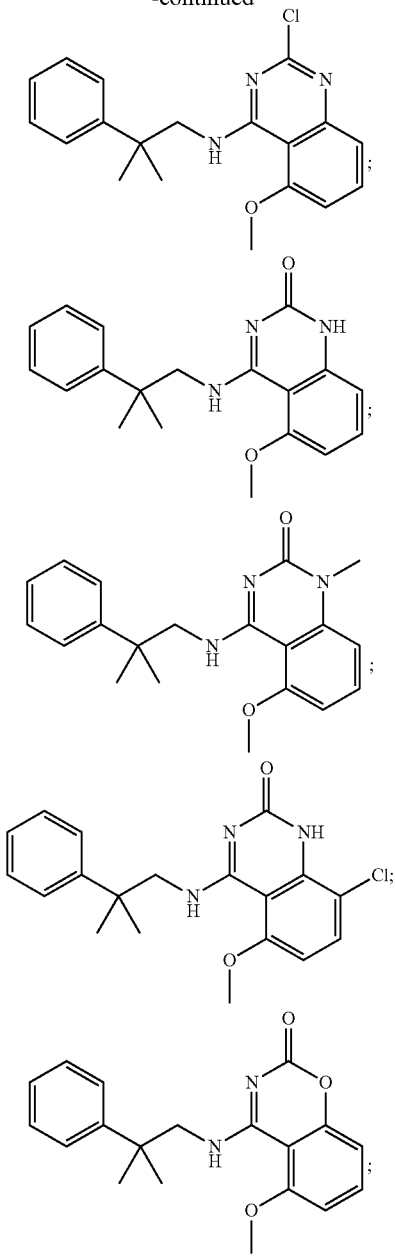
96
-continued
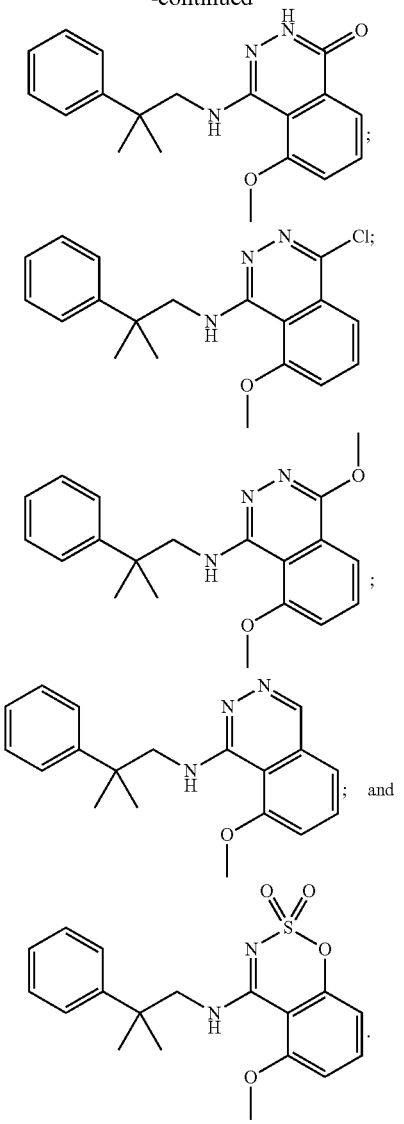
2. A pharmaceutical composition comprising a therapeutically effective amount of at least one compound of claim 1 and a pharmaceutically acceptable vehicle or carrier thereof.
* * * * *